United States Patent
Pevarello et al.

(10) Patent No.: US 6,716,856 B1
(45) Date of Patent: Apr. 6, 2004

(54) 4,5,6,7-TETRAHYDROINDAZOLE DERIVATIVES AS ANTITUMOR AGENTS

(75) Inventors: Paolo Pevarello, Pavia (IT); Manuela Villa, Como (IT); Mario Varasi, Milan (IT); Antonella Isacchi, Milan (IT)

(73) Assignee: Pharmacia & Tubjohn SPA, Milan (IT)

(*) Notice: Subject to any disclaimer, the term of this patent is extended or adjusted under 35 U.S.C. 154(b) by 0 days.

(21) Appl. No.: 09/926,478

(22) PCT Filed: May 4, 2000

(86) PCT No.: PCT/EP00/04208

§ 371 (c)(1),
(2), (4) Date: Nov. 9, 2001

(87) PCT Pub. No.: WO00/69846

PCT Pub. Date: Nov. 23, 2000

(30) Foreign Application Priority Data

May 12, 1999 (GB) ............................................. 9911053

(51) Int. Cl.[7] ............................................. A01N 43/40
(52) U.S. Cl. .................... 514/338; 514/339; 546/276.7; 546/277.1; 546/277.4
(58) Field of Search .......................... 546/276.7, 277.1, 546/277.4; 514/338, 339

(56) References Cited

U.S. PATENT DOCUMENTS

| 4,734,430 A | 3/1988 | Le Tourneau et al. |
| 6,335,342 B1 | 1/2002 | Longo et al. |

FOREIGN PATENT DOCUMENTS

| EP | 0 375 210 | 6/1990 |
| JP | 60-130521 | 7/1985 |
| JP | 62-99361 | 5/1987 |
| WO | WO 99/15500 | 4/1999 |
| WO | WO 99/17769 | 4/1999 |

OTHER PUBLICATIONS

Caplus english abstract DN 130:209635, Strakova et al 1998.*
Caplus English abstract DN 124:145982, Strakova et al 1994.*
Caplus English Abstract DN 123:285855, Stakova et al 1995.*
P. Schenone et al., Chemical Abstract, AN 1983:160635, J. Heterocyclic Chem., vol. 19, No. 6, pp. 1355–1361, "Reaction of 2–Dimethylaminomethylene–1,3–Diones with Dinucleophiles. I. Synthesis of 1,5–Disubstituted 4–Acylpyrazoles", 1982 (submitting English Abstract only).
G. Bianchi et al., Chemical Abstract, AN 1981:497308, J. Chem. Research(s), vol. 1, pp. 6–7, "Regioselectivity in the Reactions of Benzonitrile N–Phenylimide and Some Benzonitrile N–Oxides with α,β–Unsaturated Ketones", 1981 (submitting English Abstract only).

J. Sliede, et al., Chemical Abstract, AN 1977:423141, Latv. PSR Zinat. Akad. Vestis., Kim. Ser., vol. 1, pp. 112–113, "Bromination of 1–Phenyl 1–3,5,5, Trimethyl–4–Oxocyclcopentapy Razole", 1977 (submitting English Abstract only).

A. Ya. Strakov, et al., Chemical Abstract, AN 1977:29709, Latv. Psr Zinat. Akad. Vestis., Kim. Ser., vol. 4, pp. 469–470, "1–Phenyl–5,5–Dimethyl–and 1–Phenyl–3,5, 5–Trimethyl–4–Hydroxycyclopentapyrazole–4–Carboxylic Acids and Some of Their Reactions", 1976 (submitting English Abstract only).

A. Ya. Strakov, et al., Chemical Abstract, AN 1996:580759, Khim. Geterotsik. Soedin., vol. 5, pp. 708–710, "1–(1–Phthalazinyl)– and 1 (4–Methoxyphenyl)–6, 6–Dimethyl–4–OXO–4,5,6,7–Tetrahydroindazoles", 1996 (submitting English Abstract only).

A. Ya. Strakov, et al., Chemical Abstract, AN 1996:405050, Khim. Geterotsikl. Soedin., vol. 2, pp. 247–252, "Reaction of 2–Amino–and 2–Hydrazinobenzimidazoles with 2–Acyldimedones", 1996 (submitting English Abstract only).

D.B. Rubinov, et al., Chemical Abstract, AN 1993:517172, vol. 12, pp. 1617–1620, "Reaction of 2–Acylcylohexane–1, 3–Diones with 6–Hydrazinophenanthridine", 1992 (submitting English Abstract only).

E. Gudriniece, et al., Chemical Abstract, AN 1974:491415, Dokl. Akad. Nauk SSSR, vol. 216, No. 6, pp. 1293–1295, "1–Aryl–4–Carboxy–5–(β–Methyl–β–Carboxypropyl) Pyrazoles", 1974 (submitting English translation only, pp. 442–444).

A. J. Nunn, et al., Chemical Abstract, AN 1974:82796, J. Chem. Soc., Perkin Trans. 1, vol. 22, pp. 2697–2703, "Semmler–Wolff Aromatisation and Abnormal Beckmann and Schmidt Reactions of 3–Alkyl–4–Oxo–1–Phenyl–4,5, 6,7–Tetrahydroindazoles and Their Oximes in Polyphosphoric Acid", 1973 (submitting English Abstract only).

(List continued on next page.)

Primary Examiner—D. Margaret Seaman
(74) Attorney, Agent, or Firm—Akin Gump Strauss Hauer & Feld, LLP; Dwayne L. Mason

(57) ABSTRACT

Compounds which are 4,5,6,7-tetrahydroindazole derivative formula (1), wherein the dotted line (x) represents a single or double bond; n is 0 or 1; $R_1$, $R_2$ and $R_3$ have the meanings reported in the description; Ra, R'a, Rb, R'b, Rc, R'c have the meanings reported in the description, also comprising that Ra and Rb together and/or Ra and Rc together form a N-alkylpiperydinyl ring with 1 to 6 carbon atoms in the alkyl chain or a phenyl ring; or pharmaceutically acceptable salts thereof, are useful for treating cell proliferative disorders and Alzheimer's disease.

14 Claims, No Drawings

OTHER PUBLICATIONS

W. Sucrow, et al., Chemical Abstract, AN 1972:500891, Chem. ber., vol. 105, No. 7, pp. 2143–2155, "Die Umsetzung Von Dimedon Mit Hydrazonen"(Enehydrazines. 4. Reaction of Dimedone with Hydrazones, 1972 (submitting English Abstract only)

I. A. Strakova, et al., Chemical Abstract, AN 1970:487837 Khim. Geterotsikl. Soedin., vol. 4, pp. 520–524, "Alkylation of 3–Methyl–4–Oxo–4,5,6,7–Tetrahydroindazoles", 1970 (submitting English Abstract only).

I. A. Strakova et al., Chemical Abstracts, AN 1970:477133, Latv. PSR Zinat. Akad. Vestis., Kim. Ser., vol. 5, pp. 574–578, "Reduction of 1–Phenyl–3–Methyl–4–Oxo–4,5,6, 7–Tetrahydroindazoles", 1969 (submitting English Abstract only).

I. A. Strakova, et al., Chemical Abstracts, AN 1969:77862, Latv. PSR Zinat. Akad. Vestis., Kim. Kim. Ser., vol. 6, pp. 718–721, "6–Substituted 3–Methyl–4–Hydroxy–4,5,6, 7–Tetrahydroindazoles", 1968 (submitting English Abstract only).

I. A. Strakova, et al., Chemical Abstracts, AN 1967:516848, Latv. PSR Zinat. Akad. Vestis., Kim. Ser., vol. 6, pp. 680–683, "3,6,6–Trimethyl–4,5,6, 7–Trtrahydro–4–Indazoline Derivatives", 1966 (submitting English Abstract only).

* cited by examiner

4,5,6,7-TETRAHYDROINDAZOLE DERIVATIVES AS ANTITUMOR AGENTS

CROSS-REFERENCE

This is a 371 of PCT/EP00/04208 filed May 4, 2000 and also claims priority to United Kingdom 9911053.8 filed May 12, 1999.

The present invention relates to 4,5,6,7-tetrahydroindazole derivatives, to a process for their preparation, to pharmaceutical compositions containing them and to their use as antitumor agents. Several cytotoxic drugs such as, e.g. fluorouracil (5-FU), doxorubicin and camptothecins result to damage DNA or to affect cellular methabolic pathways and thus cause, in many cases, an indirect block of the cell cycle.

Therefore, by producing an irreversible damage to both normal and tumor cells, these agents result in a significant toxicity and side-effects.

In this respect, compounds capable of being highly specific antitumor agents by selectively leading to tumor cell arrest and apoptosis, with comparable efficacy but reduced toxicity than the currently available drugs, are desirable.

It is well known in the art that progression through the cell cycle is governed by a series of checkpoint controls which are regulated by a family of enzymes known as the cyclin-dependent kinases (cdk).

The cdks themselves are regulated at many levels such as, for instance, binding to cyclins.

For a general reference to cyclins and cyclin-dependent kinases see, for instance, Kevin R. Webster et al. in Exp. Opin. Invest. Drugs, 1998, Vol. 7(6), 865–887.

Checkpoint controls are defective in tumor cells due, in part, to disregulation of cdk activity. For example, altered expression of cyclin E and cdk's has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

It has now been found that the compounds of the invention, hereinafter referred to as 4,5,6,7-tetrahydroindazoles, are endowed with cdk/cyclin kinase inhibitory activity and are thus useful in therapy as antitumor agents whilst lacking, in terms of both toxicity and side effects, the aforementioned drawbacks known for currently available antitumor drugs.

In addition, besides of being useful in the treatment of cancer, these 4,5,6,7-tetrahydroindazoles are also useful in the treatment of a variety of other cell proliferative disorders such as, for instance, psoriasis, vascular smooth cell proliferation associated with atherosclerosis and post-surgical stenosis and restenosis, and in the treatment of Alzheimer's disease.

The compounds of the invention are also useful in the treatment and/or prevention of chemotherapy-induced or radiotherapy-induced alopecia.

Some 4,5,6,7-tetrahydroindazole derivatives, in particular 4-oxo-4,5,6,7-tetrahydroindazoles, are known in the art.

As an example, the compounds 1-phenyl-3,6,6-trimethyl-4-oxo-4,5,6,7-tetrahydroindazole, 1-phenyl-6,6-dimethyl-4-oxo-4,5,6,7-tetrahydroindazole, 1-phenyl-3-methyl-4-oxo-4,5,6,7-tetrahydroindazole and 1-(2-pyridyl)-3,6,6-trimethyl-4-oxo-4,5,6,7-tetrahydroindazole, as well as their corresponding 7-brominated derivatives, are all reported by Strakova I. et al., as useful synthetic intermediates [see, for a reference, Chemical Abstracts 124(1996):145892; 82(1975):4173z; 80(1974):133332h; 79(1973):92097u].

Likewise, 7-amino-1-phenyl-3,6,6-trimethyl-4-oxo-4,5,6,7-tetrahydroindazole has also been reported, as chemical intermediate by Strakova I. et al., in Latv. PSR Zinat. Akad. Vestis, Kim. Ser. 1974, (1), 113–14 [see, for a reference Chemical Abstracts 80(1974):133334k].

To the extent of our knowledge, however, none of these known compounds has been reported as possessing pharmaceutical activity, for instance antitumor activity and, even more particularly, cell cycle inhibitory activity.

Accordingly, the present invention provides a compound which is a 4,5,6,7-tetrahydroindazole derivative of formula (I)

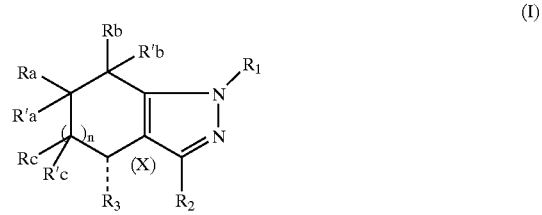

(I)

wherein:
the dotted line (x) represents a single or double bond;
n is 0 or 1;
$R_1$ is hydrogen or a group selected from straight or branched $C_1$–$C_6$ alkyl, aminocarbonyl, mono- or di-alkylaminocarbonyl with from 1 to 6 carbon atoms in the alkyl chains, aryl or arylalkyl with from 1 to 6 carbon atoms within the alkyl chain, each of which being optionally further substituted by one or more groups selected from halogen atoms, amino, nitro, cyano, hydroxy, $C_1$–$C_6$ alkyl or $C_1$–$C_6$ alkoxy groups;
$R_2$ is hydrogen or a group selected from straight or branched $C_1$–$C_6$ alkyl, $C_3$–$C_6$ cycloalkyl or cycloalkylalkyl with from 1 to 6 carbon atoms within the alkyl chain, aryl or arylalkyl with from 1 to 6 carbon atoms within the alkyl chain, each of which being optionally further substituted by one or more groups selected from halogens, cyano, straight or branched $C_1$–$C_6$ alkyl, straight or branched $C_1$–$C_6$ alkoxy, aryl, aryloxy, amino, alkylamino, dialkylamino with from 1 to 6 carbon atoms within the alkyl chain;
$R_3$ is hydroxy or a straight or branched $C_1$–$C_6$ alkoxy, amino, mono- or di-alkylamino with from 1 to 6 carbon atoms in the alkyl chains or, when (x) represents a double bond, $R_3$ is an oxygen atom (═O), a sulphur atom (═S) or an imino group (═N—$R_4$) wherein $R_4$ is hydrogen, hydroxy or a $C_1$–$C_6$ alkoxy group;
Ra and R'a are, each independently, hydrogen or straight or branched $C_1$–$C_6$ alkyl;
Rb and R'b are, each independently, hydrogen, halogen, atom or a group selected from straight or branched $C_1$–$C_6$ alkyl, straight or branched $C_1$–$C_6$ alkoxy, straight or branched $C_1$–$C_6$ alkylthio, cyano, hydroxy, amino, mono- or di-alkylamino with from 1 to 6 carbon atoms in the alkyl chains, arylthio, arylsulfinyl, arylsulfonyl, wherein each of the above aryl and alkyl moieties are optionally further substituted by one or more groups selected from halogen atoms, amino, nitro, hydroxy, $C_1$–$C_6$ alkyl or $C_1$–$C_6$ alkoxy groups;

Rc and R'c, present when n is 1, each independently represent hydrogen, straight or branched $C_1$–$C_6$ alkyl or cyano; or, Ra and Rb together and/or Ra and Rc together form a N-alkyl-piperydinyl ring with 1 to 6 carbon atoms in the alkyl chain or a phenyl ring;

or a pharmaceutically acceptable salt thereof; for use as a medicament.

The present invention further provides a compound which is a 4,5,6,7-tetrahydroindazole derivative of the above formula (I) in the manufacture of a medicament for treating cell proliferative disorders or Alzheimer's disease.

More in particular, the present invention provides a compound which is a 4,5,6,7-tetrahydroindazole derivative of the above formula (I) in the manufacture of a medicament for treating tumors.

In the present description, unless otherwise specified, with the term halogen atom we intend a fluorine, chlorine, bromine or iodine atom; chlorine, bromine and fluorine being preferred.

With the term straight or branched $C_1$–$C_6$ alkyl, alkylthio or alkoxy we intend a group selected from, methyl, ethyl, n-propyl, isopropyl, n-butyl, isobutyl, sec-butyl, tert-butyl, n-pentyl, n-hexyl, methylthio, ethylthio, n-propylthio, isopropylthio, n-butylthio, methoxy, ethoxy, n-propoxy, isopropoxy, n-butoxy or the like.

With the term $C_3$–$C_6$ cycloalkyl we intend a carbocyclic ring comprised from cyclopropyl, cyclobutyl, cyclopentyl or cyclohexyl.

The term aryl stands herewith for phenyl or for an optionally benzocondensed 5 or 6 membered aromatic heterocycle having one or more, preferably 1 or 2, heteroatoms selected from nitrogen, oxygen and sulphur such as, for instance, pyrrole, furan, thiophene, imidazole, pyrazole, thiazole, oxazole, isoxazole, pyridine, pyrazine, pyrimidine or the like.

Pharmaceutically acceptable salts of the compounds of formula (I) are the acid addition salts with inorganic or organic acids, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

Among the compounds of formula (I) above reported, several 4,5,6,7-tetrahydroindazoles result to be novel.

Therefore, the present invention further provides a compound which is a 4,5,6,7-tetrahydroindazole derivative formula (I)

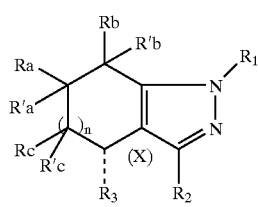

(I)

wherein:
the dotted line (x) represents a single or double bond;
n is 0 or 1;
$R_1$ is hydrogen or a group selected from straight or branched $C_1$–$C_6$ alkyl, aminocarbonyl, mono- or di-alkylaminocarbonyl with from 1 to 6 carbon atoms in the alkyl chains, aryl or arylalkyl with from 1 to 6 carbon atoms within the alkyl chain, each of which being optionally further substituted by one or more groups selected from halogen atoms, amino, nitro, cyano, hydroxy, $C_1$–$C_6$ alkyl or $C_1$–$C_6$ alkoxy groups;
$R_2$ is hydrogen or a group selected from straight or branched $C_1$–$C_6$ alkyl, $C_3$–$C_6$ cycloalkyl or cycloalkylalkyl with from 1 to 6 carbon atoms within the alkyl chain, aryl or arylalkyl with from 1 to 6 carbon atoms within the alkyl chain, each of which being optionally further substituted by one or more groups selected from halogens, cyano, straight or branched $C_1$–$C_6$ alkyl, straight or branched $C_1$–$C_6$ alkoxy, aryl, aryloxy, amino, alkylamino, dialkylamino with from 1 to 6 carbon atoms within the alkyl chain;
$R_3$ is hydroxy or a straight or branched $C_1$–$C_6$ alkoxy, amino, mono- or di-alkylamino with from 1 to 6 carbon atoms in the alkyl chains or, when (x) represents a double bond, $R_3$ is an oxygen atom (=O), a sulphur atom (=S) or an imino group (=N—$R_4$) wherein $R_4$ is hydrogen, hydroxy or a $C_1$–$C_6$ alkoxy group;
Ra and R'a are, each independently, hydrogen or straight or branched $C_1$–$C_6$ alkyl;
Rb and R'b are, each independently, hydrogen, halogen, atom or a group selected from straight or branched $C_1$–$C_6$ alkyl, straight or branched $C_1$–$C_6$ alkoxy, straight or branched $C_1$–$C_6$ alkylthio, cyano, hydroxy, amino, mono- or di-alkylamino with from 1 to 6 carbon atoms in the alkyl chains, arylthio, arylsulfinyl, arylsulfonyl, wherein each of the above aryl and alkyl moieties are optionally further substituted by one or more groups selected from halogen atoms, amino, nitro, hydroxy, $C_1C_6$ alkyl or $C_1$–$C_6$ alkoxy groups;
Rc and R'c, present when n is 1, each independently represent hydrogen, straight or branched $C_1$–$C_6$ alkyl or cyano; or,
Ra and Rb together and/or Ra and Rc together form a N-alkyl-piperydinyl ring with 1 to 6 carbon atoms in the alkyl chain or a phenyl ring;
or a pharmaceutically acceptable salt thereof;
with the provisos that:
a) when n is 1, R'b, Rc and R'c are hydrogen atoms, (x) is a double bond, $R_1$ is phenyl, $R_2$, Ra and R'a are, each independently, hydrogen or methyl, and $R_3$ is oxygen, then, Rb is other than hydrogen, bromine or amino;
b) the compound is not 1-(2-pyridyl)-3,6,6-trimethyl-4-oxo-4,5,6,7-tetrahydroindazole and 7-bromo-1-(2-pyridyl)-3,6,6-trimethyl-4-oxo-4,5,6,7-tetrahydroindazole.

The compounds of formula (I) may have asymmetric carbon atoms and may therefore exist either as racemic admixtures or as individual optical isomers.

Accordingly, all the possible isomers of the compounds of formula (I) and their admixtures and of both the metabolites and the pharmaceutically acceptable bio-precursors (otherwise referred to as pro-drugs) are also within the scope of the present invention.

A class of preferred compounds of the invention are the compounds of formula (I) wherein n is 1, R'b, Rc and R'c are hydrogen atoms, (x) is a double bond, $R_3$ is an oxygen atom or an imino group and $R_2$, Ra and R'a are, each independently, $C_1$–$C_3$ alkyl groups.

Another class of preferred compounds of the invention are the compounds of formula (I) wherein wherein n is 1, R'b, Rc and R'c are hydrogen atoms, (x) is a single bond, $R_3$ is hydroxy or a $C_1$–$C_3$ alkoxy group and $R_2$, Ra and R'a are, each independently, $C_1$–$C_3$ alkyl groups.

Examples of specific compounds of the invention either as such or for use as a medicament, whenever appropriate in the form of pharmaceutically acceptable salts, are the following:

1. 7-bromo-1-(2-pyridyl)-3,6,6-trimethyl-4-oxo-4,5,6,7-tetrahydroindazole;
2. 1-(2-pyridyl)-3,6,6-trimethyl-4-oxo-4,5,6,7-tetrahydroindazole;
3. 7-fluoro-1-(2-pyridyl)-3,6,6-trimethyl-4-oxo-4,5,6,7-tetrahydroindazole;
4. 7-methoxy-1-(2-pyridyl)-3,6,6-trimethyl-4-oxo-4,5,6,7-tetrahydroindazole;
5. 7-hydroxy-1-(2-pyridyl)-3,6,6-trimethyl-4-oxo-4,5,6,7-tetrahydroindazole;
6. 7-(N,N-dimethylamino)-1-(2-pyridyl)-3,6,6-trimethyl-4-oxo-4,5,6,7-tetrahydroindazole;
7. 7-phenylthio-1-(2-pyridyl)-3,6,6-trimethyl-4-oxo-4,5,6,7-tetrahydroindazole;
8. 7-phenylsulfonyl-1-(2-pyridyl)-3,6,6-trimethyl-4-oxo-4,5,6,7-tetrahydroindazole;
9. 4-(N-hydroxy-imino)-1-(2-pyridyl)-3,6,6-trimethyl-4,5,6,7-tetrahydroindazole;
10. 7-bromo-4-(N-hydroxy-imino)-1-(2-pyridyl)-3,6,6-trimethyl-4,5,6,7-tetrahydroindazole;
11. 7-ethoxy-4-(N-hydroxy-imino)-3,6,6-trimethyl-4,5,6,7-tetrahydroindazole;
12. 4-hydroxy-1-(2-pyridyl)-3,6,6-trimethyl-4,5,6,7-tetrahydroindazole;
13. 4-methoxy-1-(2-pyridyl)-3,6,6-trimethyl-4,5,6,7-tetrahydroindazole;
14. 1-phenylmethyl-3,6,6-trimethyl-4-oxo-4,5,6,7-tetrahydroindazole;
15. 1-(3-nitrophenyl)-3,6,6-trimethyl-4-oxo-4,5,6,7-tetrahydroindazole;
16. 1-(3-aminophenyl)-3,6,6-trimethyl-4-oxo-4,5,6,7-tetrahydroindazole;
17. 1-aminocarbonyl-3,6,6-trimethyl-4-oxo-4,5,6,7-tetrahydroindazole;
18. 1,3-dimethyl-1,5,6,7-tetrahydro-4H-indazol-4-one;
19. 1-(2-hydroxyethyl)-3-methyl-1,5,6,7-tetrahydro-4H-indazol-4-one;
20. 3-methyl-1-phenyl-1,5,6,7-tetrahydro-4H-indazol-4-one;
21. 3-methyl-1-(2-pyridinyl)-1,5,6,7-tetrahydro-4H-indazol-4-one;
22. 1-(6-chloro-3-pyridazinyl)-3-methyl-1,5,6,7-tetrahydro-4H-indazol-4-one;
23. 1-(3-methoxyphenyl)-3-methyl-1,5,6,7-tetrahydro-4H-indazol-4-one;
24. 1-(3-chlorophenyl)-3-methyl-1,5,6,7-tetrahydro-4H-indazol-4-one;
25. 1-(4-isopropylphenyl)-3-methyl-1,5,6,7-tetrahydro-4H-indazol-4-one;
26. 1-(4-iodophenyl)-3-methyl-1,5,6,7-tetrahydro-4H-indazol-4-one;
27. 3-cyclopropyl-1-methyl-1,5,6,7-tetrahydro-4H-indazol-4-one;
28. 3-cyclopropyl-1-(2-hydroxyethyl)-1,5,6,7-tetrahydro-4H-indazol-4-one;
29. 3-cyclopropyl-1-phenyl-1,5,6,7-tetrahydro-4H-indazol-4-one;
30. 3-cyclopropyl-1-(2-pyridinyl)-1,5,6,7-tetrahydro-4H-indazol-4-one;
31. 1-(6-chloro-3-pyridazinyl)-3-cyclopropyl-1,5,6,7-tetrahydro-4H-indazol-4-one;
32. 3-cyclopropyl-1-(3-methoxyphenyl)-1,5,6,7-tetrahydro-4H-indazol-4-one;
33. 1-(3-chlorophenyl)-3-cyclopropyl-1,5,6,7-tetrahydro-4H-indazol-4-one;
34. 3-cyclopropyl-1-(4-isopropylphenyl)-1,5,6,7-tetrahydro-4H-indazol-4-one;
35. 3-cyclopropyl-1-(4-iodophenyl)-1,5,6,7-tetrahydro-4H-indazol-4-one;
36. 3-isopropyl-1-methyl-1,5,6,7-tetrahydro-4H-indazol-4-one;
37. 1-(2-hydroxyethyl)-3-isopropyl-1,5,6,7-tetrahydro-4H-indazol-4-one;
38. 3-isopropyl-1-phenyl-1,5,6,7-tetrahydro-4H-indazol-4-one;
39. 3-isopropyl-1-(2-pyridinyl)-1,5,6,7-tetrahydro-4H-indazol-4-one;
40. 1-(6-chloro-3-pyridazinyl)-3-isopropyl-1,5,6,7-tetrahydro-4H-indazol-4-one;
41. 3-isopropyl-1-(3-methoxyphenyl)-1,5,6,7-tetrahydro-4H-indazol-4-one;
42. 1-(3-chlorophenyl)-3-isopropyl-1,5,6,7-tetrahydro-4H-indazol-4-one;
43. 3-isopropyl-1-(4-isopropylphenyl)-1,5,6,7-tetrahydro-4H-indazol-4-one;
44. 1-(4-iodophenyl)-3-isopropyl-1,5,6,7-tetrahydro-4H-indazol-4-one;
45. 1-methyl-3-propyl-1,5,6,7-tetrahydro-4H-indazol-4-one;
46. 1-(2-hydroxyethyl)-3-propyl-1,5,6,7-tetrahydro-4H-indazol-4-one;
47. 1-phenyl-3-propyl-1,5,6,7-tetrahydro-4H-indazol-4-one;
48. 3-propyl-1-(2-pyridinyl)-1,5,6,7-tetrahydro-4H-indazol-4-one;
49. 1-(6-chloro-3-pyridazinyl)-3-propyl-1,5,6,7-tetrahydro-4H-indazol-4-one;
50. 1-(3-methoxyphenyl)-3-propyl-1,5,6,7-tetrahydro-4H-indazol-4-one;
51. 1-(3-chlorophenyl)-3-propyl-1,5,6,7-tetrahydro-4H-indazol-4-one;
52. 1-(4-isopropylphenyl)-3-propyl-1,5,6,7-tetrahydro-4H-indazol-4-one;

53. 1-(4-iodophenyl)-3-propyl-1,5,6,7-tetrahydro-4H-indazol-4-one;
54. 3-tertbuty-1methyl-1,5,6,7-tetrahydro-4H-indazol-4-one;
55. 1-(2-hydroxyethyl)-3-tertbutyl-1,5,6,7-tetrahydro-4H-indazol-4-one;
56. 1-phenyl-3-tertbutyl-1,5,6,7-tetrahydro-4H-indazol-4-one;
57. 1-(2-pyridinyl)-3-tertbutyl-1,5,6,7-tetrahydro-4H-indazol-4-one;
58. 1-(6-chloro-3-pyridazinyl)-3-tertbutyl-1,5,6,7-tetrahydro-4H-indazol-4-one;
59. 1-(3-methoxyphenyl)-3-tertbutyl-1,5,6,7-tetrahydro-4H-indazol-4-one;
60. 1-(3-chlorophenyl)-3-tertbutyl-1,5,6,7-tetrahydro-4H-indazol-4-one;
61. 1-(4-isopropylphenyl)-3-tertbutyl-1-1,5,6,7-tetrahydro-4H-indazol-4-one;
62. 1-(4-iodophenyl)-3-tertbutyl-1,5,6,7-tetrahydro-4H-indazol-4-one;
63. 3-isobutyl-1-methyl-1,5,6,7-tetrahydro-4H-indazol-4-one;
64. 1-(2-hydroxyethyl)-3-isobutyl-1,5,6,7-tetrahydro-4H-indazol-4-one;
65. 3-isobutyl-1-phenyl-1,5,6,7-tetrahydro-4H-indazol-4-one;
66. 3-isobutyl-1-(2-pyridinyl)-1,5,6,7-tetrahydro-4H-indazol-4-one;
67. 1-(6-chloro-3-pyridazinyl)-3-isobutyl-1,5,6,7-tetrahydro-4H-indazol-4-one;
68. 3-isobutyl-1-(3-methoxyphenyl)-1,5,6,7-tetrahydro-4H-indazol-4-one;
69. 1-(3-chlorophenyl)-3-isobutyl-1,5,6,7-tetrahydro-4H-indazol-4-one;
70. 3-isobutyl-1-(4-isopropylphenyl)-1-1,5,6,7-tetrahydro-4H-indazol-4-one;
71. 1-(4-iodophenyl)-3-isobutyl-1,5,6,7-tetrahydro-4H-indazol-4-one;
72. 1-methyl-3-(2,4,4-trimethylpentyl)-1,5,6,7-tetrahydro-4H-indazol-4-one;
73. 1-(2-hydroxyethyl)-3-(2,4,4-trimethylpentyl)-1,5,6,7-tetrahydro-4H-indazol-4-one;
74. 1-phenyl-3-(2,4,4-trimethylpentyl)-1,5,6,7-tetrahydro-4H-indazol-4-one;
75. 3-(2,4,4-trimethylpentyl)-1-(2-pyridinyl)-1,5,6,7-tetrahydro-4H-indazol-4-one;
76. 1-(6-chloro-3-pyridazinyl)-3-(2,4,4-trimethylpentyl)-1,5,6,7-tetrahydro-4H-indazol-4-one;
77. 1-(3-methoxyphenyl)-3-(2,4,4-trimethylpentyl)-1,5,6,7-tetrahydro-4H-indazol-4-one;
78. 1-(3-chlorophenyl)-3-(2,4,4-trimethylpentyl)-1,5,6,7-tetrahydro-4H-indazol-4-one;
79. 1-(4-isopropylphenyl)-3-(2,4,4-trimethylpentyl)-1-1,5,6,7-tetrahydro-4H-indazol-4-one;
80. 1-(4-iodophenyl)-3-(2,4,4-trimethylpentyl)-1,5,6,7-tetrahydro-4H-indazol-4-one;
81. 1,3,6-trimethyl-1,5,6,7-tetrahydro-4H-indazol-4-one;
82. 1-(2-hydroxyethyl)-3,6-dimethyl-1,5,6,7-tetrahydro-4H-indazol-4-one;
83. 3,6-dimethyl-1-phenyl-1,5,6,7-tetrahydro-4H-indazol-4-one;
84. 3,6-dimethyl-1-(2-pyridinyl)-1,5,6,7-tetrahydro-4H-indazol-4-one;
85. 1-(6-chloro-3-pyridazinyl)-3,6-dimethyl-1,5,6,7-tetrahydro-4H-indazol-4-one;
86. 1-(3-methoxyphenyl)-3,6-dimethyl-1,5,6,7-tetrahydro-4H-indazol-4-one;
87. 1-(3-chlorophenyl)-3,6-dimethyl-1,5,6,7-tetrahydro-4H-indazol-4-one;
88. 1-(4-isopropylphenyl)-3,6-dimethyl-1,5,6,7-tetrahydro-4H-indazol-4-one;
89. 1-(4-iodophenyl)-3,6-dimethyl-1,5,6,7-tetrahydro-4H-indazol-4-one;
90. 3-cyclopropyl-1,6-dimethyl-1,5,6,7-tetrahydro-4H-indazol-4-one;
91. 3-cyclopropyl-1-(2-hydroxyethyl)-6-methyl-1,5,6,7-tetrahydro-4H-indazol-4-one;
92. 3-cyclopropyl-6-methyl-1-phenyl-1,5,6,7-tetrahydro-4H-indazol-4-one;
93. 3-cyclopropyl-6-methyl-1-(2-pyridinyl)-1,5,6,7-tetrahydro-4H-indazol-4-one;
94. 1-(6-.chloro-3-pyridazinyl)-3-cyclopropyl-6-methyl-1,5,6,7-tetrahydro-4H-indazol-4-one;
95. 3-cyclopropyl-1-(3-methoxyphenyl)-6-methyl-1,5,6,7-tetrahydro-4H-indazol-4-one;
96. 1-(3-chlorophenyl)-3-cyclopropyl-6-methyl-1,5,6,7-tetrahydro-4H-indazol-4-one;
97. 3-cyclopropyl-1-(4-isopropylphenyl)-6-methyl-1,5,6,7-tetrahydro-4H-indazol-4-one;
98. 3-cyclopropyl-1-(4-iodophenyl)-6-methyl-1,5,6,7-tetrahydro-4H-indazol-4-one;
99. 3-isopropyl-1,6-dimethyl-1,5,6,7-tetrahydro-4H-indazol-4-one;
100. 1-(2-hydroxyethyl)-3-isopropyl-6-methyl-1,5,6,7-tetrahydro-4H-indazol-4-one;
101. 3-isopropyl-6-methyl-1-phenyl-1,5,6,7-tetrahydro-4H-indazol-4-one;
102. 3-isopropyl-6-methyl-1-(2-pyridinyl)-1,5,6,7-tetrahydro-4H-indazol-4-one;
103. 1-(6-chloro-3-pyridazinyl)-3-isopropyl-6-methyl-1,5,6,7-tetrahydro-4H-indazol-4-one;
104. 3-isopropyl-1-(3-methoxyphenyl)-6-methyl-1,5,6,7-tetrahydro-4H-indazol-4-one;
105. 1-(3-chlorophenyl)-3-isopropyl-6-methyl-1,5,6,7-tetrahydro-4H-indazol-4-one;
106. 3-isopropyl-1-(4-isopropylphenyl)-6-methyl-1,5,6,7-tetrahydro-4H-indazol-4-one;
107. 1-(4-iodophenyl)-3-isopropyl-6-methyl-1,5,6,7-tetrahydro-4H-indazol-4-one;
108. 1,6-dimethyl-3-propyl-1,5,6,7-tetrahydro-4H-indazol-4-one;
109. 1-(2-hydroxyethyl)-6-methyl-3-propyl-1,5,6,7-tetrahydro-4H-indazol-4-one;
110. 6-methyl-1-phenyl-3-propyl-1,5,6,7-tetrahydro-4H-indazol-4-one;
111. 6-methyl-3-propyl-1-(2-pyridinyl)-1,5,6,7-tetrahydro-4H-indazol-4-one;
112. 1-(6-chloro-3-7pyridazinyl)-6-methyl-3-propyl-1,5,6,7-tetrahydro-4H-indazol-4-one;
113. 1-(3-methoxyphenyl)-6-methyl-3-propyl-1,5,6,7-tetrahydro-4H-indazol-4-one;
114. 1-(3-chlorophenyl)-6-methyl-3-propyl-1,5,6,7-tetrahydro-4H-indazol-4-one;

115. 1-(4-isopropylphenyl)-6-methyl-3-propyl-1,5,6,7-tetrahydro-4H-indazol-4-one;
116. 1-(4-iodophenyl)-6-methyl-6-methyl-3-propyl-1,5,6,7-tetrahydro-4H-indazol-4-one;
117. 3-tertbuty-1,6-dimethyl-1-1,5,6,7-tetrahydro-4H-indazol-4-one;
118. 1-(2-hydroxyethyl)-6-methyl-3-tertbutyl-1,5,6,7-tetrahydro-4H-indazol-4-one;
119. 6-methyl-1-phenyl-3-tertbutyl-1,5,6,7-tetrahydro-4H-indazol-4-one;
120. 6-methyl-1-(2-pyridinyl)-3-tertbutyl-1,5,6,7-tetrahydro-4H-indazol-4-one;
121. 1-(6-chloro-3-pyridazinyl)-6-methyl-3-tertbutyl-1,5,6,7-tetrahydro-4H-indazol-4-one;
122. 1-(3-methoxyphenyl)-6-methyl-3-tertbutyl-1,5,6,7-tetrahydro-4H-indazol-4-one;
123. 1-(3-chlorophenyl)-6-methyl-3-tertbutyl-1,5,6,7-tetrahydro-4H-indazol-4-one;
124. 1-(4-isopropylphenyl)-6-methyl-3-tertbutyl-1-1,5,6,7-tetrahydro-4H-indazol-4-one;
125. 1-(4-iodophenyl)-6-methyl-3-tertbutyl-1,5,6,7-tetrahydro-4H-indazol-4-one;
126. 3-isobutyl-1,6-dimethyl-1,5,6,7-tetrahydro-4H-indazol-4-one;
127. 1-(2-hydroxyethyl)-3-isobutyl-6-methyl-1,5,6,7-tetrahydro-4H-indazol-4-one;
128. 3-isobutyl-6-methyl-1-phenyl-1,5,6,7-tetrahydro-4H-indazol-4-one;
129. 3-isobutyl-6-methyl-1-(2-pyridinyl)-1,5,6,7-tetrahydro-4H-indazol-4-one;
130. 1-(6-chloro-3-pyridazinyl)-3-isobutyl-6-methyl-1,5,6,7-tetrahydro-4H-indazol-4-one;
131. 3-isobutyl-1-(3-methoxyphenyl)-6-methyl-1,5,6,7-tetrahydro-4H-indazol-4-one;
132. 1-(3-chlorophenyl)-3-isobutyl-6-methyl-1,5,6,7-tetrahydro-4H-indazol-4-one;
133. 3-isobutyl-1-(4-isopropylphenyl)-6-methyl-1-1,5,6,7-tetrahydro-4H-indazol-4-one;
134. 1-(4-iodophenyl)-3-isobutyl-6-methyl-1,5,6,7-tetrahydro-4H-indazol-4-one;
135. 1,6-dimethyl-3-(2,4,4-trimethylpentyl)-1,5,6,7-tetrahydro-4H-indazol-4-one;
136. 1-(2-hydroxyethyl)-6-methyl-3-(2,4,4-trimethylpentyl)-1,5,6,7-tetrahydro-4H-indazol-4-one;
137. 6-methyl-1-phenyl-3-(2,4,4-trimethylpentyl)-1,5,6,7-tetrahydro-4H-indazol-4-one;
138. 6-methyl-3-(2,4,4-trimethylpentyl)-1-(2-pyridinyl)-1,5,6,7-tetrahydro-4H-indazol-4-one;
139. 1-(6-chloro-3-pyridazinyl)-6-methyl-3-(2,4,4-trimethylpentyl)-1,5,6,7-tetrahydro-4H-indazol-4-one;
140. 1-(3-methoxyphenyl)-6-methyl-3-(2,4,4-trimethylpentyl)-1,5,6,7-tetrahydro-4H-indazol-4-one;
141. 1-(3-chlorophenyl)-6-methyl-3-(2,4,4-trimethylpentyl)-1,5,6,7-tetrahydro-4H-indazol-4-one;
142. 1-(4-isopropylphenyl)-6-methyl-3-(2,4,4-trimethylpentyl)-1-1,5,6,7-tetrahydro-4H-indazol-4-one;
143. 1-(4-iodophenyl)-6-methyl-3-(2,4,4-trimethylpentyl)-1,5,6,7-tetrahydro-4H-indazol-4-one;
144. 6-isopropyl-1,3-dimethyl-1,5,6,7-tetrahydro-4H-indazol-4-one;
145. 1-(2-hydroxyethyl)-6-isopropyl-3-methyl-1,5,6,7-tetrahydro-4H-indazol-4-one;
146. 6-isopropyl-3-methyl-1-phenyl-1,5,6,7-tetrahydro-4H-indazol-4-one;
147. 6-isopropyl-3-methyl-1-(2-pyridinyl)-1,5,6,7-tetrahydro-4H-indazol-4-one;
148. 1-(6-chloro-3-pyridazinyl)-6-isopropyl-3-methyl-1,5,6,7-tetrahydro-4H-indazol-4-one;
149. 6-isopropyl-1-(3-methoxyphenyl)-3-methyl-1,5,6,7-tetrahydro-4H-indazol-4-one;
150. 1-(3-chlorophenyl)-6-isopropyl-3-methyl-1,5,6,7-tetrahydro-4H-indazol-4-one;
151. 6-isopropyl-1-(4-isopropylphenyl)-3-methyl-1,5,6,7-tetrahydro-4H-indazol-4-one;
152. 1-(4-iodophenyl)-6-isopropyl-3-methyl-1,5,6,7-tetrahydro-4H-indazol-4-one;
153. 3-cyclopropyl-6-isopropyl-1-methyl-1,5,6,7-tetrahydro-4H-indazol-4-one;
154. 3-cyclopropyl-1-(2-hydroxyethyl)-6-isopropyl-1,5,6,7-tetrahydro-4H-indazol-4-one;
155. 3-cyclopropyl-6-isopropyl-1-phenyl-1,5,6,7-tetrahydro-4H-indazol-4-one;
156. 3-cyclopropyl-6-isopropyl-1-(2-pyridinyl)-1,5,6,7-tetrahydro-4H-indazol-4-one;
157. 1-(6-chloro-3-pyridazinyl)-3-cyclopropyl-6-isopropyl-1,5,6,7-tetrahydro-4H-indazol-4-one;
158. 3-cyclopropyl-6-isopropyl-1-(3-methoxyphenyl)-1,5,6,7-tetrahydro-4H-indazol-4-one;
159. 1-(3-chlorophenyl)-3-cyclopropyl-6-isopropyl-1,5,6,7-tetrahydro-4H-indazol-4-one;
160. 3-cyclopropyl-6-isopropyl-1-(4-isopropylphenyl)-1,5,6,7-tetrahydro-4H-indazol-4-one;
161. 3-cyclopropyl-1-(4-iodophenyl)-6-isopropyl-1,5,6,7-tetrahydro-4H-indazol-4-one;
162. 3,6-diisopropyl-1-methyl-1,5,6,7-tetrahydro-4H-indazol-4-one;
163. 1-(2-hydroxyethyl)-3,6-diisopropyl-1,5,6,7-tetrahydro-4H-indazol-4-one;
164. 3,6-diisopropyl-1-phenyl-1,5,6,7-tetrahydro-4H-indazol-4-one;
165. 3,6-diisopropyl-1-(2-pyridinyl)-1,5,6,7-tetrahydro-4H-indazol-4-one;
166. 1-(6-chloro-3-pyridazinyl)-3,6-diisopropyl-1,5,6,7-tetrahydro-4H-indazol-4-one;
167. 3,6-diisopropyl-1-(3-methoxyphenyl)-1,5,6,7-tetrahydro-4H-indazol-4-one;
168. 1-(3-chlorophenyl)-3,6-diisopropyl-1,5,6,7-tetrahydro-4H-indazol-4-one;
169. 3,6-diisopropyl-1-(4-isopropylphenyl)-1,5,6,7-tetrahydro-4H-indazol-4-one;
170. 1-(4-iodophenyl)-3,6-diisopropyl-1,5,6,7-tetrahydro-4H-indazol-4-one;
171. 1-methyl-6-isopropyl-3-propyl-1,5,6,7-tetrahydro-4H-indazol-4-one;
172. 1-(2-hydroxyethyl)-6-isopropyl-3-propyl-1,5,6,7-tetrahydro-4H-indazol-4-one;
173. 6-isopropyl-1-phenyl-3-propyl-1,5,6,7-tetrahydro-4H-indazol-4-one;
174. 6-isopropyl-3-propyl-1-(2-pyridinyl)-1,5,6,7-tetrahydro-4H-indazol-4-one;
175. 1-(6-chloro-3-pyridazinyl)-6-isopropyl-3-propyl-1,5,6,7-tetrahydro-4H-indazol-4-one;
176. 1-(3-methoxyphenyl)-6-isopropyl-3-propyl-1,5,6,7-tetrahydro-4H-indazol-4-one;

177. 1-(3-chlorophenyl)-6-isopropyl-3-propyl-1,5,6,7-tetrahydro-4H-indazol-4-one;
178. 1-(4-isopropylphenyl)-6-isopropyl-3-propyl-1,5,6,7-tetrahydro-4H-indazol-4-one;
179. 1-(4-iodophenyl)-6-isopropyl-3-propyl-1,5,6,7-tetrahydro-4H-indazol-4-one;
180. 6-isopropyl-3-tertbuty-1-methyl-1-1,5,6,7-tetrahydro-4H-indazol-4-one;
181. 1-(2-hydroxyethyl)-6-isopropyl-3-tertbutyl-1,5,6,7-tetrahydro-4H-indazol-4-one;
182. 6-isopropyl-1-phenyl-3-tertbutyl-1,5,6,7-tetrahydro-4H-indazol-4-one;
183. 6-isopropyl-1-(2-pyridinyl)-3-tertbutyl-1,5,6,7-tetrahydro-4H-indazol-4-one;
184. 1-(6-chloro-3-pyridazinyl)-6-isopropyl-3-tertbutyl-1,5,6,7-tetrahydro-4H-indazol-4-one;
185. 6-isopropyl-1-(3-methoxyphenyl)-3-tertbutyl-1,5,6,7-tetrahydro-4H-indazol-4-one;
186. 1-(3-chlorophenyl)-6-isopropyl-3-tertbutyl-1,5,6,7-tetrahydro-4H-indazol-4-one;
187. 6-isopropyl-1-(4-isopropylphenyl)-3-tertbutyl-1-1,5,6,7-tetrahydro-4H-indazol-4-one;
188. 1-(4-iodophenyl)-6-isopropyl-3-tertbutyl-1,5,6,7-tetrahydro-4H-indazol-4-one;
189. 3-isobutyl-6-isopropyl-1-methyl-1,5,6,7-tetrahydro-4H-indazol-4-one;
190. 1-(2-hydroxyethyl)-3-isobutyl-6-isopropyl-1,5,6,7-tetrahydro-4H-indazol-4-one;
191. 3-isobutyl-6-isopropyl-1-phenyl-1,5,6,7-tetrahydro-4H-indazol-4-one;
192. 3-isobutyl-6-isopropyl-1-(2-pyridinyl)-1,5,6,7-tetrahydro-4H-indazol-4-one;
193. 1-(6-chloro-3-pyridazinyl)-3-isobutyl-6-isopropyl-1,5,6,7-tetrahydro-4H-indazol-4-one;
194. 3-isobutyl-6-isopropyl-1-(3-methoxyphenyl)-1,5,6,7-tetrahydro-4H-indazol-4-one;
195. 1-(3-chlorophenyl)-3-isobutyl-6-isopropyl-1,5,6,7-tetrahydro-4H-indazol-4-one;
196. 3-isobutyl-6-isopropyl-1-(4-isopropylphenyl)-1-1,5,6,7-tetrahydro-4H-indazol-4-one;
197. 1-(4-iodophenyl)-3-isobutyl-6-isopropyl-1,5,6,7-tetrahydro-4H-indazol-4-one;
198. 6-isopropyl-1-methyl-3-(2,4,4-trimethylpentyl)-1,5,6,7-tetrahydro-4H-indazol-4-one;
199. 1-(2-hydroxyethyl)-6-isopropyl-3-(2,4,4-trimethylpentyl)-1,5,6,7-tetrahydro-4H-indazol-4-one;
200. 6-isopropyl-1-phenyl-3-(2,4,4-trimethylpentyl)-1,5,6,7-tetrahydro-4H-indazol-4-one;
201. 6-isopropyl-3-(2,4,4-trimethylpentyl)-1-(2-pyridinyl)-1,5,6,7-tetrahydro-4H-indazol-4-one;
202. 1-(6-chloro-3-pyridazinyl)-6-isopropyl-3-(2,4,4-trimethylpentyl)-1,5,6,7-tetrahydro-4H-indazol-4-one;
203. 6-isopropyl-1-(3-methoxyphenyl)-3-(2,4,4-trimethylpentyl)-1,5,6,7-tetrahydro-4H-indazol-4-one;
204. 1-(3-chlorophenyl)-6-isopropyl-3-(2,4,4-trimethylpentyl)-1,5,6,7-tetrahydro-4H-indazol-4-one;
205. 6-isopropyl-1-(4-isopropylphenyl)-3-(2,4,4-trimethylpentyl)-1-1,5,6,7-tetrahydro-4H-indazol-4-one;
206. 1-(4-iodophenyl)-6-isopropyl-3-(2,4,4-trimethylpentyl)-1,5,6,7-tetrahydro-4H-indazol-4-one;
207. 1,3,6,6-tetramethyl-1,5,6,7-tetrahydro-4H-indazol-4-one;
208. 1-(2-hydroxyethyl)-3,6,6-trimethyl-1,5,6,7-tetrahydro-4H-indazol-4-one;
209. 3,6,6-trimethyl-1-phenyl-1,5,6,7-tetrahydro-4H-indazol-4-one;
210. 1-(6-chloro-3-pyridazinyl)-3,6,6-trimethyl-1,5,6,7-tetrahydro-4H-indazol-4-one;
211. 1-(3-methoxyphenyl)-3,6,6-trimethyl-1,5,6,7-tetrahydro-4H-indazol-4-one;
212. 1-(3-chlorophenyl)-3,6,6-trimethyl-1,5,6,7-tetrahydro-4H-indazol-4-one;
213. .1-(4-isopropylphenyl)-3,6,6-trimethyl-1,5,6,7-tetrahydro-4H-indazol-4-one;
214. 1-(4-iodophenyl)-3,6,6-trimethyl-1,5,6,7-tetrahydro-4H-indazol-4-one;
215. 3-cyclopropyl-1,6,6-trimethyl-1,5,6,7-tetrahydro-4H-indazol-4-one;
216. 3-cyclopropyl-1-(2-hydroxyethyl)-6,6-dimethyl-1,5,6,7-tetrahydro-4H-indazol-4-one;
217. 3-cyclopropyl-6,6-dimethyl-1-phenyl-1,5,6,7-tetrahydro-4H-indazol-4-one;
218. 3-cyclopropyl-6,6-dimethyl-1-(2-pyridinyl)-1,5,6,7-tetrahydro-4H-indazol-4-one;
219. 1-(6-chloro-3-pyridazinyl)-3-cyclopropyl-6,6-dimethyl-1,5,6,7-tetrahydro-4H-indazol-4-one;
220. 3-cyclopropyl-1-(3-methoxyphenyl)-6,6-dimethyl-1,5,6,7-tetrahydro-4H-indazol-4-one;
221. 1-(3-chlorophenyl)-3-cyclopropyl-6,6-dimethyl-1,5,6,7-tetrahydro-4H-indazol-4-one;
222. 3-cyclopropyl-1-(4-isopropylphenyl)-6,6-dimethyl-1,5,6,7-tetrahydro-4H-indazol-4-one;
223. 3-cyclopropyl-1-(4-iodophenyl)-6,6-dimethyl-1,5,6,7-tetrahydro-4H-indazol-4-one;
224. 3-isopropyl-1,6,6-trimethyl-1,5,6,7-tetrahydro-4H-indazol-4-one;
225. 1-(2-hydroxyethyl)-3-isopropyl-6,6-dimethyl-1,5,6,7-tetrahydro-4H-indazol-4-one;
226. 3-isopropyl-6,6-dimethyl-1-phenyl-1,5,6,7-tetrahydro-4H-indazol-4-one;
227. 3-isopropyl-6,6-dimethyl-1-(2-pyridinyl)-1,5,6,7-tetrahydro-4H-indazol-4-one;
228. 1-(6-chloro-3-pyridazinyl)-3-isopropyl-6,6-dimethyl-1,5,6,7-tetrahydro-4H-indazol-4-one;
229. 3-isopropyl-1-(3-methoxyphenyl)-6,6-dimethyl-1,5,6,7-tetrahydro-4H-indazol-4-one;
230. 1-(3-chlorophenyl)-3-isopropyl-6,6-dimethyl-1,5,6,7-tetrahydro-4H-indazol-4-one;
231. 3-isopropyl-1-(4-isopropylphenyl)-6,6-dimethyl-1,5,6,7-tetrahydro-4H-indazol-4-one;
232. 1-(4-iodophenyl)-3-isopropyl-6,6-dimethyl-1,5,6,7-tetrahydro-4H-indazol-4-one;
233. 1,6,6-trimethyl-3-propyl-1,5,6,7-tetrahydro-4H-indazol-4-one;
234. 1-(2-hydroxyethyl)-6,6-dimethyl-3-propyl-1,5,6,7-tetrahydro-4H-indazol-4-one;
235. 6,6-dimethyl-1-phenyl-3-propyl-1,5,6,7-tetrahydro-4H-indazol-4-one;
236. 6,6-dimethyl-3-propyl-1-(2-pyridinyl)-1,5,6,7-tetrahydro-4H-indazol-4-one
237. 1-(6-chloro-3-pyridazinyl)-6,6-dimethyl-3-propyl-1,5,6,7-tetrahydro-4H-indazol-4-one;
238. 1-(3-methoxyphenyl)-6,6-dimethyl-3-propyl-1,5,6,7-tetrahydro-4H-indazol-4-one;

239. 1-(3-chlorophenyl)-6,6-dimethyl-3-propyl-1,5,6,7-tetrahydro-4H-indazol-4-one;
240. 1-(4-isopropylphenyl)-6,6-dimethyl-3-propyl-1,5,6,7-tetrahydro-4H-indazol-4-one;
241. 1-(4-iodophenyl)-6,6-dimethyl-3-propyl-1,5,6,7-tetrahydro-4H-indazol-4-one;
242. 1,6,6-trimethyl-3-tertbuty-1-1,5,6,7-tetrahydro-4H-indazol-4-one;
243. 1-(2-hydroxyethyl)-6,6-dimethyl-3-tertbutyl-1,5,6,7-tetrahydro-4H-indazol-4-one;
244. 6,6-dimethyl-1-phenyl-3-tertbutyl-1,5,6,7-tetrahydro-4H-indazol-4-one;
245. 6,6-dimethyl-1-(2-pyridinyl)-3-tertbutyl-1,5,6,7-tetrahydro-4H-indazol-4-one;
246. 1-(6-chloro-3-pyridazinyl)-6,6-dimethyl-3-tertbutyl-1,5,6,7-tetrahydro-4H-indazol-4-one;
247. 1-(3-methoxyphenyl)-6,6-dimethyl-3-tertbutyl-1,5,6,7-tetrahydro-4H-indazol-4-one;
248. 1-(3-chlorophenyl)-6,6-dimethyl-3-tertbutyl-1,5,6,7-tetrahydro-4H-indazol-4-one;
249. 1-(4-isopropylphenyl)-6,6-dimethyl-3-tertbutyl-1-1,5,6,7-tetrahydro-4H-indazol-4-one;
250. 1-(4-iodophenyl)-6,6-dimethyl-3-tertbutyl-1,5,6,7-tetrahydro-4H-indazol-4-one;
251. 3-isobutyl-1,6,6-trimethyl-1,5,6,7-tetrahydro-4H-indazol-4-one;
252. 1-(2-hydroxyethyl)-3-isobutyl-6,6-dimethyl-1,5,6,7-tetrahydro-4H-indazol-4-one;
253. 3-isobutyl-6,6-dimethyl-1-phenyl-1,5,6,7-tetrahydro-4H-indazol-4-one;
254. 3-isobutyl-6,6-dimethyl-1-(2-pyridinyl)-1,5,6,7-tetrahydro-4H-indazol-4-one;
255. 1-(6-chloro-3-pyridazinyl)-3-isobutyl-6,6-dimethyl-1,5,6,7-tetrahydro-4H-indazol-4-one;
256. 3-isobutyl-1-(3-methoxyphenyl)-6,6-dimethyl-1,5,6,7-tetrahydro-4H-indazol-4-one;
257. 1-(3-chlorophenyl)-3-isobutyl-6,6-dimethyl-1,5,6,7-tetrahydro-4H-indazol-4-one;
258. 3-isobutyl-1-(4-isopropylphenyl)-6,6-dimethyl-1-1,5,6,7-tetrahydro-4H-indazol-4-one;
259. 1-(4-iodophenyl)-3-isobutyl-6,6-dimethyl-1,5,6,7-tetrahydro-4H-indazol-4-one;
260. 1,6,6-trimethyl-3-(2,4,4-trimethylpentyl)-1,5,6,7-tetrahydro-4H-indazol-4-one;
261. 1-(2-hydroxyethyl)-6,6-dimethyl-3-(2,4,4-trimethylpentyl)-1,5,6,7-tetrahydro-4H-indazol-4-one;
262. 6,6-dimethyl-1-phenyl-3-(2,4,4-trimethylpentyl)-1,5,6,7-tetrahydro-4H-indazol-4-one;
263. 6,6-dimethyl-3-(2,4,4-trimethylpentyl)-1-(2-pyridinyl)-1,5,6,7-tetrahydro-4H-indazol-4-one;
264. 1-(6-chloro-3-pyridazinyl)-6,6-dimethyl-3-(2,4,4-trimethylpentyl)-1,5,6,7-tetrahydro-4H-indazol-4-one;
265. 1-(3-methoxyphenyl)-6,6-dimethyl-3-(2,4,4-trimethylpentyl)-1,5,6,7-tetrahydro-4H-indazol-4-one;
266. 1-(3-chlorophenyl)-6,6-dimethyl-3-(2,4,4-trimethylpentyl)-1,5,6,7-tetrahydro-4H-indazol-4-one;
267. 1-(4-isopropylphenyl)-6,6-dimethyl-3-(2,4,4-trimethylpentyl)-1-1,5,6,7-tetrahydro-4H-indazol-4-one;
268. 1-(4-iodophenyl)-6,6-dimethyl-3-(2,4,4-trimethylpentyl)-1,5,6,7-tetrahydro-4H-indazol-4-one;
269. 3-cyclopropyl-1-(2-hydroxyethyl)-5,6-dihydrocyclopenta[c]pyrazol-4(1H)-one;
270. 3-(2-furyl)-1-(2-hydroxyethyl)-5,6-dihydrocyclopenta[c]pyrazol-4(1H)-one;
271. 3-(isoxazol-5-yl)-1-(2-hydroxyethyl)-5,6-dihydrocyclopenta[c]pyrazol-4(1H)-one;
272. 3-phenyl-1-(2-hydroxyethyl)-5,6-dihydrocyclopenta[c]pyrazol-4(1H)-one;
273. 3-(thien-2-yl)-1-(2-hydroxyethyl)-5,6-dihydrocyclopenta[c]pyrazol-4(1H)-one;
274. 3-benzyl-1-(2-hydroxyethyl)-5,6-dihydrocyclopenta[c]pyrazol-4(1H)-one;
275. 3-(2-fluorophenyl)-1-(2-hydroxyethyl)-5,6-dihydrocyclopenta[c]pyrazol-4(1H)-one;
276. 3-(2-thienylmethyl)-1-(2-hydroxyethyl)-5,6-dihydrocyclopenta[c]pyrazol-4(1H)-one;
277. 3-(2-cyclopentylethyl)-1-(2-hydroxyethyl)-5,6-dihydrocyclopenta[c]pyrazol-4(1H)-one;
278. 3-(3-methoxyphenyl)-1-(2-hydroxyethyl)-5,6-dihydrocyclopenta[c]pyrazol-4(1H)-one;
279. 3-phenoxymethyl-1-2-(hydroxyethyl)-5,6-dihydrocyclopenta[c]pyrazol-4(1H)-one;
280. 3-(pyrid-4-yl)-1-(2-hydroxyethyl)-5,6-dihydrocyclopenta[c]pyrazol-4(1H)-one;
281. 3-(trans-2-phenyl-cycloprop-1-yl)-1-2-(hydroxyethyl)-5,6-dihydrocyclopenta[c]pyrazol-4(1H)-one;
282. 3-(4-dimethylaminophenyl)-1-(2-hydroxyethyl)-5,6-dihydrocyclopenta[c]pyrazol-4(1H)-one;
283. 3-(quinoxal-2-yl)-1-(2-hydroxyethyl)-5,6-dihydrocyclopenta[c]pyrazol-4(1H)-one;
284. 3-(2,6-dimethoxyphenyl)-1-(2-hydroxyethyl)-5,6-dihydrocyclopenta[c]pyrazol-4(1H)-one;
285. 3-cyclopropyl1-(2-cyanoethyl)-5,6-dihydrocyclopenta[c]pyrazol-4(1H)-one;
286. 3-(2-furyl)-1-(2-cyanoethyl)-5,6-dihydrocyclopenta[c]pyrazol-4(1H)-one;
287. 3-(isoxazol-5-yl)-1-(2-cyanoethyl)-5,6-dihydrocyclopenta[c]pyrazol-4(1H)-one;
288. 3-phenyl-1-(2-cyanoethyl))-5,6-dihydrocyclopenta[c]pyrazol-4(1H)-one;
289. 3-(thien-2-yl)-1-(2-cyanoethyl)-5,6-dihydrocyclopenta[c]pyrazol-4(1H)-one;
290. 3-benzyl-1-(2-cyanoethyl)-5,6-dihydrocyclopenta[c]pyrazol-4(1H)-one;
291. 3-(2-fluorophenyl)-1-(2-cyanoethyl)-5,6-dihydrocyclopenta[c]pyrazol-4(1H)-one;
292. 3-(2-thienylmethyl)-1-(2-cyanoethyl)-5,6-dihydrocyclopenta[c]pyrazol-4(1H)-one;
293. 3-(2-cyclopentylethyl)-1-(2-cyanoethyl)-5,6-dihydrocyclopenta[c]pyrazol-4(1H)-one;
294. 3-(3-methoxyphenyl)-1-(2-cyanoethyl)-5,6-dihydrocyclopenta[c]pyrazol-4(1H)-one;
295. 3-phenoxymethyl-1-(2-cyanoethyl)-5,6-dihydrocyclopenta[c]pyrazol-4(1H)-one;
296. 3-(pyrid-4-yl)-1-(2-cyanoethyl)-5,6-dihydrocyclopenta[c]pyrazol-4(1H)-one;
297. 3-(trans-2-phenyl-cycloprop-1-yl)-1-(2-cyanoethyl)-5,6-dihydrocyclopenta[c]pyrazol-4(1H)-one;
298. 3-(4-dimethylaminophenyl)-1-(2-cyanoethyl)-5,6-dihydrocyclopenta[c]pyrazol-4(1H)-one;
299. 3-(quinoxal-2-yl)-1-(2-cyanoethyl)-5,6-dihydrocyclopenta[c]pyrazol-4(1H)-one;
300. 3-(2,6-dimethoxyphenyl)-1-(2-cyanoethyl)-5,6-dihydrocyclopenta[c]pyrazol-4(1H)-one;

301. 3-cyclopropyl1-7,7-dimethyl-(2,2,2-trifluoroethyl)-1,5,6,7-tetrahydro-4H-indazol-4-one;
302. 7,7-dimethyl-3-(2-furyl)-1-(2,2,2-trifluoroethyl)-1,5,6,7-tetrahydro-4H-indazol-4-one;
303. 7,7-dimethyl-3-(isoxazol-5-yl)-1-(2,2,2-trifluoroethyl)-1,5,6,7-tetrahydro-4H-indazol-4-one;
304. 7,7-dimethyl-3-phenyl-1-(2,2,2-trifluoroethyl)-1,5,6,7-tetrahydro-4H-indazol-4-one;
305. 7,7-dimethyl-3-(thien-2-yl)-1-(2,2,2-trifluoroethyl)-1,5,6,7-tetrahydro-4H-indazol-4-one;
306. 3-benzyl-7,7-dimethyl-1-(2,2,2-trifluoroethyl)-1,5,6,7-tetrahydro-4H-indazol-4-one;
307. 7,7-dimethyl-3-(2-fluorophenyl)-1-(2,2,2-trifluoroethyl)-1,5,6,7-tetrahydro-4H-indazol-4-one;
308. 7,7-dimethyl-3-(2-thienylmethyl)-1-(2,2,2-trifluoroethyl)-1,5,6,7-tetrahydro-4H-indazol-4-one;
309. 3-(2-cyclopentylethyl)-7,7-dimethyl-1-(2,2,2-trifluoroethyl)-1,5,6,7-tetrahydro-4H-indazol-4-one;
310. 7,7-dimethyl-3-(3-methoxyphenyl)-1-(2,2,2-trifluoroethyl)-1,5,6,7-tetrahydro-4H-indazol-4-one;
311. 7,7-dimethyl-3-phenoxymethyl-1-(2,2,2-trifluoroethyl)-1,5,6,7-tetrahydro-4H-indazol-4-one;
312. 7,7-dimethyl-3-(pyrid-4-yl)-1-(2,2,2-trifluoroethyl)-1,5,6,7-tetrahydro-4H-indazol-4-one;
313. 7,7-dimethyl-3-(trans-2-phenyl-cycloprop-1-yl)-1-(2,2,2-trifluoroethyl)-1,5,6,7-tetrahydro-4H-indazol-4-one;
314. 7,7-dimethyl-3-(4-dimethylaminophenyl)-1-(2,2,2-trifluoroethyl)-1,5,6,7-tetrahydro-4H-indazol-4-one;
315. 7,7-dimethyl-3-(quinoxal-2-yl)-1-(2,2,2-trifluoroethyl)-1,5,6,7-tetrahydro-4H-indazol-4-one;
316. 7,7-dimethyl-3-(2,6-dimethoxyphenyl)-1-(2,2,2-trifluoroethyl)-1,5,6,7-tetrahydro-4H-indazol-4-one;
317. 3-cyclopropyl1-5,5-dimethyl-(2,2,2-trifluoroethyl)-1,5,6,7-tetrahydro-4H-indazol-4-one;
318. 5,5-dimethyl-3-(2-furyl)-1-(2,2,2-trifluoroethyl)-1,5,6,7-tetrahydro-4H-indazol-4-one;
319. 5,5-dimethyl-3-(isoxazol-5-yl)-1-(2,2,2-trifluoroethyl)-1,5,6,7-tetrahydro-4H-indazol-4-one;
320. 5,5-dimethyl-3-phenyl-1-(2,2,2-trifluoroethyl)-1,5,6,7-tetrahydro-4H-indazol-4-one;
321. 5,5-dimethyl-3-(thien-2-yl)-1-(2,2,2-trifluoroethyl)-1,5,6,7-tetrahydro-4H-indazol-4-one;
322. 3-benzyl-5,5-dimethyl-1-(2,2,2-trifluoroethyl)-1,5,6,7-tetrahydro-4H-indazol-4-one;
323. 5,5-dimethyl-3-(2-fluorophenyl)-1-(2,2,2-trifluoroethyl)-1,5,6,7-tetrahydro-4H-indazol-4-one;
324. 5,5-dimethyl-3-(2-thienylmethyl)-1-(2,2,2-trifluoroethyl)-1,5,6,7-tetrahydro-4H-indazol-4-one;
325. 3-(2-cyclopentylethyl)-5,5-dimethyl-1-(2,2,2-trifluoroethyl)-1,5,6,7-tetrahydro-4H-indazol-4-one;
326. 5,5-dimethyl-3-(3-methoxyphenyl)-1-(2,2,2-trifluoroethyl)-1,5,6,7-tetrahydro-4H-indazol-4-one;
327. 5,5-dimethyl-3-phenoxymethyl-1-(2,2,2-trifluoroethyl)-1,5,6,7-tetrahydro-4H-indazol-4-one;
328. 5,5-dimethyl-3-(pyrid-4-yl)-1-(2,2,2-trifluoroethyl)-1,5,6,7-tetrahydro-4H-indazol-4-one;
329. 5,5-dimethyl-3-(trans-2-phenyl-cycloprop-1-yl)-1-(2,2,2-trifluoroethyl)-1,5,6,7-tetrahydro-4H-indazol-4-one; 330. 5,5-dimethyl-3-(4-dimethylaminophenyl)-1-(2,2,2-trifluoroethyl)-1,5,6,7-tetrahydro-4H-indazol-4-one;
331. 5,5-dimethyl-3-(quinoxal-2-yl)-1-(2,2,2-trifluoroethyl)-1,5,6,7-tetrahydro-4H-indazol-4-one;
332. 5,5-dimethyl-3-(2,6-dimethoxyphenyl)-1-(2,2,2-trifluoroethyl)-1,5,6,7-tetrahydro-4H-indazol-4-one;
333. 1-(3-chloropyridazin-6-yl)-3-cyclopropyl1-7,7-dimethyl-1,5,6,7-tetrahydro-4H-indazol-4-one;
334. 1-(3-chloropyridazin-6-yl)-7,7-dimethyl-3-(2-furyl)-1,5,6,7-tetrahydro-4H-indazol-4-one;
335. 1-(3-chloropyridazin-6-yl)-7,7-dimethyl-3-(isoxazol-5-yl)-1,5,6,7-tetrahydro-4H-indazol-4-one;
336. 1-(3-chloropyridazin-6-yl)-7,7-dimethyl-3-phenyl-1,5,6,7-tetrahydro-4H-indazol-4-one;
337. 1-(3-chloropyridazin-6-yl)-7,7-dimethyl-3-(thien-2-yl)-1,5,6,7-tetrahydro-4H-indazol-4-one;
338. 3-benzyl-1-(3-chloropyridazin-6-yl)-7,7-dimethyl-1,5,6,7-tetrahydro-4H-indazol-4-one;
339. 1-(3-chloropyridazin-6-yl)-7,7-dimethyl-3-(2-fluorophenyl)-1,5,6,7-tetrahydro-4H-indazol-4-one;
340. 1-(3-chloropyridazin-6-yl)-7,7-dimethyl-3-(2-thienylmethyl)-1,5,6,7-tetrahydro-4H-indazol-4-one;
341. 1-(3-chloropyridazin-6-yl)-3-(2-cyclopentylethyl)-7,7-dimethyl-1,5,6,7-tetrahydro-4H-indazol-4-one;
342. 1-(3-chloropyridazin-6-yl)-7,7-dimethyl-3-(3-methoxyphenyl)-1,5,6,7-tetrahydro-4H-indazol-4-one;
343. 1-(3-chloropyridazin-6-yl)-7,7-dimethyl-3-phenoxymethyl-1,5,6,7-tetrahydro-4H-indazol-4-one;
344. 1-(3-chloropyridazin-6-yl)-7,7-dimethyl-3-(pyrid-4-yl)-1,5,6,7-tetrahydro-4H-indazol-4-one;
345. 1-(3-chloropyridazin-6-yl)-7,7-dimethyl-3-(trans-2-phenyl-cycloprop-1-yl)-1,5,6,7-tetrahydro-4H-indazol-4-one;
346. 1-(3-chloropyridazin-6-yl)-7,7-dimethyl-3-(4-dimethylaminophenyl)-1,5,6,7-tetrahydro-4H-indazol-4one;
347. 1-(3-chloropyridazin-6-yl)-7,7-dimethyl-3-(quinoxal-2-yl)-1,5,6,7-tetrahydro-4H-indazol-4-one;
348. 1-(3-chloropyridazin-6-yl)-7,7-dimethyl-3-(2,6-dimethoxyphenyl)-1,5,6,7-tetrahydro-4H-indazol-4-one;
349. 1-(3-chloropyridazin-6-yl)-3-cyclopropyl1-5,5-dimethyl-1,5,6,7-tetrahydro-4H-indazol-4-one;
350. 1-(3-chloropyridazin-6-yl)-5,5-dimethyl-3-(2-furyl)-1,5,6,7-tetrahydro-4H-indazol-4-one;
351. 1-(3-chloropyridazin-6-yl)-5,5-dimethyl-3-(isoxazol-5-yl)-1,5,6,7-tetrahydro-4H-indazol-4-one;
352. 1-(3-chloropyridazin-6-yl)-5,5-dimethyl-3-phenyl-1,5,6,7-tetrahydro-4H-indazol-4-one;
353. 1-(3-chloropyridazin-6-yl)-5,5-dimethyl-3-(thien-2-yl)-1,5,6,7-tetrahydro-4H-indazol-4-one;
354. 3-benzyl-1-(3-chloropyridazin-6-yl)-5,5-dimethyl-1,5,6,7-tetrahydro-4H-indazol-4-one;
355. 1-(3-chloropyridazin-6-yl)-5,5-dimethyl-3-(2-fluorophenyl)-1,5,6,7-tetrahydro-4H-indazol-4-one;
356. 1-(3-chloropyridazin-6-yl)-5,5-dimethyl-3-(2-thienylmethyl)-1,5,6,7-tetrahydro-4H-indazol-4-one;
357. 1-(3-chloropyridazin-6-yl)-3-(2-cyclopentylethyl)-5,5-dimethyl-1,5,6,7-tetrahydro-4H-indazol-4-one;
358. 1-(3-chloropyridazin-6-yl)-5,5-dimethyl-3-(3-methoxyphenyl)-1,5,6,7-tetrahydro-4H-indazol-4-one;
359. 1-(3-chloropyridazin-6-yl)-5,5-dimethyl-3-phenoxymethyl-1,5,6,7-tetrahydro-4H-indazol-4-one;
360. 1-(3-chloropyridazin-6-yl)-5,5-dimethyl-3-(pyrid-4-yl)-1,5,6,7-tetrahydro-4H-indazol-4-one;

361. 1-(3-chloropyridazin-6-yl)-5,5-dimethyl-3-(trans-2-phenyl-cycloprop-1-yl)-1,5,6,7-tetrahydro-4H-indazol-4-one;
362. 1-(3-chloropyridazin-6yl)-5,5-dimethyl-3-(4-dimethylaminophenyl)-1,5,6,7-tetrahydro-4H-indazol-4-one;
363. 1-(3-chloropyridazin-6-yl)-5,5-dimethyl-3-(quinoxal-2-yl)-1,5,6,7-tetrahydro-4H-indazol-4-one;
364. 1-(3-chloropyridazin-6-yl)-5,5-dimethyl-3-(2,6-dimethoxyphenyl)-1,5,6,7-tetrahydro-4H-indazol-4-one;
365. 1-(benzothiazol-2-yl)-7-cyano-3-cyclopropyl1-6,6-dimethyl-1,5,6,7-tetrahydro-4H-indazol-4-one;
366. 1-(benzothiazol-2-yl)-7-cyano-6,6-dimethyl-3-(2-furyl)-1,5,6,7-tetrahydro-4H-indazol-4-one;
367. 1-(benzothiazol-2-yl)-7-cyano-6,6-dimethyl-3-(isoxazol-5-yl)-1,5,6,7-tetrahydro-4H-indazol-4-one;
368. 1-(benzothiazol-2-yl)-7-cyano-6,6-dimethyl-3-phenyl-1,5,6,7-tetrahydro-4H-indazol-4-one;
369. 1-(benzothiazol-2-yl)-7-cyano-6,6-dimethyl-3-(thien-2-yl)-1,5,6,7-tetrahydro-4H-indazol-4-one;
370. 1-(benzothiazol-2-yl)-3-benzyl-7-cyano-6,6-dimethyl-1,5,6,7-tetrahydro-4H-indazol-4-one;
371. 1-(benzothiazol-2-yl)-7-cyano-6,6-dimethyl-3-(2-fluorophenyl)-1,5,6,7-tetrahydro-4H-indazol-4-one;
372. 1-(benzothiazol-2-yl)-7-cyano-6,6-dimethyl-3-(2-thienylmethyl)-1,5,6,7-tetrahydro-4H-indazol-4-one;
373. 1-(benzothiazol-2yl)-7-cyano-3-(2-cyclopentylethyl)-6,6-dimethyl-1,5,6,7-tetrahydro-4H-indazol-4-one;
374. 1-(benzothiazol-2-yl)-7-cyano-6,6-dimethyl-3-(3-methoxyphenyl)-1,5,6,7-tetrahydro-4H-indazol-4-one;
375. 1-(benzothiazol-2-yl)-7-cyano-6,6-dimethyl-3-phenoxymethyl-1,5,6,7-tetrahydro-4H-indazol-4-one;
376. 1-(benzothiazol-2-yl)-7-cyano-6,6-dimethyl-3-(pyrid-4-yl)-1,5,6,7-tetrahydro-4H-indazol-4-one;
377. 1-(benzothiazol-2-yl)-7-cyano-6,6-dimethyl-3-(trans-2-phenyl-cycloprop-1-yl)-1,5,6,7-tetrahydro-4H-indazol-4-one;
378. 1-(benzothiazol-2-yl)-7-cyano-6,6-dimethyl-3-(4-dimethylaminophenyl)-1,5,6,7-tetrahydro-4H-indazol-4-one;
379. 1-(benzothiazol-2-yl)-7-cyano-6,6-dimethyl-3-(quinoxal-2-yl)-1,5,6,7-tetrahydro-4H-indazol-4-one;
380. 1-(benzothiazol-2-yl)-7-cyano-6,6-dimethyl-3-(2,6-dimethoxyphenyl)-1,5,6,7-tetrahydro-4H-indazol-4-one;
381. 1-(benzothiazol-2-yl)-5-cyano-3-cyclopropyl1-6,6-dimethyl-1,5,6,7-tetrahydro-4H-indazol-4-one;
382. 1-(benzothiazol-2-yl)-5-cyano-6,6-dimethyl-3-(2-furyl)-1,5,6,7-tetrahydro-4H-indazol-4-one;
383. 1-(benzothiazol-2-yl)-5-cyano-6,6-dimethyl-3-(isoxazol-5-yl)-1,5,6,7-tetrahydro-4H-indazol-4-one;
384. 1-(benzothiazol-2-yl)-5-cyano-6,6-dimethyl-3-phenyl-1,5,6,7-tetrahydro-4H-indazol-4-one;
385. 1-(benzothiazol-2-yl)-5-cyano-6,6-dimethyl-3-(thien-2-yl)-1,5,6,7-tetrahydro-4H-indazol-4-one;
386. 1-(benzothiazol-2-yl)-3-benzyl-5-cyano-6,6-dimethyl-1,5,6,7-tetrahydro-4H-indazol-4-one;
387. 1-(benzothiazol-2-yl)-5-cyano-6,6-dimethyl-3-(2-fluorophenyl)-1,5,6,7-tetrahydro-4H-indazol-4-one;
388. 1-(benzothiazol-2-yl)-5-cyano-6,6-dimethyl-3-(2-thienylmethyl)-1,5,6,7-tetrahydro-4H-indazol-4-one;
389. 1-(benzothiazol-2yl)-5-cyano-3-(2-cyclopentylethyl)-6,6-dimethyl-1,5,6,7-tetrahydro-4H-indazol-4-one;
390. 1-(benzothiazol-2-yl)-5-cyano-6,6-dimethyl-3-(3-methoxyphenyl)-1,5,6,7-tetrahydro-4H-indazol-4-one;
391. 1-(benzothiazol-2-yl)-5-cyano-6,6-dimethyl-3-phenoxymethyl-1,5,6,7-tetrahydro-4H-indazol-4-one;
392. 1-(benzothiazol-2-yl)-5-cyano-6,6-dimethyl-3-(pyrid-4-yl)-1,5,6,7-tetrahydro-4H-indazol-4-one;
393. 1-(benzothiazol-2-yl)-5-cyano-6,6-dimethyl-3-(trans-2-phenyl-cycloprop-1-yl)-1,5,6,7-tetrahydro-4H-indazol-4-one;
394. 1-(benzothiazol-2-yl)-5-cyano-6,6-dimethyl-3-(4-dimethylaminophenyl)-1,5,6,7-tetrahydro-4H-indazol-4-30 one;
395. 1-(benzothiazol-2-yl)-5-cyano-6,6-dimethyl-3-(quinoxal-2-yl)-1,5,6,7-tetrahydro-4H-indazol-4-one;
396. 1-(benzothiazol-2-yl)-5-cyano-6,6-dimethyl-3-(2,6-dimethoxyphenyl)-1,5,6,7-tetrahydro-4H-indazol-4-one;
397. 7-cyano-3-cyclopropyl1-6,6-dimethyl-1-(4-isopropylphenyl)-1,5,6,7-tetrahydro-4H-indazol-4-one;
398. 7-cyano-6,6-dimethyl-3-(2-furyl)-1-(4-isopropylphenyl)-1,5,6,7-tetrahydro-4H-indazol-4-one;
399. 7-cyano-6,6-dimethyl-1-(4-isopropylphenyl)-3-(isoxazol-5-yl)-1,5,6,7-tetrahydro-4H-indazol-4-one;
400. 7-cyano-6,6-dimethyl-1-(4-isopropylphenyl)-3-phenyl-1,5,6,7-tetrahydro-4H-indazol-4-one;
401. 7-cyano-6,6-dimethyl-1-(4-isopropylphenyl)-3-(thien-2-yl)-1,5,6,7-tetrahydro-4H-indazol-4-one;
402. 3-benzyl-7-cyano-6,6-dimethyl-1-(4-isopropylphenyl)-1,5,6,7-tetrahydro-4H-indazol-4-one;
403. 7-cyano-6,6-dimethyl-3-(2-fluorophenyl)-1-(4-isopropylphenyl)-1,5,6,7-tetrahydro-4H-indazol-4-one;
404. 7-cyano-6,6-dimethyl-1-(4-isopropylphenyl)-3-(2-thienylmethyl)-1,5,6,7-tetrahydro-4H-indazol-4-one;
405. 7-cyano-3-(2-cyclopentylethyl)-6,6-dimethyl-1-(4-isopropylphenyl)-1,5,6,7-tetrahydro-4H-indazol-4one;
406. 7-cyano-6,6-dimethyl-1-(4-isopropylphenyl)-3-(3-methoxyphenyl)-1,5,6,7-tetrahydro-4H-indazol-4-one;
407. 7-cyano-6,6-dimethyl-1-(4-isopropylphenyl)-3-phenoxymethyl-1,5,6,7-tetrahydro-4H-indazol-4-one;
408. 7-cyano-6,6-dimethyl-1-(4-isopropylphenyl)-3-(pyrid-4-yl)-1,5,6,7-tetrahydro-4H-indazol-4-one;
409. 7-cyano-6,6-dimethyl-1-(4-isopropylphenyl)-3-(trans-2-phenyl-cycloprop-1-yl)-1,5,6,7-tetrahydro-4H-indazol-4-one;
410. 7-cyano-6,6-dimethyl-3-(4-dimethylaminophenyl)-1-(4-isopropylphenyl)-1,5,6,7-tetrahydro-4H-indazol-4-one;
411. 7-cyano-6,6-dimethyl-1-(4-isopropylphenyl)-3-(quinoxal-2-yl)-1,5,6,7-tetrahydro-4H-indazol-4-one;
412. 7-cyano-6,6-dimethyl-3-(2,6-dimethoxyphenyl)-1-(4-isopropylphenyl)-1,5,6,7-tetrahydro-4H-indazol-4-one;
413. 5-cyano-3-cyclopropyl1-6,6-dimethyl-1-(4-isopropylphenyl)-1,5,6,7-tetrahydro-4H-indazol-4-one;
414. 5-cyano-6,6-dimethyl-3-(2-furyl)-1-(4-isopropylphenyl)-1,5,6,7-tetrahydro-4H-indazol-4-one;

415. 5-cyano-6,6-dimethyl-1-(4-isopropylphenyl)-3-(isoxazol-5-yl)-1,5,6,7-tetrahydro-4H-indazol-4-one;
416. 5-cyano-6,6-dimethyl-1-(4-isopropylphenyl)-3-phenyl-1,5,6,7-tetrahydro-4H-indazol-4-one;
417. 5-cyano-6,6-dimethyl-1-(4-isopropylphenyl)-3-(thien-2-yl)-1,5,6,7-tetrahydro-4H-indazol-4-one;
418. 3-benzyl-5-cyano-6,6-dimethyl-1-(4-isopropylphenyl)-1,5,6,7-tetrahydro-4H-indazol-4-one;
419. 5-cyano-6,6-dimethyl-3-(2-fluorophenyl)-1-(4-isopropylphenyl)-1,5,6,7-tetrahydro-4H-indazol-4-one;
420. 5-cyano-6,6-dimethyl-1-(4-isopropylphenyl)-3-(2-thienylmethyl)-1,5,6,7-tetrahydro-4H-indazol-4-one;
421. 5-cyano-3-(2-cyclopentylethyl)-6,6-dimethyl-1-(4-isopropylphenyl)-1,5,6,7-tetrahydro-4H-indazol-4one;
422. 5-cyano-6,6-dimethyl-1-(4-isopropylphenyl)-3-(3-methoxyphenyl)-1,5,6,7-tetrahydro-4H-indazol-4-one;
423. 5-cyano-6,6-dimethyl-1-(4-isopropylphenyl)-3-phenoxymethyl-1,5,6,7-tetrahydro-4H-indazol-4-one;
424. 5-cyano-6,6-dimethyl-1-(4-isopropylphenyl)-3-(pyrid-4-yl)-1,5,6,7-tetrahydro-4H-indazol-4-one;
425. 5-cyano-6,6-dimethyl-1-(4-isopropylphenyl)-3-(trans-2-phenyl-cycloprop-1-yl)-1,5,6,7-tetrahydro-4H-indazol-4-one;
426. 5-cyano-6,6-dimethyl-3-(4-dimethylaminophenyl)-1-(4-isopropylphenyl)-1,5,6,7-tetrahydro-4H-indazol-4-one;
427. 5-cyano-6,6-dimethyl-1-(4-isopropylphenyl)-3-(quinoxal-2-yl)-1,5,6,7-tetrahydro-4H-indazol-4-one;
428. 5-cyano-6,6-dimethyl-3-(2,6-dimethoxyphenyl)-1-(4-isopropylphenyl)-1,5,6,7-tetrahydro-4H-indazol-4-one;
429. 3-cyclopropyl1-1-(4-iodophenyl)-8-methyl-1,5,5a,6,7,8,9,9a-octahydro-4H-pyrazolo[4,3-h]isoquinolin-4-one;
430. 3-(2-furyl)-1-(4-iodophenyl)-8-methyl-1,5,5a,6,7,8,9,9a-octahydro-4H-pyrazolo[4,3-h]isoquinolin-4-one;
431. 1-(4-iodophenyl)-3-(isoxazol-5-yl)-8-methyl-1,5,5a,6,7,8,9,9a-octahydro-4H-pyrazolo[4,3-h]isoquinolin-4-one;
432. 1-(4-iodophenyl)-8-methyl-3-phenyl-1,5,5a,6,7,8,9,9a-octahydro-4H-pyrazolo[4,3-h]isoquinolin-4-one;
433. 1-(4-iodophenyl)-8-methyl-3-(thien-2-yl)-1,5,5a,6,7,8,9,9a-octahydro-4H-pyrazolo[4,3-h]isoquinolin-4-one;
434. 3-benzyl-1-(4-iodophenyl)-8-methyl-1,5,5a,6,7,8,9,9a-octahydro-4H-pyrazolo[4,3-h]isoquinolin-4-one;
435. 3-(2-fluorophenyl)-1-(4-iodophenyl)-8-methyl-1,5,5a,6,7,8,9,9a-octahydro-4H-pyrazolo[4,3-h]isoquinolin-4-one;
436. 1-(4-iodophenyl)-8-methyl-3-(2-thienylmethyl)-1,5,5a,6,7,8,9,9a-octahydro-4H-pyrazolo[4,3-h]isoquinolin-4-one;
437. 3-(2-cyclopentylethyl)-1-(4-iodophenyl)-8-methyl-1,5,5a,6,7,8,9,9a-octahydro-4H-pyrazolo[4,3-h]isoquinolin-4-one;
438. 1-(4-iodophenyl)-3-(3-methoxyphenyl)-8-methyl-1,5,5a,6,7,8,9,9a-octahydro-4H-pyrazolo[4,3-h]isoquinolin-4-one;
439. 1-(4-iodophenyl)-8-methyl-3-phenoxymethyl-1,5,5a,6,7,8,9,9a-octahydro-4H-pyrazolo[4,3-h]isoquinolin-4-one;
440. 1-(4-iodophenyl)-8-methyl-3-(pyrid-4-yl)-1,5,5a,6,7,8,9,9a-octahydro-4H-pyrazolo[4,3-h]isoquinolin-4-one;
441. 1-(4-iodophenyl)-8-methyl-3-(trans-2-phenylcycloprop-1-yl)-1,5,5a,6,7,8,9,9a-octahydro-4H-pyrazolo[4,3-h]isoquinolin-4-one;
442. 3-(4-dimethylaminophenyl)-1-(4-iodophenyl)-8-methyl-1,5,5a,6,7,8,9,9a-octahydro-4H-pyrazolo[4,3-h]isoquinolin-4-one;
443. 1-(4-iodophenyl)-8-methyl-3-(quinoxal-2-yl)-1,5,5a,6,7,8,9,9a-octahydro-4H-pyrazolo[4,3-h]isoquinolin-4-one;
444. 3-(2,6-dimethoxyphenyl)-1-(4-iodophenyl)-8-methyl-1,5,5a,6,7,8,9,9a-octahydro-4H-pyrazolo[4,3-h]isoquinolin-4-one;
445. 3-cyclopropyl-1-(4-iodophenyl)-6-methyl-1,4a,5,6,7,8,8a,9-octahydro-4H-pyrazolo[3,4-g]isoquinolin-4-one;
446. 3-(2-furyl)-1-(4-iodophenyl)-6-methyl-1,4a,5,6,7,8,8a,9-octahydro-4H-pyrazolo[3,4-g]isoquinolin-4one;
447. 1-(4-iodophenyl)-3-(isoxazol-5-yl)-6-methyl-1,4a,5,6,7,8,8a,9-octahydro-4H-pyrazolo[3,4-g]isoquinolin-4-one;
448. 1-(4-iodophenyl)-6-methyl-3-phenyl-1,4a,5,6,7,8,8a,9-octahydro-4H-pyrazolo[3,4-g]isoquinolin-4-one;
449. 1-(4-iodophenyl)-6-methyl-3-(thien-2-yl)-1,4a,5,6,7,8,8a,9-octahydro-4H-pyrazolo[3,4-g]isoquinolin-4-one;
450. 3-benzyl-1-(4-iodophenyl)-6-methyl-1,4a,5,6,7,8,8a,9-octahydro-4H-pyrazolo[3,4-g]isoquinolin-4-one;
451. 3-(2-fluorophenyl)-1-(4-iodophenyl)-6-methyl-1,4a,5,6,7,8,8a,9-octahydro-4H-pyrazolo[3,4-g]isoquinolin-4-one;
452. 1-(4-iodophenyl)-6-methyl-3-(2-thienylmethyl)-1,4a,5,6,7,8,8a,9-octahydro-4H-pyrazolo[3,4-g]isoquinolin-4-one;
453. 3-(2-cyclopentylethyl)-1-(4-iodophenyl)-6-methyl-1,4a,5,6,7,8,8a,9-octahydro-4H-pyrazolo[3,4-g]isoquinolin-4-one;
454. 1-(4-iodophenyl)-3-(3-methoxyphenyl)-6-methyl-1,4a,5,6,7,8,8a,9-octahydro-4H-pyrazolo[3,4-g]isoquinolin-4-one;
455. 1-(4-iodophenyl)-6-methyl-3-phenoxymethyl-1,4a,5,6,7,8,8a,9-octahydro-4H-pyrazolo[3,4-g]isoquinolin-4-one;
456. 1-(4-iodophenyl)-6-methyl-3-(pyrid-4-yl)-1,4a,5,6,7,8,8a,9-octahydro-4H-pyrazolo[3,4-g]isoquinolin-4-one;
457. 1-(4-iodophenyl)-6-methyl-3-(trans-2-phenylcycloprop-1-yl)-1,4a,5,6,7,8,8a,9-octahydro-4H-pyrazolo[3,4-g]isoquinolin-4-one;
458. 3-(4-dimethylaminophenyl)-1-(4-iodophenyl)-6-methyl-1,4a,5,6,7,8,8a,9-octahydro-4H-pyrazolo[3,4-g]isoquinolin-4-one;
459. 1-(4-iodophenyl)-6-methyl-3-(quinoxal-2-yl)-1,4a,5,6,7,8,8a,9-octahydro-4H-pyrazolo[3,4-g]isoquinolin-4-one;
460. 3-(2,6-dimethoxyphenyl)-1-(4-iodophenyl)-6-methyl-1,4a,5,6,7,8,8a,9-octahydro-4H-pyrazolo[3,4-g]isoquinolin-4-one;
461. 1-(7-chloro-quinolin-4-yl)-3-cyclopropyl-indeno[1,2-c]pyrazol-4(1H)-one;
462. 1-(7-chloro-quinolin-4-yl)-3-(2-furyl)-indeno[1,2-c]pyrazol-4(1H)-one;

463. 1-(7-chloro-quinolin-4-yl)-3-(isoxazol-5-yl)-indeno[1,2-c]pyrazol-4(1H)-one;
464. 1-(7-chloro-quinolin-4-yl)-3-phenyl-indeno[1,2-c]pyrazol-4(1H)-one;
465. 1-(7-chloro-quinolin-4-yl)-3-(thien-2-yl)-indeno[1,2-c]pyrazol-4(1H)-one;
466. 3-benzyl-1-(7-chloro-quinolin-4-yl)-indeno[1,2-c]pyrazol-4(1H)-one;
467. 1-(7-chloro-quinolin-4-yl)-3-(2-fluorophenyl)-indeno[1,2-c]pyrazol-4(1H)-one;
468. 1-(7-chloro-quinolin-4-yl)-3-(2-thienylmethyl)-indeno[1,2-c]pyrazol-4(1H)-one;
469. 1-(7-chloro-quinolin-4-yl)-3-(2-cyclopentylethyl)indeno[1,2-c]pyrazol-4(1H)-one;
470. 1-(7-chloro-quinolin-4-yl)-3-(3-methoxyphenyl)indeno[1,2-c]pyrazol-4(1H)-one;
471. 1-(7-chloro-quinolin-4-yl)-3-phenoxymethylindeno[1,2-c]pyrazol-4(1H)-one
472. 1-(7-chloro-quinolin-4-yl)-3-(pyrid-4-yl)-indeno[1,2-c]pyrazol-4(1H)-one;
473. 1-(7-chloro-quinolin-4-yl)-3-(trans-2-phenylcycloprop-1-yl)-indeno[1,2-c]pyrazol-4(1H)-one;
474. 1-(7-chloro-quinolin-4-yl)-3-(4-dimethylaminophenyl)indeno[1,2-c]pyrazol-4(1H)-one;
475. 1-(7-chloro-quinolin-4-yl)-3-(quinoxal-2-yl)-indeno[1,2-c]pyrazol-4(1H)-one; and
476. 1-(7-chloro-quinolin-4-yl)-3-(2,6-dimethoxyphenyl)indeno[1,2-c]pyrazol-4(1H)-one.

Several other specific compounds of formula (I), object of the present invention and herewith intended as preferred compounds, are reported below in the working examples.

The compounds of formula (I) object of the present invention and the salts thereof can be obtained, for instance, by a process comprising:

a) when (x) is a double bond and $R_3$ is oxygen, reacting a compound of formula (II) or a polymer supported analogue thereof (IIa)

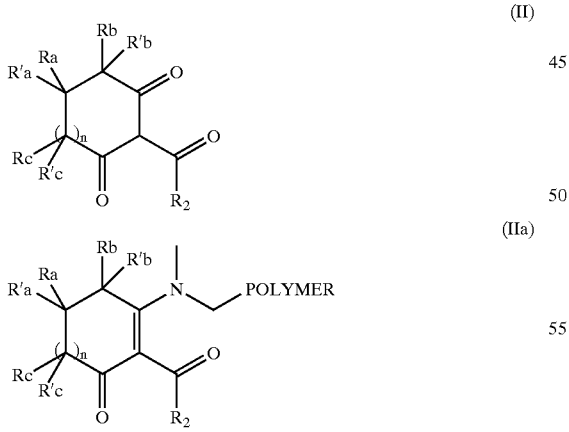

(II)

(IIa)

wherein n, $R_2$, Ra, R'a, Rb, R'b, Rc and R'c have the above reported meanings, with a substituted hydrazine of formula

  (III)

wherein $R_1$ has the above reported meanings, thus obtaining the corresponding compound of formula

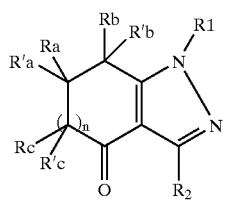

(Ia)

wherein n, $R_1$, $R_2$, Ra, R'a, Rb, R'b, Rc and R'c are as defined above; and, optionally, converting a compound of formula (Ia) into another compound of formula (I) or into a salt thereof by:

i) reacting the compound of formula (Ia), wherein n, $R_1$, $R_2$, Ra, R'a, R'b, Rc and R'c are as defined above and Rb is hydrogen with a suitable halogenating agent so as to obtain a compound of formula (Ib)

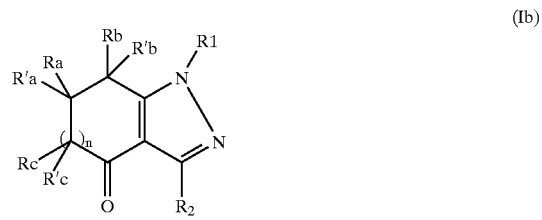

(Ib)

wherein Rb is a chlorine, bromine or iodine atom and n, $R_1$, $R_2$, Ra, R'a, R'b, Rc and R'c are as defined above;

ii) converting the compound of formula (Ib), in the presence of a nucleophylic agent, into a compound of formula (Ic)

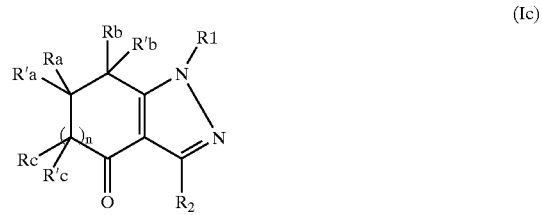

(Ic)

wherein Rb is fluorine, hydroxy, amino, mono- or di-alkylamino, alkylthio, arylthio or alkoxy and n, $R_1$, $R_2$, Ra, R'a, R'b, Rc and R'c are as defined above;

iii) oxidising the compound of formula (Ic) wherein Rb is alkylthio or arylthio into a compound of formula (Id)

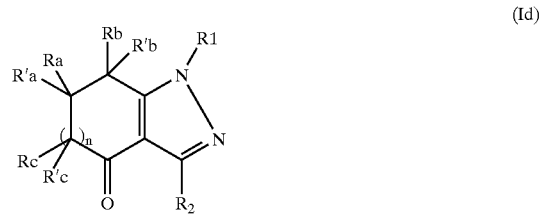

(Id)

wherein Rb is alkylsulfinyl, alkylsulfonyl, arylsulfinyl or arylsulfonyl and n, $R_1$, $R_2$, Ra, R'a, R'b, Rc and R'c are as defined above; or b) when $R_3$ is imino or amino, reacting a compound of formula (I) wherein (x) is a double bond and $R_3$ is oxygen with a suitable amine of formula $R_4$—$NH_2$ (IV)

wherein $R_4$ has the above reported meanings, thus obtaining the corresponding compound of formula (Ie)

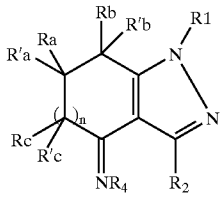
(Ie)

wherein n, $R_1$, $R_2$, $R_4$, Ra, R'a, Rb, R'b, Rc and R'c are as defined above; and, optionally,
  i) reducing the corresponding compound of formula (Ie) into the corresponding amine (If)

(If)

wherein n, $R_1$, $R_2$, $R_4$ Ra, R'a, Rb, R'b, Rc and R'c are as defined above; or, alternatively,
  ii) reacting a compound of formula (I) wherein (x) is a double bond and $R_4$ is oxygen with a suitable di-alkylamine, in the presence of a Lewis acid, so as to obtain the corresponding compound of formula (I) wherein (x) is a single bond and $R_3$ is a di-alkylamino group with from 1 to 6 carbon atoms in the alkyl chains; or c) when (x) is a double bond and $R_3$ is a sulphur atom, reacting a compound of formula (I) wherein (x) is a double bond and $R_3$ is oxygen with a thiating agent, thus obtaining a compound of formula (Ig)

(Ig)

wherein n, $R_1$, $R_2$, Ra, R'a, Rb, R'b, Rc and R'c are as defined above; or d) when (x) is a single bond and $R_3$ is hydroxy or alkoxy, reducing a compound of formula (I) wherein (x) is a double bond and $R_3$ is oxygen into the corresponding compound of formula (Ih)

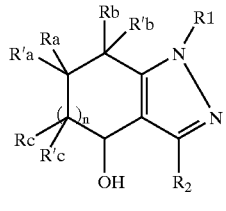
(Ih)

wherein n, $R_1$, $R_2$, Ra, R'a, Rb, R'b, Rc and R'c are as defined above; and, optionally,
  i) alkylating the compound of formula (Ih) with a suitable alkylating agent, thus obtaining the corresponding compound of formula (I) wherein (x) is a single bond, $R_3$ is alkoxy and n, $R_1$, $R_2$, Ra, R'a, Rb, R'b, Rc and R'c are as defined above;

and, if desired, converting a 4,5,6,7-tetrahydroindazole derivative of formula (I) into another such derivative of formula (I), and/or into a salt thereof.

It is clear to the man skilled in the art that if the compounds of formula (I), thus encompassing also those of formula from (Ia) to (Ih), prepared according to the above processes a) b) c) or d) and optional steps thereof, are obtained as an admixture of isomers, their separation into the single isomers of formula (I) according to conventional techniques is still within the scope of the present invention.

Likewise, also the conversion into the free compound (I) of a corresponding salt thereof, according to well-known procedures in the art, is within the scope of the invention.

The above processes from a) to d), and optional steps thereof, are analogy processes which can be carried out according to well known methods in the art.

The reaction between a compound of formula (II) or (IIa) and a substituted hydrazine of formula (III), according to process a) can be carried out in the presence of a base such as sodium acetate or a tertiary amine, for instance triethylamine or di-isopropylethylamine, optionally in the presence of a suitable solvent such as, for instance, ethanol, acetonitrile or toluene, at a temperature ranging from room temperature to reflux.

The conversion of a compound of formula (Ia) into the corresponding halogenated derivative of formula (Ib), according to process a.i), can be carried out in the presence of a suitable halogenating agent, such as N-bromo-, N-chloro-, N-iodo-succinimide or iodine.

Preferably, the said reaction is carried out in the presence of catalytic amounts of an activating agent such as, for instance, α,α-azoisobutyrronitrile (AIBN), and in the presence of a solvent such as dichloromethane, chloroform, $CCl_4$, toluene, or N,N-dimethylformamide, at a temperature ranging from room temperature to reflux for a time varying from about 30 min. to about 96 hours.

The conversion of the halogenated compound of formula (Ib) into a compound of formula (Ic), according to process a.ii), can be carried out in the presence of a proper nucleophylic reagent such as, for instance, argentum fluoride, methylamine, dimethylamine, sodium thiophenate, sodium methoxyde, sodium ethoxyde, sodium hydroxyde/water, sodium hydrogenocarbonate/water, argentum nitrate/water, argentum nitrate/methanol, water, methanol, ethanol.

The above reaction may occurr without any solvent or in the presence of a suitable solvent, e.g. tetrahydrofuran, methanol, ethanol, dichloromethane, acetone, acetonitrile, water, N,N-dimethylformamide, at a temperature ranging from about −10° C. to reflux.

The oxidative reaction for preparing the compounds of formula (Id), according to process a.iii), can be carried out in the presence of conventional oxidising agents such as, for instance, 3-chloro-perbenzoic acid or monopersulfate derivatives (Oxone), in a suitable solvent, for example dichloromethane, chloroform, water, or methanol, at a temperature ranging from about −5° C. to about 40° C.

The conversion of a compound of formula (I) wherein $R_3$ is oxygen into the corresponding imino derivative of formula (Ie), according to process b), can be carried out with a suitable amine of formula (IV), without any solvent or in the presence of ethanol, methanol, toluene, 1,4-dioxane, tetrahydrofuran, dichloromethane or chloroform, at a temperature ranging from room temperature to reflux.

The optional reduction of the corresponding imino derivative of formula (Ie) into the amine (If), according to process b.i), is carried out in the presence of conventional reducing agents such as, for instance, sodium borohydride, sodium cyanoborohydride or sodium triacethoxyborohydride, optionally in the presence of acetic acid, in a suitable solvent, for instance methanol or ethanol, at a temperature ranging from about 0° C. to reflux.

Alternatively, the conversion of a compound of formula (I) wherein (x) is a double bond and $R_3$ is oxygen into the corresponding di-alkylamine of formula (I), according to process b.ii), can be carried out by reacting the proper amine in the presence of a catalytic amount of a Lewis acid, such as titanium(IV) isopropoxide, iron(III) chloride, or titanium (IV) chloride, without any solvent or in the presence of a suitable solvent such as methanol, ethanol, chloroform or toluene, at a temperature ranging from about 0° C. to reflux.

The conversion of a compound of formula (I) wherein $R_3$ is oxygen into a sulfurated derivative of formula (Ig), according to process c), can be carried out by reacting the oxo derivative with a suitable thiation agent such as, for instance, $P_4S_{10}$ or 2,4-bis(4-methoxyphenyl)-1,3,2,4-dithiadiphosphetane-2,4-disulfide, better known as the Lawesson reagent, in a suitable solvent, for example chloroform, toluene, chlorobenzene, or xylene, at a temperature ranging from room temperature to reflux.

Hydroxylated derivatives of formula (Ih), prepared according to process d) from the corresponding oxo derivatives of formula (I), can be obtained by reducing these latter in conventional manners, for instance in the presence of reducing agents such as sodium borohydride, lithium aluminumhydride or lithium borohydride, in a suitable solvent such as methanol, ethanol, diethyl ether, tetrahydrofuran, 1,4-dioxane, or toluene, at a temperature ranging from about 0° C. to reflux.

The compounds of formula (Ih) can be further alkylated according to process d.i) so as to obtain the corresponding compounds of formula (I) wherein (x) is a single bond and $R_3$ is an alkoxy group. The said reaction is carried out in the presence of a conventional alkylating agent such as, for instance, alkyl halides, alkyl mesylates or alkyl tosylates, in the presence of a base such as sodium hydride, sodium methoxyde or sodium ethoxyde, in a suitable solvent such as, for instance, tetrahydrofuran, N,N-dimethylformamide or toluene, at a temperature ranging from about −5° C. to reflux.

The optional salification of a compound of formula (I) as well as the conversion of a salt into the free compound and the separation of a mixture of isomers into the single isomers may be carried out according to conventional methods.

The starting compounds of formula (II) or the polymer supported analogue thereof (IIa) are known or can be prepared according to known methods. For example, the compound of formula (II) or (IIa) may be prepared by reacting a suitable cyclohexan-1,3-dione derivative of formula (V) or a polymer supported analogue of it (Va)

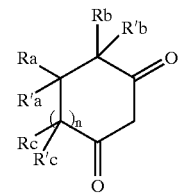

(V)

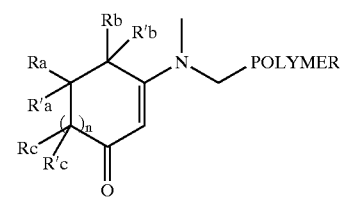

(Va)

wherein n, Ra, R'a, Rb, R'b, Rc and R'c are as defined above, with an acyl chloride of formula $$R_2COCl \qquad (VI)$$

wherein $R_2$ is as defined above, in the presence of pyridine and in a suitable solvent such as 1,2-dichloroethane or chloroform, at a temperature ranging from about −10° C. to room temperature and, if starting from the compound (V), subsequently reacting the resulting intermediate of formula (VII)

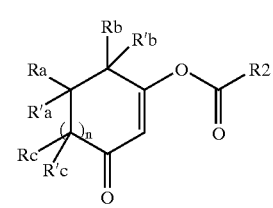

(VII)

with a Lewis acid, for instance aluminum(III) chloride, in a suitable solvent such as 1,2-dichloroethane or chloroform, at a temperature ranging from about −10° C. to room temperature.

Also the compounds of formula (V) and (Va) are known and, if not commercially available, may be prepared by well known synthetic methods.

Any of the above compounds as polymer supported forms, can be easily prepared according to conventional techniques known in the art.

Likewise, the conversion of these polymer supported forms into the free compounds is carried out according to conventional procedures, for instance under hydrolysis.

When preparing the compounds of formula (I) according to the process object of the present invention, optional functional groups within both the starting materials or the intermediates thereof, which could give rise to unwanted side reactions, need to be properly protected according to conventional techniques.

Likewise, the conversion of these latter into the free deprotected compounds may be carried out according to known procedures.

Several compounds of formula (I) have been prepared according to well known combinatorial chemistry techniques by following the aforementioned reported processes.

In particular, several compounds of formula (I), also intended as preferred compounds of the invention, have been prepared by reacting each of the diketale derivatives of formula (V), as per the following table I, with each of the acyl chloride derivatives of formula (VI), as per the following table II and, finally, by reacting each of the resulting intermediate with each of the hydrazines of formula (III), per the enclosed table III.

TABLE I

| | MOLSTRUCTURE |
|---|---|
| 1 |  |
| 2 | |
| 3 | |
| 4 | |

TABLE I-continued

| | MOLSTRUCTURE |
|---|---|
| 5 |  |
| 6 | |
| 7 | |
| 8 | |
| 9 | |

TABLE II

| | MOLSTRUCTURE | MOLNAME | Cas |
|---|---|---|---|
| 1 |  | ACETYL CHLORIDE | 75-36-5 |
| 2 | | CYCLOPROPANECARBONYL CHLORIDE | 4023-34-1 |
| 3 | | ISOBUTYRYL CHLORIDE | 79-30-1 |

TABLE II-continued

| | MOLSTRUCTURE | MOLNAME | Cas |
|---|---|---|---|
| 4 | | BUTYRYL CHLORIDE | 141-75-3 |
| 5 | | PIVALOYL CHLORIDE | 3282-30-2 |
| 6 | | ISOVALERYL CHLORIDE | 108-12-3 |
| 7 | | 2-FUROYL CHLORIDE | 527-69-5 |
| 8 | | ISOXAZOLE-5-CARBONYL CHLORIDE | 62348-13-4 |
| 9 | | BENZOYL CHLORIDE | 98-88-4 |
| 10 | | THIOPHENE-2-CARBONYL CHLORIDE | 5271-67-0 |
| 11 | | PHENYLACETYL CHLORIDE | 103-80-0 |
| 12 | | 2-FLUOROBENZOYL CHLORIDE | 393-52-2 |
| 13 | | 3-FLUOROBENZOYL CHLORIDE | 1711-07-5 |
| 14 | | 4-FLUOROBENZOYL CHLORIDE | 403-43-0 |
| 15 | | 2-THIOPHENEACETYL CHLORIDE | 39098-97-0 |
| 16 | | 3-CYCLOPENTYLPROPIONYL CHLORIDE | 104-97-2 |

TABLE II-continued

| | MOLSTRUCTURE | MOLNAME | Cas |
|---|---|---|---|
| 17 | | 4-CYANOBENZOYL CHLORIDE | 6068-72-0 |
| 18 | | 3-CYANOBENZOYL CHLORIDE | 1711-11-1 |
| 19 | | 2-METHOXYBENZOYL CHLORIDE | 21615-34-9 |
| 20 | | M-ANISOYL CHLORIDE | 1711-05-3 |
| 21 | | P-ANISOYL CHLORIDE | 100-07-2 |
| 22 | | PHENOXYACETYL CHLORIDE | 701-99-5 |
| 23 | | 2-CHLOROBENZOYL CHLORIDE | 609-65-4 |
| 24 | | 3-CHLOROBENZOYL CHLORIDE | 618-46-2 |
| 25 | | 4-CHLOROBENZOYL CHLORIDE | 122-01-0 |
| 26 | | 3,5,5-TRIMETHYLHEXANOYL CHLORIDE | 36727-29-4 |
| 27 | ClH | NICOTINOYL CHLORIDE HYDROCHLORIDE | 20260-53-1 |

TABLE II-continued
| | MOLSTRUCTURE | MOLNAME | Cas |
|---|---|---|---|
| | 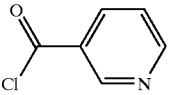 | | |
| 28 | ClH 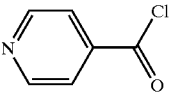 | ISONICOTINOYL CHLORIDE HYDROCHLORIDE | 39178-35-3 |
| 29 | 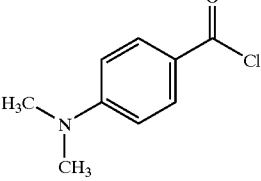 | TRANS-2-PHENYL-1-CYCLOPROPANECARBONYL CHLORIDE | 939-87-7 |
| 30 | 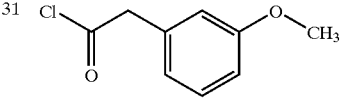 | 4-DIMETHYLAMINOBENZOYL CHLORIDE | 4755-50-4 |
| 31 | 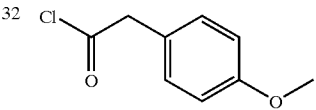 | 3-METHOXYPHENYLACETYL CHLORIDE | 6834-42-0 |
| 32 | 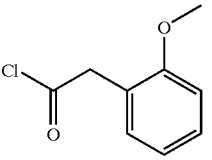 | 4-METHOXYPHENYLACETYL CHLORIDE | 4693-91-8 |
| 33 | 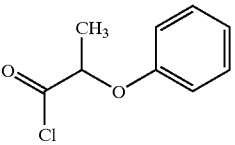 | 2-METHOXYBENZOYL CHLORIDE | 21615-34-9 |
| 34 | 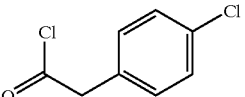 | 2-PHENOXYPROPIONYL CHLORIDE | 122-35-0 |
| 35 | 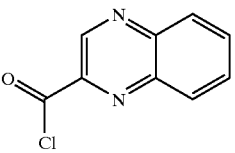 | 4-CHLOROPHENYLACETYL CHLORIDE | 25026-34-0 |
| 36 |  | 2-QUINOXALOYL CHLORIDE | 54745-92-5 |

TABLE II-continued

| MOLSTRUCTURE | MOLNAME | Cas |
|---|---|---|
| 37 | 2,6-DIMETHOXYBENZOYL CHLORIDE | 1989-53-3 |
| 38 | 2,4-DIMETHOXYBENZOYL CHLORIDE | 39828-35-8 |
| 39 | 4-TERT-BUTYLBENZOYL CHLORIDE | 1710-98-1 |
| 40 | 4-IODOBENZOYL CHLORIDE | 1711-02-0 |

TABLE III

| MOLSTRUCTURE | MOLNAME | CAS |
|---|---|---|
| 1 | METHYLHYDRAZINE | 60-34-4 |
| 2 | 2-HYDROXYETHYLHYDRAZINE | 109-84-2 |
| 3 | 2-CYANOETHYLHYDRAZINE | 353-07-1 |
| 4 | PHENYLHYDRAZINE | 100-63-0 |
| 5 | 2-HYDRAZINOPYRIDINE | 4930-98-7 |
| 6 | 2,2,2-TRIFLUOROETHYLHYDRAZINE | 5042-30-8 |
| 7 | 3-CHLOROPYRIDAZIN-6-YL HYDRAZINE | 17284-97-8 |
| 8 | 2-HYDRAZINOBENZOTHIAZOLE | 615-21-4 |

TABLE III-continued

| | MOLSTRUCTURE | MOLNAME | CAS |
|---|---|---|---|
| 9 | H₂N-NH-C₆H₄-OMe | 3-METHOXYPHENYLHYDRAZINE HYDROCHLORIDE | 39232-91-2 |
| 10 | H₂N-NH-C₆H₄-Cl | 3-CHLOROPHENYLHYDRAZINE HYDROCHLORIDE | 2312-23-4 |
| 11 | H₂N-NH-C₆H₄-CH(CH₃)₂ | 4-ISOPROPYLPHENYLHYDRAZINE HYDROCHLORIDE | 118427-29-5 |
| 12 | 7-chloro-4-hydrazinoquinoline structure | 7-CHLORO-4-HYDRAZINOQUINOLINE | 23834-14-2 |
| 13 | H₂N-NH-C₆H₄-I | 4-IODOPHENYLHYDRAZINE | 13116-27-3 |

Pharmacology

The compounds of formula (I) of the invention are active as cdk/cyclin inhibitors as they gave positive results when tested according to the following procedure.

The compounds of formula (I) are therefore useful to restrict the unregulated proliferation of tumor cells, hence in therapy in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds was determined through a method of assay based on the use of the MultiScreen-PH 96 well plate (Millipore), in which a phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter.

The inhibition assay of cdk2/Cyclin A activity was performed according to the following protocol:

Kinase reaction: 1.5 $\mu$M histone H1 substrate, 25 $\mu$M ATP (0.5 uCi $P^{33}$g-ATP), 100 ng Cyclin A/cdk2 complex, 10 $\mu$M inhibitor in a final volume of 100 $\mu$l buffer (TRIS HCl 10 mM pH 7.5, MgCl$_2$ 10 mM, 7.5 mM DTT) were added to each well of a 96 U bottom well plate. After 10 min at 37° C. incubation, reaction was stopped by 20 $\mu$l EDTA 120 mM.

Capture: 100 $\mu$l were transferred from each well to MultiScreen plate, to allow substrate binding to phosphocellulose filter. Plates were then washed 3 times with 150 $\mu$l/well PBS Ca$^{++}$/Mg$^{++}$ free and filtered by MultiScreen filtration system.

Detection: filters were allowed to dry at 37° C., then 100 $\mu$l/well scintillant were added and $^{33}$P labelled histone H1 was detected by radioactivity counting in the Top-Count instrument.

Results: data were analysed and expressed as % inhibition referred to total activity of enzyme (=100%).

All compounds showing inhibition≧50% were further analysed in order to study and define the kinetic-profile of inhibitor through Ki calculation.

The protocol used was the same described above, except for ATP and substrate concentrations. Either the concentration of ATP and histone H1 substrate were varied: 4, 8,12, 24, 48 $\mu$M for ATP (containing proportionally diluted $P^{33}$g-ATP) and 0.4, 0.8, 1.2, 2.4, 4.8 $\mu$M for histone were used in absence and presence of two different, properly chosen inhibitor concentrations.

Experimental data were analysed by the computer program "SigmaPlot" for Ki determination, using a random bireactant system equation:

$$v = \frac{V_{max}\frac{(A)(B)}{aK_AK_B}}{1 + \frac{(A)}{K_A} + \frac{(B)}{K_B} + \frac{(A)(B)}{aK_AK_B}}$$

where A=ATP and B=histone H1.

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The present invention also includes pharmaceutical compositions comprising a compound of formula (I), or a pharmaceutically acceptable salt thereof, in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the present invention.

EXAMPLE 1

Preparation of 3-Acetyloxy-5,5-dimethyl-2-cyclohexenone

Acetyl chloride (1.1 ml, 15.65 mmol) was added to a stirred solution of 5,5-dimethyl-cyclohexane-1,3-dione (2.1 g, 14.23 mmol) and pyridine (1.14 ml), in chloroform (50 ml). The mixture was stirred at room temperature for about 1.5 hours, then washed with water, 0.1N HCl, saturated aqueous sodium hydrogen carbonate and water. The organic phase was dried over sodium sulfate and evaporated to dryness to give 2.5 g (96%) of the title compound as a colourless oil, which was used as such without any further purification.

$^1$H-NMR (CDCl$_3$) δ ppm: 5.88 (s, 1H, CH=); 2.4 (s, 2H, CH$_2$C=); 2.25 (s, 2H, CH$_2$CO); 2.18 (s, 3H, CH$_3$CO); 1.1 (s, 6H, gem CH$_3$).

EXAMPLE 2

Preparation of 2-Acetyl-5,5-dimethyl-cyclohexane-1,3-dione.

3-Acetyloxy-5,5-dimethyl-2-cyclohexenone (2 g, 11 mmol), prepared as described in example 1, was added to a stirred suspension of anhydrous aluminum chloride (3 g, 22 mmol) in chloroform (35 ml). The mixture was stirred for 1.5 hours at room temperature and then poured into a mixture of ice and concentrated HCl. The organic layer was separated and the aqueous phase was extracted with chloroform. The combined organic phases were washed with water, dried over sodium sulfate and evaporated to dryness to yield 1 g (50%) of the title compound which was used as such without any further purification.

EXAMPLE 3
Preparation of 1-(2-Pyridyl)-3,6,6-trimethyl-4-oxo-4,5,6,7-tetrahydroindazole.

A mixture of 2-acetyl-5,5-dimethyl-cyclohexane-1,3-dione (0.5 g, 2.75 mmol), prepared as described in example 2, and 2-hydrazino-pyridine (0.3 g, 2.75 mmol) in ethanol (15 ml) was stirred at 80° C. for 4 hours. After evaporation of the solvent, the residue was chromatographed on silica gel (cyclohexane:ethyl acetate=10:20). The title compound was obtained as a colourless solid (0.5 g, 73%): m.p. 122–123° C.

$^1$H-NMR (DMSO-d$^6$) δ ppm: 8.51–7.4 (m, 4H, 2-Py); 3.25 (s, 2H, CH$_2$); 2.4 (s, 3H, CH$_3$); 2.27 (s, 2H, CH$_2$); 1.1 (s, 6H, gem CH$_3$).

By working in an analogous way and by using the proper hydrazine derivative and the proper cyclohexane 1,3-dione, the following compounds can be prepared:

1-phenylmethyl-3,6,6-trimethyl-4-oxo-4,5,6,7-tetrahydroindazole $^1$H-NMR (DMSO-d$^6$) δ ppm: 7.4–7.15 (m, 5H, Ph); 5.22 (s, 2H, CH$_2$Ph); 2.64 (s, 2H, CH$_2$); 2.27 (s, 3H, CH$_3$); 2.21 (s, 2H, CH$_2$); 1 (s, 6H, gem CH$_3$); and 1-(3-nitrophenyl)-3,6,6-trimethyl-4-oxo-4,5,6,7-tetrahydroindazole; m.p. 133–134° C.; $^1$H-NMR (DMSO-d$^6$) δ ppm: 8.58–7.82 (m, 4H, Ar); 2.98 (s, 2H, CH$_2$); 2.4 (s, 3H, CH$_3$); 2.32 (s, 2H, CH$_2$); 1.05 (s, 6H, gem CH$_3$);

1,3-dimethyl-1,5,6,7-tetrahydro-4H-indazol-4-one;
1-(2-hydroxyethyl)-3-methyl-1,5,6,7-tetrahydro-4H-indazol-4-one;
3-methyl-1-phenyl-1,5,6,7-tetrahydro-4H-indazol-4-one;
3-methyl-1-(2-pyridinyl)-1,5,6,7-tetrahydro-4H-indazol-4-one;
1-(6-chloro-3-pyridazinyl)-3-methyl-1,5,6,7-tetrahydro-4H-indazol-4-one;
1-(3-methoxyphenyl)-3-methyl-1,5,6,7-tetrahydro-4H-indazol-4-one;
1-(3-chlorophenyl)-3-methyl-1,5,6,7-tetrahydro-4H-indazol-4-one;
1-(4-isopropylphenyl)-3-methyl-1,5,6,7-tetrahydro-4H-indazol-4-one;
1-(4-iodophenyl)-3-methyl-1,5,6,7-tetrahydro-4H-indazol-4-one;
3-cyclopropyl-1-methyl-1,5,6,7-tetrahydro-4H-indazol-4-one;
3-cyclopropyl-1-(2-hydroxyethyl)-1,5,6,7-tetrahydro-4H-indazol-4-one;
3-cyclopropyl-1-phenyl-1,5,6,7-tetrahydro-4H-indazol-4-one;
3-cyclopropyl-1-(2-pyridinyl)-1,5,6,7-tetrahydro-4H-indazol-4-one;
1-(6-chloro-3-pyridazinyl)-3-cyclopropyl-1,5,6,7-tetrahydro-4H-indazol-4-one;
3-cyclopropyl-1-(3-methoxyphenyl)-1,5,6,7-tetrahydro-4H-indazol-4-one;
1-(3-chlorophenyl)-3-cyclopropyl-1,5,6,7-tetrahydro-4H-indazol-4-one;
3-cyclopropyl-1-(4-isopropylphenyl)-1,5,6,7-tetrahydro-4H-indazol-4-one;
3-cyclopropyl-1-(4-iodophenyl)-1,5,6,7-tetrahydro-4H-indazol-4-one;
3-isopropyl-1-methyl-1,5,6,7-tetrahydro-4H-indazol-4-one;
1-(2-hydroxyethyl)-3-isopropyl-1,5,6,7-tetrahydro-4H-indazol-4-one;
3-isopropyl-1-phenyl-1,5,6,7-tetrahydro-4H-indazol-4-one;
3-isopropyl-1-(2-pyridinyl)-1,5,6,7-tetrahydro-4H-indazol-4-one;
1-(6-chloro-3-pyridazinyl)-3-isopropyl-1,5,6,7-tetrahydro-4H-indazol-4-one;
3-isopropyl-1-(3-methoxyphenyl)-1,5,6,7-tetrahydro-4H-indazol-4-one;
1-(3-chlorophenyl)-3-isopropyl-1,5,6,7-tetrahydro-4H-indazol-4-one;
3-isopropyl-1-(4-isopropylphenyl)-1,5,6,7-tetrahydro-4H-indazol-4-one;
1-(4-iodophenyl)-3-isopropyl-1,5,6,7-tetrahydro-4H-indazol-4-one;
1-methyl-3-propyl-1, 5,6,7-tetrahydro-4H-indazol-4-one;
1-(2-hydroxyethyl)-3-propyl-1, 5,6,7-tetrahydro-4H-indazol-4-one;
1-phenyl-3-propyl-1,5,6,7-tetrahydro-4H-indazol-4-one;
3-propyl-1-(2-pyridinyl)-1,5,6, 7-tetrahydro-4H-indazol-4-one;
1-(6-chloro-3-pyridazinyl)-3-propyl-1,5,6,7-tetrahydro-4H-indazol-4-one;
1-(3-methoxyphenyl)-3-propyl-1,5,6,7-tetrahydro-4H-indazol-4-one;
1-(3-chlorophenyl)-3-propyl-1,5,6,7-tetrahydro-4H-indazol-4-one;
1-(4-isopropylphenyl)-3-propyl-1,5,6,7-tetrahydro-4H-indazol-4-one;
1-(4-iodophenyl)-3-propyl-1,5,6,7-tetrahydro-4H-indazol-4-one;
3-tertbuty-1methyl-1,5,6,7-tetrahydro-4H-indazol-4-one;
1-(2-hydroxyethyl)-3-tertbutyl-1,5,6,7-tetrahydro-4H-indazol-4-one;
1-phenyl-3-tertbutyl-1,5,6,7-tetrahydro-4H-indazol-4-one;
1-(2-pyridinyl)-3-tertbutyl-1,5,6,7-tetrahydro-4H-indazol-4-one;
1-(6-chloro-3-pyridazinyl)-3-tertbutyl-1,5,6,7-tetrahydro-4H-indazol-4-one;
1-(3-methoxyphenyl)-3-tertbutyl-1,5,6,7-tetrahydro-4H-indazol-4-one;
1-(3-chlorophenyl)-3-tertbutyl-1,5,6,7-tetrahydro-4H-indazol-4-one;
1-(4-isopropylphenyl)-3-tertbutyl-1-1,5,6,7-tetrahydro-4H-indazol-4-one;
1-(4-iodophenyl)-3-tertbutyl-1,5,6,7-tetrahydro-4H-indazol-4-one;
3-isobutyl-1-methyl-1,5,6,7-tetrahydro-4H-indazol-4-one;
1-(2-hydroxyethyl)-3-isobutyl-1,5,6,7-tetrahydro-4H-indazol-4-one;
3-isobutyl-1-phenyl-1,5,6,7-tetrahydro-4H-indazol-4-one;
3-isobutyl-1-(2-pyridinyl)-1,5,6,7-tetrahydro-4H-indazol-4-one;
1-(6-chloro-3-pyridazinyl)-3-isobutyl-1,5,6,7-tetrahydro-4H-indazol-4-one;
3-isobutyl-1-(3-methoxyphenyl)-1,5,6,7-tetrahydro-4H-indazol-4-one;
1-(3-chlorophenyl)-3-isobutyl-1,5,6,7-tetrahydro-4H-indazol-4-one;

3-isobutyl-1-(4-isopropylphenyl)-1-1,5,6,7-tetrahydro-4H-indazol-4-one;

1-(4-iodophenyl)-3-isobutyl-1,5,6,7-tetrahydro-4H-indazol-4-one;

1-methyl-3-(2,4,4-trimethylpentyl)-1,5,6,7-tetrahydro-4H-indazol-4-one;

1-(2-hydroxyethyl)-3-(2,4,4-trimethylpentyl)-1,5,6,7-tetrahydro-4H-indazol-4-one;

1-phenyl-3-(2,4,4-trimethylpentyl)-1,5,6,7-tetrahydro-4H-indazol-4-one;

3-(2,4,4-trimethylpentyl)-1-(2-pyridinyl)-1,5,6,7-tetrahydro-4H-indazol-4-one;

1-(6-chloro-3-pyridazinyl)-3-(2,4,4-trimethylpentyl)-1,5,6,7-tetrahydro-4H-indazol-4-one;

1-(3-methoxyphenyl)-3-(2,4,4-trimethylpentyl)-1,5,6,7-tetrahydro-4H-indazol-4-one;

1-(3-chlorophenyl)-3-(2,4,4-trimethylpentyl)-1,5,6,7-tetrahydro-4H-indazol-4-one;

1-(4-isopropylphenyl)-3-(2,4,4-trimethylpentyl)-1-1,5,6,7-tetrahydro-4H-indazol-4-one;

1-(4-iodophenyl)-3-(2,4,4-trimethylpentyl)-1,5,6,7-tetrahydro-4H-indazol-4-one;

1,3,6-trimethyl-1,5,6,7-tetrahydro-4H-indazol-4-one;

1-(2-hydroxyethyl)-3,6-dimethyl-1,5,6,7-tetrahydro-4H-indazol-4-one;

3,6-dimethyl-1-phenyl-1,5,6,7-tetrahydro-4H-indazol-4-one;

3,6-dimethyl-1-(2-pyridinyl)-1,5,6,7-tetrahydro-4H-indazol-4-one;

1-(6-chloro-3-pyridazinyl)-3,6-dimethyl-1,5,6,7-tetrahydro-4H-indazol-4-one;

1-(3-methoxyphenyl)-3,6-dimethyl-1,5,6,7-tetrahydro-4H-indazol-4-one;

1-(3-chlorophenyl)-3,6-dimethyl-1,5,6,7-tetrahydro-4H-indazol-4-one;

1-(4-isopropylphenyl)-3,6-dimethyl-1,5,6,7-tetrahydro-4H-indazol-4-one;

1-(4-iodophenyl)-3,6-dimethyl-1,5,6,7-tetrahydro-4H-indazol-4-one;

3-cyclopropyl-1,6-dimethyl-1,5,6,7-tetrahydro-4H-indazol-4-one;

3-cyclopropyl-1-(2-hydroxyethyl)-6-methyl-1,5,6,7-tetrahydro-4H-indazol-4-one;

3-cyclopropyl-6-methyl-1-phenyl-1,5,6,7-tetrahydro-4H-indazol-4-one;

3-cyclopropyl-6-methyl-1-(2-pyridinyl)-1,5,6,7-tetrahydro-4H-indazol-4-one;

1-(6-chloro-3-pyridazinyl)-3-cyclopropyl-6-methyl-1,5,6,7-tetrahydro-4H-indazol-4-one;

3-cyclopropyl-1-(3-methoxyphenyl)-6-methyl-1,5,6,7-tetrahydro-4H-indazol-4-one;

1-(3-chlorophenyl)-3-cyclopropyl-6-methyl-1,5,6,7-tetrahydro-4H-indazol-4-one;

3-cyclopropyl-1-(4-isopropylphenyl)-6-methyl-1,5,6,7-tetrahydro-4H-indazol-4-one;

3-cyclopropyl-1-(4-iodophenyl)-6-methyl-1,5,6,7-tetrahydro-4H-indazol-4-one;

3-isopropyl-1,6-dimethyl-1,5,6,7-tetrahydro-4H-indazol-4-one;

1-(2-hydroxyethyl)-3-isopropyl-6-methyl-1,5,6,7-tetrahydro-4H-indazol-4-one;

3-isopropyl-6-methyl-1-phenyl-1,5,6,7-tetrahydro-4H-indazol-4-one;

3-isopropyl-6-methyl-1-(2-pyridinyl)-1,5,6,7-tetrahydro-4H-indazol-4-one;

1-(6-chloro-3-pyridazinyl)-3-isopropyl-6-methyl-1,5,6,7-tetrahydro-4H-indazol-4-one;

3-isopropyl-1-(3-methoxyphenyl)-6-methyl-1,5,6,7-tetrahydro-4H-indazol-4-one;

1-(3-chlorophenyl)-3-isopropyl-6-methyl-1,5,6,7-tetrahydro-4H-indazol-4-one;

3-isopropyl-1-(4-isopropylphenyl)-6-methyl-1,5,6,7-tetrahydro-4H-indazol-4-one;

1-(4-iodophenyl)-3-isopropyl-6-methyl-1,5,6,7-tetrahydro-4H-indazol-4-one;

1,6-dimethyl-3-propyl-1,5,6,7-tetrahydro-4H-indazol-4-one;

1-(2-hydroxyethyl)-6-methyl-3-propyl-1,5,6,7-tetrahydro-4H-indazol-4-one;

6-methyl-1-phenyl-3-propyl-1,5,6,7-tetrahydro-4H-indazol-4-one;

6-methyl-3-propyl-1-(2-pyridinyl)-1,5,6,7-tetrahydro-4H-indazol-4-one;

1-(6-chloro-3-pyridazinyl)-6-methyl-3-propyl-1,5,6,7-tetrahydro-4H-indazol-4-one;

1-(3-methoxyphenyl)-6-methyl-3-propyl-1,5,6,7-tetrahydro-4H-indazol-4-one;

1-(3-chlorophenyl)-6-methyl-3-propyl-1,5,6,7-tetrahydro-4H-indazol-4-one;

1-(4-isopropylphenyl)-6-methyl-3-propyl-1,5,6,7-tetrahydro-4H-indazol-4-one;

1-(4-iodophenyl)-6-methyl-6-methyl-3-propyl-1,5,6,7-tetrahydro-4H-indazol-4-one;

3-tertbuty-1,6-dimethyl-1-1,5,6,7-tetrahydro-4H-indazol-4-one;

1-(2-hydroxyethyl)-6-methyl-3-tertbutyl-1,5,6,7-tetrahydro-4H-indazol-4-one;

6-methyl-1-phenyl-3-tertbutyl-1,5,6,7-tetrahydro-4H-indazol-4-one;

6-methyl-1-(2-pyridinyl)-3-tertbutyl-1,5,6,7-tetrahydro-4H-indazol-4-one;

1-(6-chloro-3-pyridazinyl)-6-methyl-3-tertbutyl-1,5,6,7-tetrahydro-4H-indazol-4-one;

1-(3-methoxyphenyl)-6-methyl-3-tertbutyl-1,5,6,7-tetrahydro-4H-indazol-4-one;

1-(3-chlorophenyl)-6-methyl-3-tertbutyl-1,5,6,7-tetrahydro-4H-indazol-4-one;

1-(4-isopropylphenyl)-6-methyl-3-tertbutyl-1-1,5,6,7-tetrahydro-4H-indazol-4-one;

1-(4-iodophenyl)-6-methyl-3-tertbutyl-1,5,6,7-tetrahydro-4H-indazol-4-one;

3-isobutyl-1,6-dimethyl-1,5,6,7-tetrahydro-4H-indazol-4-one;

1-(2-hydroxyethyl)-3-isobutyl-6-methyl-1,5,6,7-tetrahydro-4H-indazol-4-one;

3-isobutyl-6-methyl-1-phenyl-1,5,6,7-tetrahydro-4H-indazol-4-one;

3-isobutyl-6-methyl-1-(2-pyridinyl)-1,5,6,7-tetrahydro-4H-indazol-4-one;

1-(6-chloro-3-pyridazinyl)-3-isobutyl-6-methyl-1,5,6,7-tetrahydro-4H-indazol-4-one;

3-isobutyl-1-(3-methoxyphenyl)-6-methyl-1,5,6,7-tetrahydro-4H-indazol-4-one;

1-(3-chlorophenyl)-3-isobutyl-6-methyl-1,5,6,7-tetrahydro-4H-indazol-4-one;

3-isobutyl-1-(4-isopropylphenyl)-6-methyl-1-1,5,6,7-tetrahydro-4H-indazol-4-one;

1-(4-iodophenyl)-3-isobutyl-6-methyl-1,5,6,7-tetrahydro-4H-indazol-4-one;

1,6-dimethyl-3-(2,4,4-trimethylpentyl)-1,5,6,7-tetrahydro-4H-indazol-4-one;

1-(2-hydroxyethyl)-6-methyl-3-(2,4,4-trimethylpentyl)-1,5,6,7-tetrahydro-4H-indazol-4-one;

6-methyl-1-phenyl-3-(2,4,4-trimethylpentyl)-1,5,6,7-tetrahydro-4H-indazol-4-one;

6-methyl-3-(2,4,4-trimethylpentyl)-1-(2-pyridinyl)-1,5,6,7-tetrahydro-4H-indazol-4-one;

1-(6-chloro-3-pyridazinyl)-6-methyl-3-(2,4,4-trimethylpentyl)-1,5,6,7-tetrahydro-4H-indazol-4-one;

1-(3-methoxyphenyl)-6-methyl-3-(2,4,4-trimethylpentyl)-1,5,6,7-tetrahydro-4H-indazol-4-one;

1-(3-chlorophenyl)-6-methyl-3-(2,4,4-trimethylpentyl)-1,5,6,7-tetrahydro-4H-indazol-4-one;

1-(4-isopropylphenyl)-6-methyl-3-(2,4,4-trimethylpentyl)-1-1,5,6,7-tetrahydro-4H-indazol-4-one;

1-(4-iodophenyl)-6-methyl-3-(2,4,4-trimethylpentyl)-1,5,6,7-tetrahydro-4H-indazol-4-one;

6-isopropyl-1,3-dimethyl-1,5,6,7-tetrahydro-4H-indazol-4-one;

1-(2-hydroxyethyl)-6-isopropyl-3-methyl-1,5,6,7-tetrahydro-4H-indazol-4-one;

6-isopropyl-3-methyl-1-phenyl-1,5,6,7-tetrahydro-4H-indazol-4-one;

6-isopropyl-3-methyl-1-(2-pyridinyl)-1,5,6,7-tetrahydro-4H-indazol-4-one;

1-(6-chloro-3-pyridazinyl)-6-isopropyl-3-methyl-1,5,6,7-tetrahydro-4H-indazol-4-one;

6-isopropyl-1-(3-methoxyphenyl)-3-methyl-1,5,6,7-tetrahydro-4H-indazol-4-one;

1-(3-chlorophenyl)-6-isopropyl-3-methyl-1,5,6,7-tetrahydro-4H-indazol-4-one;

6-isopropyl-1-(4-isopropylphenyl)-3-methyl-1,5,6,7-tetrahydro-4H-indazol-4-one;

1-(4-iodophenyl)-6-isopropyl-3-methyl-1,5,6,7-tetrahydro-4H-indazol-4-one;

3-cyclopropyl-6-isopropyl-1-methyl-1,5,6,7-tetrahydro-4H-indazol-4-one;

3-cyclopropyl-1-(2-hydroxyethyl)-6-isopropyl-1,5,6,7-tetrahydro-4H-indazol-4-one;

3-cyclopropyl-6-isopropyl-1-phenyl-1,5,6,7-tetrahydro-4H-indazol-4-one;

3-cyclopropyl-6-isopropyl-1-(2-pyridinyl)-1,5,6,7-tetrahydro-4H-indazol-4-one;

1-(6-chloro-3-pyridazinyl)-3-cyclopropyl-6-isopropyl-1,5,6,7-tetrahydro-4H-indazol-4-one;

3-cyclopropyl-6-isopropyl-1-(3-methoxyphenyl)-1,5,6,7-tetrahydro-4H-indazol-4-one;

1-(3-chlorophenyl)-3-cyclopropyl-6-isopropyl-1,5,6,7-tetrahydro-4H-indazol-4-one;

3-cyclopropyl-6-isopropyl-1-(4-isopropylphenyl)-1,5,6,7-tetrahydro-4H-indazol-4-one;

3-cyclopropyl-1-(4-iodophenyl)-6-isopropyl-1,5,6,7-tetrahydro-4H-indazol-4-one;

3,6-diisopropyl-1-methyl-1,5,6,7-tetrahydro-4H-indazol-4-one;

1-(2-hydroxyethyl)-3, 6-diisopropyl-1,5,6,7-tetrahydro-4H-indazol-4-one;

3,6-diisopropyl-1-phenyl-1,5,6,7-tetrahydro-4H-indazol-4-one;

3,6-diisopropyl-1-(2-pyridinyl)-1,5,6,7-tetrahydro-4H-indazol-4-one;

1-(6-chloro-3-pyridazinyl)-3,6-diisopropyl-1,5,6,7-tetrahydro-4H-indazol-4-one;

3,6-diisopropyl-1-(3-methoxyphenyl)-1,5,6,7-tetrahydro-4H-indazol-4-one;

1-(3-chlorophenyl)-3,6-diisopropyl-1,5,6,7-tetrahydro-4H-indazol-4-one;

3,6-diisopropyl-1-(4-isopropylphenyl)-1,5,6,7-tetrahydro-4H-indazol-4-one;

1-(4-iodophenyl)-3,6-diisopropyl-1,5,6,7-tetrahydro-4H-indazol-4-one;

1-methyl-6-isopropyl-3-propyl-1,5,6,7-tetrahydro-4H-indazol-4-one;

1-(2-hydroxyethyl)-6-isopropyl-3-propyl-1,5,6,7-tetrahydro-4H-indazol-4-one;

6-isopropyl-1-phenyl-3-propyl-1,5,6,7-tetrahydro-4H-indazol-4-one;

6-isopropyl-3-propyl-1-(2-pyridinyl)-1,5,6,7-tetrahydro-4H-indazol-4-one;

-1-(6-chloro-3-pyridazinyl)-6-isopropyl-3-propyl-1,5,6,7-tetrahydro-4H-indazol-4-one;

1-(3-methoxyphenyl)-6-isopropyl-3-propyl-1,5,6,7-tetrahydro-4H-indazol-4-one;

1-(3-chlorophenyl)-6-isopropyl-3-propyl-1,5,6,7-tetrahydro-4H-indazol-4-one;

1-(4-isopropylphenyl)-6-isopropyl-3-propyl-1,5,6,7-tetrahydro-4H-indazol-4-one;

1-(4-iodophenyl)-6-isopropyl-3-propyl-1,5,6,7-tetrahydro-4H-indazol-4-one;

6-isopropyl-3-tertbuty-1-methyl-1-1,5,6,7-tetrahydro-4H-indazol-4-one;

1-(2-hydroxyethyl)-6-isopropyl-3-tertbutyl-1,5,6,7-tetrahydro-4H-indazol-4-one;

6-isopropyl-1-phenyl-3-tertbutyl-1,5,6,7-tetrahydro-4H-indazol-4-one;

6-isopropyl-1-(2-pyridinyl)-3-tertbutyl-1,5,6,7-tetrahydro-4H-indazol-4-one;

1-(6-chloro-3-pyridazinyl)-6-isopropyl-3-tertbutyl-1,5,6,7-tetrahydro-4H-indazol-4-one;

6-isopropyl-1-(3-methoxyphenyl)-3-tertbutyl-1,5,6,7-tetrahydro-4H-indazol-4-one;

1-(3-chlorophenyl)-6-isopropyl-3-tertbutyl-1,5,6,7-tetrahydro-4H-indazol-4-one;

6-isopropyl-1-(4-isopropylphenyl)-3-tertbutyl-1-1,5,6,7-tetrahydro-4H-indazol-4-one;

1-(4-iodophenyl)-6-isopropyl-3-tertbutyl-1,5,6,7-tetrahydro-4H-indazol-4-one;

3-isobutyl-6-isopropyl-1-methyl-1,5,6,7-tetrahydro-4H-indazol-4-one;

1-(2-hydroxyethyl)-3-isobutyl-6-isopropyl-1,5,6,7-tetrahydro-4H-indazol-4-one;

3-isobutyl-6-isopropyl-1-phenyl-1,5,6,7-tetrahydro-4H-indazol-4-one;

3-isobutyl-6-isopropyl-1-(2-pyridinyl)-1,5,6,7-tetrahydro-4H-indazol-4-one;

1-(6-chloro-3-pyridazinyl)-3-isobutyl-6-isopropyl-1,5,6,7-tetrahydro-4H-indazol-4-one;

3-isobutyl-6-isopropyl-1-(3-methoxyphenyl)-1,5,6,7-tetrahydro-4H-indazol-4-one;

1-(3-chlorophenyl)-3-isobutyl-6-isopropyl-1,5,6,7-tetrahydro-4H-indazol-4-one;

3-isobutyl-6-isopropyl-1-(4-isopropylphenyl)-1-1,5,6,7-tetrahydro-4H-indazol-4-one;

1-(4-iodophenyl)-3-isobutyl-6-isopropyl-1,5,6,7-tetrahydro-4H-indazol-4-one;

6-isopropyl-1-methyl-3-(2,4,4-trimethylpentyl)-1,5,6,7-tetrahydro-4H-indazol-4-one;

1-(2-hydroxyethyl)-6-isopropyl-3-(2,4,4-trimethylpentyl)-1,5,6,7-tetrahydro-4H-indazol-4-one;

6-isopropyl-1-phenyl-3-(2,4,4-trimethylpentyl)-1,5,6,7-tetrahydro-4H-indazol-4-one;

6-isopropyl-3-(2,4, 4-trimethylpentyl)-1-(2-pyridinyl)-1,5,6,7-tetrahydro-4H-indazol-4-one;

1-(6-chloro-3-pyridazinyl)-6-isopropyl-3-(2,4,4-trimethylpentyl)-1,5,6,7-tetrahydro-4H-indazol-4-one;

6-isopropyl-1-(3-methoxyphenyl)-3-(2,4,4-trimethylpentyl)-1,5,6,7-tetrahydro-4H-indazol-4-one;

1-(3-chlorophenyl)-6-isopropyl-3-(2,4,4-trimethylpentyl)-1,5,6,7-tetrahydro-4H-indazol-4-one;

6-isopropyl-1-(4-isopropylphenyl)-3-(2,4,4-trimethylpentyl)-1-1,5,6,7-tetrahydro-4H-indazol-4-one;

1-(4-iodophenyl)-6-isopropyl-3-(2,4,4-trimethylpentyl)-1,5,6,7-tetrahydro-4H-indazol-4-one;

1,3,6,6-tetramethyl-1,5,6,7-tetrahydro-4H-indazol-4-one;

1-(2-hydroxyethyl)-3,6,6-trimethyl-1,5,6,7-tetrahydro-4H-indazol-4-one;

3,6,6-trimethyl-1-phenyl-1,5,6,7-tetrahydro-4H-indazol-4-one;

1-(6-chloro-3-pyridazinyl)-3,6,6-trimethyl-1,5,6,7-tetrahydro-4H-indazol-4-one;

1-(3-methoxyphenyl)-3,6,6-trimethyl-1,5,6,7-tetrahydro-4H-indazol-4-one;

1-(3-chlorophenyl)-3,6,6-trimethyl-1,5,6,7-tetrahydro-4H-indazol-4-one;

1-(4-isopropylphenyl)-3,6,6-trimethyl-1,5,6,7-tetrahydro-4H-indazol-4-one;

1-(4-iodophenyl)-3,6,6-trimethyl-1,5,6,7-tetrahydro-4H-indazol-4-one;

3-cyclopropyl-1,6,6-trimethyl-1,5,6,7-tetrahydro-4H-indazol-4-one;

3-cyclopropyl-1-(2-hydroxyethyl)-6,6-dimethyl-1,5,6,7-tetrahydro-4H-indazol-4-one;

3-cyclopropyl-6,6-dimethyl-1-phenyl-1,5,6,7-tetrahydro-4H-indazol-4-one;

3-cyclopropyl-6,6-dimethyl-1-(2-pyridinyl)-1,5,6,7-tetrahydro-4H-indazol-4-one;

1-(6-chloro-3-pyridazinyl)-3-cyclopropyl-6,6-dimethyl-1,5,6,7-tetrahydro-4H-indazol-4-one;

3-cyclopropyl-1-(3-methoxyphenyl)-6,6-dimethyl-1,5,6,7-tetrahydro-4H-indazol-4-one;

1-(3-chlorophenyl)-3-cyclopropyl-6,6-dimethyl-1,5,6,7-tetrahydro-4H-indazol-4-one;

3-cyclopropyl-1-(4-isopropylphenyl)-6,6-dimethyl-1,5,6,7-tetrahydro-4H-indazol-4-one;

3-cyclopropyl-1-(4-iodophenyl)-6,6-dimethyl-1,5,6,7-tetrahydro-4H-indazol-4-one;

3-isopropyl-1,6,6-trimethyl-1,5,6,7-tetrahydro-4H-indazol-4-one;

1-(2-hydroxyethyl)-3-isopropyl-6,6-dimethyl-1,5,6,7-tetrahydro-4H-indazol-4-one;

3-isopropyl-6,6-dimethyl-1-phenyl-1,5,6,7-tetrahydro-4H-indazol-4-one;

3-isopropyl-6,6-dimethyl-1-(2-pyridinyl)-1,5,6,7-tetrahydro-4H-indazol-4-one;

1-(6-chloro-3-pyridazinyl)-3-isopropyl-6,6-dimethyl-1,5,6,7-tetrahydro-4H-indazol-4-one;

3-isopropyl-1-(3-methoxyphenyl)-6,6-dimethyl-1,5,6,7-tetrahydro-4H-indazol-4-one;

1-(3-chlorophenyl)-3-isopropyl-6,6-dimethyl-1,5,6,7-tetrahydro-4H-indazol-4-one;

3-isopropyl-1-(4-isopropylphenyl)-6,6-dimethyl-1,5,6,7-tetrahydro-4H-indazol-4-one;

1-(4-iodophenyl)-3-isopropyl-6,6-dimethyl-1,5,6,7-tetrahydro-4H-indazol-4-one;

1,6,6-trimethyl-3-propyl-1,5,6,7-tetrahydro-4H-indazol-4-one;

1-(2-hydroxyethyl)-6,6-dimethyl-3-propyl-1,5,6,7-tetrahydro-4H-indazol-4-one;

6,6-dimethyl-1-phenyl-3-propyl-1,5,6,7-tetrahydro-4H-indazol-4-one;

6,6-dimethyl-3-propyl-1-(2-pyridinyl)-1,5,6,7-tetrahydro-4H-indazol-4-one 1-(6-chloro-3-pyridazinyl)-6,6-dimethyl-3-propyl-1,5,6,7-tetrahydro-4H-indazol-4-one;

1-(3-methoxyphenyl)-6,6-dimethyl-3-propyl-1,5,6,7-tetrahydro-4H-indazol-4-one;

1-(3-chlorophenyl)-6,6-dimethyl-3-propyl-1,5,6,7-tetrahydro-4H-indazol-4-one;

1-(4-isopropylphenyl)-6,6-dimethyl-3-propyl-1,5,6,7-tetrahydro-4H-indazol-4-one;

1-(4-iodophenyl)-6,6-dimethyl-3-propyl-1,5,6,7-tetrahydro-4H-indazol-4-one;

1,6,6-trimethyl-3-tertbuty-1-1,5,6,7-tetrahydro-4H-indazol-4-one;

1-(2-hydroxyethyl)-6,6-dimethyl-3-tertbutyl-1,5,6,7-tetrahydro-4H-indazol-4-one;

6,6-dimethyl-1-phenyl-3-tertbutyl-1,5,6,7-tetrahydro-4H-indazol-4-one;

6,6-dimethyl-1-(2-pyridinyl)-3-tertbutyl-1,5,6,7-tetrahydro-4H-indazol-4-one;

1-(6-chloro-3-pyridazinyl)-6,6-dimethyl-3-tertbutyl-1,5,6,7-tetrahydro-4H-indazol-4-one;

1-(3-methoxyphenyl)-6,6-dimethyl-3-tertbutyl-1,5,6,7-tetrahydro-4H-indazol-4-one;

1-(3-chlorophenyl)-6,6-dimethyl-3-tertbutyl-1,5,6,7-tetrahydro-4H-indazol-4-one;

1-(4-isopropylphenyl)-6,6-dimethyl-3-tertbutyl-1-1,5,6,7-tetrahydro-4H-indazol-4-one;

1-(4-iodophenyl)-6,6-dimethyl-3-tertbutyl-1,5,6,7-tetrahydro-4H-indazol-4-one;

3-isobutyl-1, 6,6-trimethyl-1,5,6,7-tetrahydro-4H-indazol-4-one;

1-(2-hydroxyethyl)-3-isobutyl-6,6-dimethyl-1,5,6,7-tetrahydro-4H-indazol-4-one;

3-isobutyl-6,6-dimethyl-1-phenyl-1,5,6,7-tetrahydro-4H-indazol-4-one;

3-isobutyl-6,6-dimethyl-1-(2-pyridinyl)-1,5,6,7-tetrahydro-4H-indazol-4-one;

1-(6-chloro-3-pyridazinyl)-3-isobutyl-6,6-dimethyl-1,5,6,7-tetrahydro-4H-indazol-4-one;

3-isobutyl-1-(3-methoxyphenyl)-6,6-dimethyl-1,5,6,7-tetrahydro-4H-indazol-4-one;
1-(3-chlorophenyl)-3-isobutyl-6,6-dimethyl-1,5,6,7-tetrahydro-4H-indazol-4-one;
3-isobutyl-1-(4-isopropylphenyl)-6,6-dimethyl-1-1,5,6,7-tetrahydro-4H-indazol-4-one;
1-(4-iodophenyl)-3-isobutyl-6,6-dimethyl-1,5,6,7-tetrahydro-4H-indazol-4-one;
1,6,6-trimethyl-3-(2,4,4-trimethylpentyl)-1,5,6,7-tetrahydro-4H-indazol-4-one;
1-(2-hydroxyethyl)-6,6-dimethyl-3-(2,4,4-trimethylpentyl)-1,5,6,7-tetrahydro-4H-indazol-4-one;
6,6-dimethyl-1-phenyl-3-(2,4,4-trimethylpentyl)-1,5,6,7-tetrahydro-4H-indazol-4-one;
6,6-dimethyl-3-(2,4,4-trimethylpentyl)-1-(2-pyridinyl)-1,5,6,7-tetrahydro-4H-indazol-4-one;
1-(6-chloro-3-pyridazinyl)-6,6-dimethyl-3-(2,4,4-trimethylpentyl)-1,5,6,7-tetrahydro-4H-indazol-4-one;
1-(3-methoxyphenyl)-6,6-dimethyl-3-(2,4,4-trimethylpentyl)-1,5,6,7-tetrahydro-4H-indazol-4-one;
1-(3-chlorophenyl)-6,6-dimethyl-3-(2,4,4-trimethylpentyl)-1,5,6,7-tetrahydro-4H-indazol-4-one;
1-(4-isopropylphenyl)-6,6-dimethyl-3-(2,4,4-trimethylpentyl)-1-1,5,6,7-tetrahydro-4H-indazol-4-one;
1-(4-iodophenyl)-6,6-dimethyl-3-(2,4,4-trimethylpentyl)-1,5,6,7-tetrahydro-4H-indazol-4-one;
3-cyclopropyl-1-(2-hydroxyethyl)-5,6-dihydrocyclopenta[c]pyrazol-4(1H)-one;
3-(2-furyl)-1-(2-hydroxyethyl)-5,6-dihydrocyclopenta[c]pyrazol-4(1H)-one;
3-(isoxazol-5-yl)-1-(2-hydroxyethyl)-5,6-dihydrocyclopenta[c]pyrazol-4(1H)-one;
3-phenyl-1-(2-hydroxyethyl)-5,6-dihydrocyclopenta[c]pyrazol-4(1H)-one;
3-(thien-2-yl)-1-(2-hydroxyethyl)-5,6-dihydrocyclopenta[c]pyrazol-4(1H)-one;
3-benzyl-1-(2-hydroxyethyl)-5,6-dihydrocyclopenta[c]pyrazol-4(1H)-one;
3-(2-fluorophenyl)-1-(2-hydroxyethyl)-5,6-dihydrocyclopenta[c]pyrazol-4(1H)-one;
3-(2-thienylmethyl)-1-(2-hydroxyethyl)-5,6-dihydrocyclopenta[c]pyrazol-4(1H)-one;
3-(2-cyclopentylethyl)-1-(2-hydroxyethyl)-5,6-dihydrocyclopenta[c]pyrazol-4(1H)-one;
3-(3-methoxyphenyl)-1-(2-hydroxyethyl)-5,6-dihydrocyclopenta[c]pyrazol-4(1H)-one;
3-phenoxymethyl-1-2-(hydroxyethyl)-5,6-dihydrocyclopenta[c]pyrazol-4(1H)-one;
3-(pyrid-4-yl)-1-(2-hydroxyethyl)-5,6-dihydrocyclopenta[c]pyrazol-4(1H)-one;
3-(trans-2-phenyl-cycloprop-1-yl)-1-2-(hydroxyethyl)-5,6-dihydrocyclopenta[c]pyrazol-4(1H)-one;
3-(4-dimethylaminophenyl)-1-(2-hydroxyethyl)-5,6-dihydrocyclopenta[c]pyrazol-4(1H)-one;
3-(quinoxal-2-yl)-1-(2-hydroxyethyl)-5,6-dihydrocyclopenta[c]pyrazol-4(1H)-one;
3-(2,6-dimethoxyphenyl)-1-(2-hydroxyethyl)-5,6-dihydrocyclopenta[c]pyrazol-4(1H)-one;
3-cyclopropyl1-(2-cyanoethyl)-5,6-dihydrocyclopenta[c]pyrazol-4(1H)-one;
3-(2-furyl)-1-(2-cyanoethyl)-5,6-dihydrocyclopenta[c]pyrazol-4(1H)-one;
3-(isoxazol-5-yl)-1-(2-cyanoethyl)-5,6-dihydrocyclopenta[c]pyrazol-4(1H)-one;
3-phenyl-1-(2-cyanoethyl))-5,6-dihydrocyclopenta[c]pyrazol-4(1H)-one;
3-(thien-2-yl)-1-(2-cyanoethyl)-5,6-dihydrocyclopenta[c]pyrazol-4(1H)-one;
3-benzyl-1-(2-cyanoethyl)-5,6-dihydrocyclopenta[c]pyrazol-4(1H)-one;
3-(2-fluorophenyl)-1-(2-cyanoethyl)-5,6-dihydrocyclopenta[c]pyrazol-4(1H)-one;
3-(2-thienylmethyl)-1-(2-cyanoethyl)-5,6-dihydrocyclopenta[c]pyrazol-4(1H)-one;
3-(2-cyclopentylethyl)-1-(2-cyanoethyl)-5,6-dihydrocyclopenta[c]pyrazol-4(1H)-one;
3-(3-methoxyphenyl)-1-(2-cyanoethyl)-5,6-dihydrocyclopenta[c]pyrazol-4(1H)-one;
3-phenoxymethyl-1-(2-cyanoethyl)-5,6-dihydrocyclopenta[c]pyrazol-4(1H)-one;
3-(pyrid-4-yl)-1-(2-cyanoethyl)-5,6-dihydrocyclopenta[c]pyrazol-4(1H)-one;
3-(trans-2-phenyl-cycloprop-1-yl)-1-(2-cyanoethyl)-5,6-dihydrocyclopenta[c]pyrazol-4(1H)-one;
3-(4-dimethylaminophenyl)-1-(2-cyanoethyl)-5,6-dihydrocyclopenta[c]pyrazol-4(1H)-one;
3-(quinoxal-2-yl)-1-(2-cyanoethyl)-5,6-dihydrocyclopenta[c]pyrazol-4(1H)-one;
3-(2,6-dimethoxyphenyl)-1-(2-cyanoethyl)-5,6-dihydrocyclopenta[c]pyrazol-4(1H)-one;
3-cyclopropyl1-7,7-dimethyl-(2,2,2-trifluoroethyl)-1,5,6,7-tetrahydro-4H-indazol-4-one;
7,7-dimethyl-3-(2-furyl)-1-(2,2,2-trifluoroethyl)-1,5,6,7-tetrahydro-4H-indazol-4-one;
7,7-dimethyl-3-(isoxazol-5-yl)-1-(2,2,2-trifluoroethyl)-1,5,6,7-tetrahydro-4H-indazol-4-one;
7,7-dimethyl-3-phenyl-1-(2,2,2-trifluoroethyl)-1,5,6,7-tetrahydro-4H-indazol-4-one;
7,7-dimethyl-3-(thien-2-yl)-1-(2,2,2-trifluoroethyl)-1,5,6,7-tetrahydro-4H-indazol-4-one;
3-benzyl-7,7-dimethyl-1-(2,2,2-trifluoroethyl)-1,5,6,7-tetrahydro-4H-indazol-4-one;
7,7-dimethyl-3-(2-fluorophenyl)-1-(2,2,2-trifluoroethyl)-1,5,6,7-tetrahydro-4H-indazol-4-one;
7,7-dimethyl-3-(2-thienylmethyl)-1-(2,2,2-trifluoroethyl)-1,5,6,7-tetrahydro-4H-indazol-4-one;
3-(2-cyclopentylethyl)-7,7-dimethyl-1-(2,2,2-trifluoroethyl)-1,5,6,7-tetrahydro-4H-indazol-4-one;
7,7-dimethyl-3-(3-methoxyphenyl)-1-(2,2,2-trifluoroethyl)-1,5,6,7-tetrahydro-4H-indazol-4-one;
7,7-dimethyl-3-phenoxymethyl-1-(2,2,2-trifluoroethyl)-1,5,6,7-tetrahydro-4H-indazol-4-one;
7,7-dimethyl-3-(pyrid-4-yl)-1-(2,2,2-trifluoroethyl)-1,5,6,7-tetrahydro-4H-indazbl-4-one;
7,7-dimethyl-3-(trans-2-phenyl-cycloprop-1-yl)-1-(2,2,2-trifluoroethyl)-1,5,6,7-tetrahydro-4H-indazol-4-one;
7,7-dimethyl-3-(4-dimethylaminophenyl)-1-(2,2,2-trifluoroethyl)-1,5,6,7-tetrahydro-4H-indazol-4-one;
7,7-dimethyl-3-(quinoxal-2-yl)-1-(2,2,2-trifluoroethyl)-1,5,6,7-tetrahydro-4H-indazol-4-one;
7,7-dimethyl-3-(2,6-dimethoxyphenyl)-1-(2,2,2-trifluoroethyl)-1,5,6,7-tetrahydro-4H-indazol-4-one;
3-cyclopropyl1-5,5-dimethyl-(2,2,2-trifluoroethyl)-1,5,6,7-tetrahydro-4H-indazol-4-one;

5,5-dimethyl-3-(2-furyl)-1-(2,2,2-trifluoroethyl)-1,5,6,7-tetrahydro-4H-indazol-4-one;

5,5-dimethyl-3-(isoxazol-5-yl)-1-(2,2,2-trifluoroethyl)-1,5,6,7-tetrahydro-4H-indazol-4-one;

5,5-dimethyl-3-phenyl-1-(2,2,2-trifluoroethyl)-1,5,6,7-tetrahydro-4H-indazol-4-one;

5,5-dimethyl-3-(thien-2-yl)-1-(2,2,2-trifluoroethyl)-1,5,6,7-tetrahydro-4H-indazol-4-one;

3-benzyl-5,5-dimethyl-1-(2,2,2-trifluoroethyl)-1,5,6,7-tetrahydro-4H-indazol-4-one;

5,5-dimethyl-3-(2-fluorophenyl)-1-(2,2,2-trifluoroethyl)-1,5,6,7-tetrahydro-4H-indazol-4-one;

5,5-dimethyl-3-(2-thienylmethyl)-1-(2,2,2-trifluoroethyl)-1,5,6,7-tetrahydro-4H-indazol-4-one;

3-(2-cyclopentylethyl)-5,5-dimethyl-1-(2,2,2-trifluoroethyl)-1,5,6,7-tetrahydro-4H-indazol-4-one;

5,5-dimethyl-3-(3-methoxyphenyl)-1-(2,2,2-trifluoroethyl)-1,5,6,7-tetrahydro-4H-indazol-4-one;

5,5-dimethyl-3-phenoxymethyl-1-(2,2,2-trifluoroethyl)-1,5,6,7-tetrahydro-4H-indazol-4-one;

5,5-dimethyl-3-(pyrid-4-yl)-1-(2,2,2-trifluoroethyl)-1,5,6,7-tetrahydro-4H-indazol-4-one;

5,5-dimethyl-3-(trans-2-phenyl-cycloprop-1-yl)-1-(2,2,2-trifluoroethyl)-1,5,6,7-tetrahydro-4H-indazol-4-one;

5,5-dimethyl-3-(4-dimethylaminophenyl)-1-(2,2,2-trifluoroethyl)-1,5,6,7-tetrahydro-4H-indazol-4-one;

5,5-dimethyl-3-(quinoxal-2-yl)-1-(2,2,2-trifluoroethyl)-1,5,6,7-tetrahydro-4H-indazol-4-one;

5,5-dimethyl-3-(2,6-dimethoxyphenyl)-1-(2,2,2-trifluoroethyl)-1,5,6,7-tetrahydro-4H-indazol-4-one;

1-(3-chloropyridazin-6-yl)-3-cyclopropyl1-7,7-dimethyl-1,5,6,7-tetrahydro-4H-indazol-4-one;

1-(3-chloropyridazin-6-yl)-7,7-dimethyl-3-(2-furyl)-1,5,6,7-tetrahydro-4H-indazol-4-one;

1-(3-chloropyridazin-6-yl)-7,7-dimethyl-3-(isoxazol-5-yl)-1,5,6,7-tetrahydro-4H-indazol-4-one;

1-(3-chloropyridazin-6-yl)-7,7-dimethyl-3-phenyl-1,5,6,7-tetrahydro-4H-indazol-4-one;

1-(3-chloropyridazin-6-yl)-7,7-dimethyl-3-(thien-2-yl)-1,5,6,7-tetrahydro-4H-indazol-4-one;

3-benzyl-1-(3-chloropyridazin-6-yl)-7,7-dimethyl-1,5,6,7-tetrahydro-4H-indazol-4-one;

1-(3-chloropyridazin-6-yl)-7,7-dimethyl-3-(2-fluorophenyl)-1,5,6,7-tetrahydro-4H-indazol-4-one;

1-(3-chloropyridazin-6-yl)-7,7-dimethyl-3-(2-thienylmethyl)-1,5,6,7-tetrahydro-4H-indazol-4-one;

1-(3-chloropyridazin-6-yl)-3-(2-cyclopentylethyl)-7,7-dimethyl-1,5,6,7-tetrahydro-4H-indazol-4-one;

1-(3-chloropyridazin-6-yl)-7,7-dimethyl-3-(3-methoxyphenyl)-1,5,6,7-tetrahydro-4H-indazol-4-one;

1-(3-chloropyridazin-6-yl)-7,7-dimethyl-3-phenoxymethyl-1,5,6,7-tetrahydro-4H-indazol-4-one;

1-(3-chloropyridazin-6-yl)-7,7-dimethyl-3-(pyrid-4-yl)-1,5,6,7-tetrahydro-4H-indazol-4-one;

1-(3-chloropyridazin-6-yl)-7,7-dimethyl-3-(trans-2-phenyl-cycloprop-1-yl)-1,5,6,7-tetrahydro-4H-indazol-4-one;

1-(3-chloropyridazin-6-yl)-7,7-dimethyl-3-(4-dimethylaminophenyl)-1,5,6,7-tetrahydro-4H-indazol-4-one;

1-(3-chloropyridazin-6-yl)-7,7-dimethyl-3-(quinoxal-2-yl)-1,5,6,7-tetrahydro-4H-indazol-4-one;

1-(3-chloropyridazin-6-yl)-7,7-dimethyl-3-(2,6-dimethoxyphenyl)-1,5,6,7-tetrahydro-4H-indazol-4-one;

1-(3-chloropyridazin-6-yl)-3-cyclopropyl1-5,5-dimethyl-1,5,6,7-tetrahydro-4H-indazol-4-one;

1-(3-chloropyridazin-6-yl)-5,5-dimethyl-3-(2-furyl)-1,5,6,7-tetrahydro-4H-indazol-4-one;

1-(3-chloropyridazin-6-yl)-5,5-dimethyl-3-(isoxazol-5-yl)-1,5,6,7-tetrahydro-4H-indazol-4-one;

1-(3-chloropyridazin-6-yl)-5,5-dimethyl-3-phenyl-1,5,6,7-tetrahydro-4H-indazol-4-one;

1-(3-chloropyridazin-6-yl)-5,5-dimethyl-3-(thien-2-yl)-1,5,6,7-tetrahydro-4H-indazol-4-one;

3-benzyl-1-(3-chloropyridazin-6-yl)-5,5-dimethyl-1,5,6,7-tetrahydro-4H-indazol-4-one;

1-(3-chloropyridazin-6-yl)-5,5-dimethyl-3-(2-fluorophenyl)-1,5,6,7-tetrahydro-4H-indazol-4-one;

1-(3-chloropyridazin-6-yl)-5,5-dimethyl-3-(2-thienylmethyl)-1,5,6,7-tetrahydro-4H-indazol-4-one;

1-(3-chloropyridazin-6-yl)-3-(2-cyclopentylethyl)-5,5-dimethyl-1,5,6,7-tetrahydro-4H-indazol-4-one;

1-(3-chloropyridazin-6-yl)-5,5-dimethyl-3-(3-methoxyphenyl)-1,5,6,7-tetrahydro-4H-indazol-4-one;

1-(3-chloropyridazin-6-yl)-5,5-dimethyl-3-phenoxymethyl-1,5,6,7-tetrahydro-4H-indazol-4-one;

1-(3-chloropyridazin-6-yl)-5,5-dimethyl-3-(pyrid-4-yl)-1,5,6,7-tetrahydro-4H-indazol-4-one;

1-(3-chloropyridazin-6-yl)-5,5-dimethyl-3-(trans-2-phenylcycloprop-1-yl)-1,5,6,7-tetrahydro-4H-indazol-4-one;

1-(3-chloropyridazin-6yl)-5,5-dimethyl-3-(4-dimethylaminophenyl)-1,5,6,7-tetrahydro-4H-indazol-4-one;

1-(3-chloropyridazin-6-yl)-5,5-dimethyl-3-(quinoxal-2-yl)-1,5,6,7-tetrahydro-4H-indazol-4-one;

1-(3-chloropyridazin-6-yl)-5,5-dimethyl-3-(2,6-dimethoxyphenyl)-1,5,6,7-tetrahydro-4H-indazol-4-one;

1-(benzothiazol-2-yl)-7-cyano-3-cyclopropyl1-6,6-dimethyl-1,5,6,7-tetrahydro-4H-indazol-4-one;

1-(benzothiazol-2-yl)-7-cyano-6,6-dimethyl-3-(2-furyl)-1,5,6,7-tetrahydro-4H-indazol-4-one;

1-(benzothiazol-2-yl)-7-cyano-6,6-dimethyl-3-(isoxazol-5-yl)-1,5,6,7-tetrahydro-4H-indazol-4-one;

1-(benzothiazol-2-yl)-7-cyano-6,6-dimethyl-3-phenyl-1,5,6,7-tetrahydro-4H-indazol-4-one;

1-(benzothiazol-2-yl)-7-cyano-6,6-dimethyl-3-(thien-2-yl)-1,5,6,7-tetrahydro-4H-indazol-4-one;

1-(benzothiazol-2-yl)-3-benzyl-7-cyano-6,6-dimethyl-1,5,6,7-tetrahydro-4H-indazol-4-one;

1-(benzothiazol-2-yl)-7-cyano-6,6-dimethyl-3-(2-fluorophenyl)-1,5,6,7-tetrahydro-4H-indazol-4-one;

1-(benzothiazol-2-yl)-7-cyano-6,6-dimethyl-3-(2-thienylmethyl)-1,5,6,7-tetrahydro-4H-indazol-4-one;

1-(benzothiazol-2yl)-7-cyano-3-(2-cyclopentylethyl)-6,6-dimethyl-1,5,6,7-tetrahydro-4H-indazol-4-one;

1-(benzothiazol-2-yl)-7-cyano-6,6-dimethyl-3-(3-methoxyphenyl)-1,5,6,7-tetrahydro-4H-indazol-4-one;

1-(benzothiazol-2-yl)-7-cyano-6,6-dimethyl-3-phenoxymethyl-1,5,6,7-tetrahydro-4H-indazol-4-one;

1-(benzothiazol-2-yl)-7-cyano-6,6-dimethyl-3-(pyrid-4-yl)-1,5,6,7-tetrahydro-4H-indazol-4-one;

1-(benzothiazol-2-yl)-7-cyano-6,6-dimethyl-3-(trans-2-phenyl-cycloprop-1-yl)-1,5,6,7-tetrahydro-4H-indazol-4-one;

1-(benzothiazol-2-yl)-7-cyano-6,6-dimethyl-3-(4-dimethylaminophenyl)-1,5,6,7-tetrahydro-4H-indazol-4-one;

1-(benzothiazol-2-yl)-7-cyano-6,6-dimethyl-3-(quinoxal-2-yl)-1,5,6,7-tetrahydro-4H-indazol-4-one;

1-(benzothiazol-2-yl)-7-cyano-6,6-dimethyl-3-(2,6-dimethoxyphenyl)-1,5,6,7-tetrahydro-4H-indazol-4-one;

1-(benzothiazol-2-yl)-5-cyano-3-cyclopropyl1-6,6-dimethyl-1,5,6,7-tetrahydro-4H-indazol-4-one;

1-(benzothiazol-2-yl)-5-cyano-6,6-dimethyl-3-(2-furyl)-1,5,6,7-tetrahydro-4H-indazol-4-one;

1-(benzothiazol-2-yl)-5-cyano-6,6-dimethyl-3-(isoxazol-5-yl)-1,5,6,7-tetrahydro-4H-indazol-4-one;

1-(benzothiazol-2-yl)-5-cyano-6,6-dimethyl-3-phenyl-1,5,6,7-tetrahydro-4H-indazol-4-one;

1-(benzothiazol-2-yl)-5-cyano-6,6-dimethyl-3-(thien-2-yl)-1,5,6,7-tetrahydro-4H-indazol-4-one;

1-(benzothiazol-2-yl)-3-benzyl-5-cyano-6,6-dimethyl-1,5,6,7-tetrahydro-4H-indazol-4-one;

1-(benzothiazol-2-yl)-5-cyano-6,6-dimethyl-3-(2-fluorophenyl)-1,5,6,7-tetrahydro-4H-indazol-4-one;

1-(benzothiazol-2-yl)-5-cyano-6,6-dimethyl-3-(2-thienylmethyl)-1,5,6,7-tetrahydro-4H-indazol-4-one;

1-(benzothiazol-2yl)-5-cyano-3-(2-cyclopentylethyl)-6,6-dimethyl-1,5,6,7-tetrahydro-4H-indazol-4-one;

1-(benzothiazol-2-yl)-5-cyano-6,6-dimethyl-3-(3-methoxyphenyl)-1,5,6,7-tetrahydro-4H-indazol-4-one;

1-(benzothiazol-2-yl)-5-cyano-6,6-dimethyl-3-phenoxymethyl-1,5,6,7-tetrahydro-4H-indazol-4-one;

1-(benzothiazol-2-yl)-5-cyano-6,6-dimethyl-3-(pyrid-4-yl)-1,5,6,7-tetrahydro-4H-indazol-4-one;

1-(benzothiazol-2-yl)-5-cyano-6,6-dimethyl-3-(trans-2-phenyl-cycloprop-1-yl)-1,5,6,7-tetrahydro-4H-indazol-4-one;

1-(benzothiazol-2-yl)-5-cyano-6,6-dimethyl-3-(4-dimethylaminophenyl)-1,5,6,7-tetrahydro-4H-indazol-4-one;

1-(benzothiazol-2-yl)-5-cyano-6,6-dimethyl-3-(quinoxal-2-yl)-1,5,6,7-tetrahydro-4H-indazol-4-one;

1-(benzothiazol-2-yl)-5-cyano-6,6-dimethyl-3-(2,6-dimethoxyphenyl)-1,5,6,7-tetrahydro-4H-indazol-4-one;

7-cyano-3-cyclopropyl1-6,6-dimethyl-1-(4-isopropylphenyl)-1,5,6,7-tetrahydro-4H-indazol-4-one;

7-cyano-6,6-dimethyl-3-(2-furyl)-1-(4-isopropylphenyl)-1,5,6,7-tetrahydro-4H-indazol-4-one;

7-cyano-6,6-dimethyl-1-(4-isopropylphenyl)-3-(isoxazol-5-yl)-1,5,6,7-tetrahydro-4H-indazol-4-one;

7-cyano-6,6-dimethyl-1-(4-isopropylphenyl)-3-phenyl-1,5,6,7-tetrahydro-4H-indazol-4-one;

7-cyano-6,6-dimethyl-1-(4-isopropylphenyl)-3-(thien-2-yl)-1,5,6,7-tetrahydro-4H-indazol-4-one;

3-benzyl-7-cyano-6,6-dimethyl-1-(4-isopropylphenyl)-1,5,6,7-tetrahydro-4H-indazol-4-one;

7-cyano-6,6-dimethyl-3-(2-fluorophenyl)-1-(4-isopropylphenyl)-1,5,6,7-tetrahydro-4H-indazol-4-one;

7-cyano-6,6-dimethyl-1-(4-isopropylphenyl)-3-(2-thienylmethyl)-1,5,6,7-tetrahydro-4H-indazol-4-one;

7-cyano-3-(2-cyclopentylethyl)-6,6-dimethyl-1-(4-isopropylphenyl)-1,5,6,7-tetrahydro-4H-indazol-4one;

7-cyano-6,6-dimethyl-1-(4-isopropylphenyl)-3-(3-methoxyphenyl)-1,5,6,7-tetrahydro-4H-indazol-4-one;

7-cyano-6,6-dimethyl-1-(4-isopropylphenyl)-3-phenoxymethyl-1,5,6,7-tetrahydro-4H-indazol-4-one;

7-cyano-6,6-dimethyl-1-(4-isopropylphenyl)-3-(pyrid-4-yl)-1,5,6,7-tetrahydro-4H-indazol-4-one;

7-cyano-6,6-dimethyl-1-(4-isopropylphenyl)-3-(trans-2-phenyl-cycloprop-1-yl)-1,5,6,7-tetrahydro-4H-indazol-4-one;

7-cyano-6,6-dimethyl-3-(4-dimethylaminophenyl)-1-(4-isopropylphenyl)-1,5,6,7-tetrahydro-4H-indazol-4-one;

7-cyano-6,6-dimethyl-1-(4-isopropylphenyl)-3-(quinoxal-2-yl)-1,5,6,7-tetrahydro-4H-indazol-4-one;

7-cyano-6,6-dimethyl-3-(2,6-dimethoxyphenyl)-1-(4-isopropylphenyl)-1,5,6,7-tetrahydro-4H-indazol-4-one;

5-cyano-3-cyclopropyl1-6,6-dimethyl-1-(4-isopropylphenyl)-1,5,6,7-tetrahydro-4H-indazol-4-one;

5-cyano-6,6-dimethyl-3-(2-furyl)-1-(4-isopropylphenyl)-1,5,6,7-tetrahydro-4H-indazol-4-one;

5-cyano-6,6-dimethyl-1-(4-isopropylphenyl)-3-(isoxazol-5-yl)-1,5,6,7-tetrahydro-4H-indazol-4-one;

5-cyano-6,6-dimethyl-1-(4-isopropylphenyl)-3-phenyl-1,5,6,7-tetrahydro-4H-indazol-4-one;

5-cyano-6,6-dimethyl-1-(4-isopropylphenyl)-3-(thien-2-yl)-1,5,6,7-tetrahydro-4H-indazol-4-one;

3-benzyl-5-cyano-6,6-dimethyl-1-(4-isopropylphenyl)-1,5,6,7-tetrahydro-4H-indazol-4-one;

5-cyano-6,6-dimethyl-3-(2-fluorophenyl)-1-(4-isopropylphenyl)-1,5,6,7-tetrahydro-4H-indazol-4-one;

5-cyano-6,6-dimethyl-1-(4-isopropylphenyl)-3-(2-thienylmethyl)-1,5,6,7-tetrahydro-4H-indazol-4-one;

5-cyano-3-(2-cyclopentylethyl)-6,6-dimethyl-1-(4-isopropylphenyl)-1,5,6,7-tetrahydro-4H-indazol-4one;

5-cyano-6,6-dimethyl-1-(4-isopropylphenyl)-3-(3-methoxyphenyl)-1,5,6,7-tetrahydro-4H-indazol-4-one;

5-cyano-6,6-dimethyl-1-(4-isopropylphenyl)-3-phenoxymethyl-1,5,6,7-tetrahydro-4H-indazol-4-one;

5-cyano-6,6-dimethyl-1-(4-isopropylphenyl)-3-(pyrid-4-yl)-1,5,6,7-tetrahydro-4H-indazol-4-one;

5-cyano-6,6-dimethyl-1-(4-isopropylphenyl)-3-(trans-2-phenyl-cycloprop-1-yl)-1,5,6,7-tetrahydro-4H-indazol-4-one;

5-cyano-6,6-dimethyl-3-(4-dimethylaminophenyl)-1-(4-isopropylphenyl)-1,5,6,7-tetrahydro-4H-indazol-4-one;

5-cyano-6,6-dimethyl-1-(4-isopropylphenyl)-3-(quinoxal-2-yl)-1,5,6,7-tetrahydro-4H-indazol-4-one;

5-cyano-6,6-dimethyl-3-(2,6-dimethoxyphenyl)-1-(4-isopropylphenyl)-1,5,6,7-tetrahydro-4H-indazol-4-one;

3-cyclopropyl1-1-(4-iodophenyl)-8-methyl-1,5,5a,6,7,8,9,9a-octahydro-4H-pyrazolo[4,3-h]isoquinolin-4-one;

3-(2-furyl)-1-(4-iodophenyl)-8-methyl-1,5,5a,6,7,8,9,9a-octahydro-4H-pyrazolo[4,3-h]isoquinolin-4-one;

1-(4-iodophenyl)-3-(isoxazol-5-yl)-8-methyl-1,5,5a,6,7,8,9,9a-octahydro-4H-pyrazolo[4,3-h]isoquinolin-4-one;

1-(4-iodophenyl)-8-methyl-3-phenyl-1,5,5a,6,7,8,9,9a-octahydro-4H-pyrazolo[4,3-h]isoquinolin-4-one;

1-(4-iodophenyl)-8-methyl-3-(thien-2-yl)-1,5,5a,6,7,8,9,9a-octahydro-4H-pyrazolo[4,3-h]isoquinolin-4-one;

3-benzyl-1-(4-iodophenyl)-8-methyl-1,5,5a,6,7,8,9,9a-octahydro-4H-pyrazolo[4,3-h]isoquinolin-4-one;

3-(2-fluorophenyl)-1-(4-iodophenyl)-8-methyl-1,5,5a,6,7,8,9,9a-octahydro-4H-pyrazolo[4,3-h]isoquinolin-4-one;

1-(4-iodophenyl)-8-methyl-3-(2-thienylmethyl)-1,5,5a,6,7,8,9,9a-octahydro-4H-pyrazolo[4,3-h]isoquinolin-4-one;

3-(2-cyclopentylethyl)-1-(4-iodophenyl)-8-methyl-1,5,5a,6,7,8,9,9a-octahydro-4H-pyrazolo[4,3-h]isoquinolin-4-one;

1-(4-iodophenyl)-3-(3-methoxyphenyl)-8-methyl-1,5,5a,6,7,8,9,9a-octahydro-4H-pyrazolo[4,3-h]isoquinolin-4-one;

1-(4-iodophenyl)-8-methyl-3-phenoxymethyl-1,5,5a,6,7,8,9,9a-octahydro-4H-pyrazolo[4,3-h]isoquinolin-4-one;

1-(4-iodophenyl)-8-methyl-3-(pyrid-4-yl)-1,5,5a,6,7,8,9,9a-octahydro-4H-pyrazolo[4,3-h]isoquinolin-4-one;

1-(4-iodophenyl)-8-methyl-3-(trans-2-phenyl-cycloprop-1-yl)-1,5,5a,6,7,8,9,9a-octahydro-4H-pyrazolo[4,3-h]isoquinolin-4-one;

3-(4-dimethylaminophenyl)-1-(4-iodophenyl)-8-methyl-1,5,5a,6,7,8,9,9a-octahydro-4H-pyrazolo[4,3-h]isoquinolin-4-one;

1-(4-iodophenyl)-8-methyl-3-(quinoxal-2-yl)-1,5,5a,6,7,8,9,9a-octahydro-4H-pyrazolo[4,3-h]isoquinolin-4-one;

3-(2,6-dimethoxyphenyl)-1-(4-iodophenyl)-8-methyl-1,5,5a,6,7,8,9,9a-octahydro-4H-pyrazolo[4,3-h]isoquinolin-4-one;

3-cyclopropyl-1-(4-iodophenyl)-6-methyl-1,4a,5,6,7,8,8a,9-octahydro-4H-pyrazolo[3,4-g]isoquinolin-4-one;

3-(2-furyl)-1-(4-iodophenyl)-6-methyl-1,4a,5,6,7,8,8a,9-octahydro-4H-pyrazolo[3,4-g]isoquinolin-4one;

1-(4-iodophenyl)-3-(isoxazol-5-yl)-6-methyl-1,4a,5,6,7,8,8a,9-octahydro-4H-pyrazolo[3,4-g]isoquinolin-4-one;

1-(4-iodophenyl)-6-methyl-3-phenyl-1,4a,5,6,7,8,8a,9-octahydro-4H-pyrazolo[3,4-g]isoquinolin-4-one;

1-(4-iodophenyl)-6-methyl-3-(thien-2-yl)-1,4a,5,6,7,8,8a,9-octahydro-4H-pyrazolo[3,4-g]isoquinolin-4-one;

3-benzyl-1-(4-iodophenyl)-6-methyl-1,4a,5,6,7,8,8a,9-octahydro-4H-pyrazolo[3,4-g]isoquinolin-4-one;

3-(2-fluorophenyl)-1-(4-iodophenyl)-6-methyl-1,4a,5,6,7,8,8a,9-octahydro-4H-pyrazolo[3,4-g]isoquinolin-4-one;

1-(4-iodophenyl)-6-methyl-3-(2-thienylmethyl)-1,4a,5,6,7,8,8a,9-octahydro-4H-pyrazolo[3,4-g]isoquinolin-4-one;

3-(2-cyclopentylethyl)-1-(4-iodophenyl)-6-methyl-1,4a,5,6,7,8,8a,9-octahydro-4H-pyrazolo[3,4-g]isoquinolin-4-one;

1-(4-iodophenyl)-3-(3-methoxyphenyl)-6-methyl-1,4a,5,6,7,8,8a,9-octahydro-4H-pyrazolo[3,4-g]isoquinolin-4-one;

1-(4-iodophenyl)-6-methyl-3-phenoxymethyl-1,4a,5,6,7,8,8a,9-octahydro-4H-pyrazolo[3,4-g]isoquinolin-4-one;

1-(4-iodophenyl)-6-methyl-3-(pyrid-4-yl)-1,4a,5,6,7,8,8a,9-octahydro-4H-pyrazolo[3,4-g]isoquinolin-4-one;

1-(4-iodophenyl)-6-methyl-3-(trans-2-phenyl-cycloprop-1-yl)-1,4a,5,6,7,8,8a,9-octahydro-4H-pyrazolo[3,4-g]isoquinolin-4-one;

3-(4-dimethylaminophenyl)-1-(4-iodophenyl)-6-methyl-1,4a,5,6,7,8,8a,9-octahydro-4H-pyrazolo[3,4-g]isoquinolin-4-one;

1-(4-iodophenyl)-6-methyl-3-(quinoxal-2-yl)-1,4a,5,6,7,8,8a,9-octahydro-4H-pyrazolo[3,4-g]isoquinolin-4-one;

3-(2,6-dimethoxyphenyl)-1-(4-iodophenyl)-6-methyl-1,4a,5,6,7,8,8a,9-octahydro-4H-pyrazolo[3,4-g]isoquinolin-4-one;

1-(7-chloro-quinolin-4-yl)-3-cyclopropyl-indeno[1,2-c]pyrazol-4(1H)-one;

1-(7-chloro-quinolin-4-yl)-3-(2-furyl)-indeno[1,2-c]pyrazol-4(1H)-one;

1-(7-chloro-quinolin-4-yl)-3-(isoxazol-5-yl)-indeno[1,2-c]pyrazol-4(1H)-one;

1-(7-chloro-quinolin-4-yl)-3-phenyl-indeno[1,2-c]pyrazol-4(1H)-one;

1-(7-chloro-quinolin-4-yl)-3-(thien-2-yl)-indeno[1,2-c]pyrazol-4(1H)-one;

3-benzyl-1-(7-chloro-quinolin-4-yl)-indeno[1,2-c]pyrazol-4(1H)-one;

1-(7-chloro-quinolin-4-yl)-3-(2-fluorophenyl)-indeno[1,2-c]pyrazol-4(1H)-one;

1-(7-chloro-quinolin-4-yl)-3-(2-thienylmethyl)-indeno[1,2-c]pyrazol-4(1H)-one;

1-(7-chloro-quinolin-4-yl)-3-(2-cyclopentylethyl)-indeno[1,2-c]pyrazol-4(1H)-one;

1-(7-chloro-quinolin-4-yl)-3-(3-methoxyphenyl)-indeno[1,2-c]pyrazol-4(1H)-one;

1-(7-chloro-quinolin-4-yl)-3-phenoxymethyl-indeno[1,2-c]pyrazol-4(1H)-one 1-(7-chloro-quinolin-4-yl)-3-(pyrid-4-yl)-indeno[1,2-c]pyrazol-4(1H)-one;

1-(7-chloro-quinolin-4-yl)-3-(trans-2-phenyl-cycloprop-1-yl)-indeno[1,2-c]pyrazol-4(1H)-one;

1-(7-chloro-quinolin-4-yl)-3-(4-dimethylaminophenyl)-indeno[1,2-c]pyrazol-4(1H)-one;

1-(7-chloro-quinolin-4-yl)-3-(quinoxal-2-yl)-indeno[1,2-c]pyrazol-4(1H)-one and 1-(7-chloro-quinolin-4-yl)-3-(2,6-dimethoxyphenyl)-indeno[1,2-c]pyrazol-4(1H)-one.

3-cyclopropyl-1-(2-hydroxyethyl)-5,6-dihydrocyclopenta[c]pyrazol-4(1H)-one;

3-(2-furyl)-1-(2-hydroxyethyl)-5,6-dihydrocyclopenta[c]pyrazol-4(1H)-one;

3-(isoxazol-5-yl)-1-(2-hydroxyethyl)-5,6-dihydrocyclopenta[c]pyrazol-4(1H)-one;

3-phenyl-1-(2-hydroxyethyl)-5,6-dihydrocyclopenta[c]pyrazol-4(1H)-one;

3-(thien-2-yl)-1-(2-hydroxyethyl)-5,6-dihydrocyclopenta[c]pyrazol-4(1H)-one;

3-benzyl-1-(2-hydroxyethyl)-5,6-dihydrocyclopenta[c]pyrazol-4(1H)-one;

3-(2-fluorophenyl)-1-(2-hydroxyethyl)-5,6-dihydrocyclopenta[c]pyrazol-4(1H)-one;

3-(2-thienylmethyl)-1-(2-hydroxyethyl)-5,6-dihydrocyclopenta[c]pyrazol-4(1H)-one;
3-(2-cyclopentylethyl)-1-(2-hydroxyethyl)-5,6-dihydrocyclopenta[c]pyrazol-4(1H)-one;
3-(3-methoxyphenyl)-1-(2-hydroxyethyl)-5,6-dihydrocyclopenta[c]pyrazol-4(1H)-one;
3-phenoxymethyl-1-2-(hydroxyethyl)-5,6-dihydrocyclopenta[c]pyrazol-4(1H)-one;
3-(pyrid-4-yl)-1-(2-hydroxyethyl)-5,6-dihydrocyclopenta[c]pyrazol-4(1H)-one;
3-(trans-2-phenyl-cycloprop-1-yl)-1-2-(hydroxyethyl)-5,6-dihydrocyclopenta[c]pyrazol-4(1H)-one;
3-(4-dimethylaminophenyl)-1-(2-hydroxyethyl)-5,6-dihydrocyclopenta[c]pyrazol-4(1H)-one;
3-(quinoxal-2-yl)-1-(2-hydroxyethyl)-5,6-dihydrocyclopenta[c]pyrazol-4(1H)-one;
3-(2,6-dimethoxyphenyl)-1-(2-hydroxyethyl)-5,6-dihydrocyclopenta[c]pyrazol-4(1H)-one;
3-cyclopropyl1-(2-cyanoethyl)-5,6-dihydrocyclopenta[c]pyrazol-4(1H)-one;
3-(2-furyl)-1-(2-cyanoethyl)-5,6-dihydrocyclopenta[c]pyrazol-4(1H)-one;
3-(isoxazol-5-yl)-1-(2-cyanoethyl)-5,6-dihydrocyclopenta[c]pyrazol-4(1H)-one;
3-phenyl-1-(2-cyanoethyl))-5,6-dihydrocyclopenta[c]pyrazol-4(1H)-one;
3-(thien-2-yl)-1-(2-cyanoethyl)-5,6-dihydrocyclopenta[c]pyrazol-4(1H)-one;
3-benzyl-1-(2-cyanoethyl)-5,6-dihydrocyclopenta[c]pyrazol-4(1H)-one;
3-(2-fluorophenyl)-1-(2-cyanoethyl)-5,6-dihydrocyclopenta[c]pyrazol-4(1H)-one;
3-(2-thienylmethyl)-1-(2-cyanoethyl)-5,6-dihydrocyclopenta[c]pyrazol-4(1H)-one;
3-(2-cyclopentylethyl)-1-(2-cyanoethyl)-5,6-dihydrocyclopenta[c]pyrazol-4(1H)-one;
3-(3-methoxyphenyl)-1-(2-cyanoethyl)-5,6-dihydrocyclopenta[c]pyrazol-4(1H)-one;
3-phenoxymethyl-1-(2-cyanoethyl)-5,6-dihydrocyclopenta[c]pyrazol-4(1H)-one;
3-(pyrid-4-yl)-1-(2-cyanoethyl)-5,6-dihydrocyclopenta[c]pyrazol-4(1H)-one;
3-(trans-2-phenyl-cycloprop-1-yl)-1-(2-cyanoethyl)-5,6-dihydrocyclopenta[c]pyrazol-4(1H)-one;
3-(4-dimethylaminophenyl)-1-(2-cyanoethyl)-5,6-dihydrocyclopenta[c]pyrazol-4(1H)-one;
3-(quinoxal-2-yl)-1-(2-cyanoethyl)-5,6-dihydrocyclopenta[c]pyrazol-4(1H)-one;
3-(2,6-dimethoxyphenyl)-1-(2-cyanoethyl)-5,6-dihydrocyclopenta[c]pyrazol-4(1H)-one;
3-cyclopropyl1-7,7-dimethyl-(2,2,2-trifluoroethyl)-1,5,6,7-tetrahydro-4H-indazol-4-one;
7,7-dimethyl-3-(2-furyl)-1-(2,2,2-trifluoroethyl)-1,5,6,7-tetrahydro-4H-indazol-4-one;
7,7-dimethyl-3-(isoxazol-5-yl)-1-(2,2,2-trifluoroethyl)-1,5,6,7-tetrahydro-4H-indazol-4-one;
7,7-dimethyl-3-phenyl-1-(2,2,2-trifluoroethyl)-1,5,6,7-tetrahydro-4H-indazol-4-one;
7,7-dimethyl-3-(thien-2-yl)-1-(2,2,2-trifluoroethyl)-1,5,6,7-tetrahydro-4H-indazol-4-one;
3-benzyl-7,7-dimethyl-1-(2,2,2-trifluoroethyl)-1,5,6,7-tetrahydro-4H-indazol-4-one;
7,7-dimethyl-3-(2-fluorophenyl)-1-(2,2,2-trifluoroethyl)-1,5,6,7-tetrahydro-4H-indazol-4-one;
7,7-dimethyl-3-(2-thienylmethyl)-1-(2,2,2-trifluoroethyl)-1,5,6,7-tetrahydro-4H-indazol-4-one;
3-(2-cyclopentylethyl)-7,7-dimethyl-1-(2,2,2-trifluoroethyl)-1,5,6,7-tetrahydro-4H-indazol-4-one;
7,7-dimethyl-3-(3-methoxyphenyl)-1-(2,2,2-trifluoroethyl)-1,5,6,7-tetrahydro-4H-indazol-4-one;
7,7-dimethyl-3-phenoxymethyl-1-(2,2,2-trifluoroethyl)-1,5,6,7-tetrahydro-4H-indazol-4-one;
7,7-dimethyl-3-(pyrid-4-yl)-1-(2,2,2-trifluoroethyl)-1,5,6,7-tetrahydro-4H-indazol-4-one;
7,7-dimethyl-3-(trans-2-phenyl-cycloprop-1-yl)-1-(2,2,2-trifluoroethyl)-1,5,6,7-tetrahydro-4H-indazol-4-one;
7,7-dimethyl-3-(4-dimethylaminophenyl)-1-(2,2,2-trifluoroethyl)-1,5,6,7-tetrahydro-4H-indazol-4-one;
7,7-dimethyl-3-(quinoxal-2-yl)-1-(2,2,2-trifluoroethyl)-1,5,6,7-tetrahydro-4H-indazol-4-one;
7,7-dimethyl-3-(2,6-dimethoxyphenyl)-1-(2,2,2-trifluoroethyl)-1,5,6,7-tetrahydro-4H-indazol-4-one;
3-cyclopropyl1-5,5-dimethyl-(2,2,2-trifluoroethyl)-1,5,6,7-tetrahydro-4H-indazol-4-one;
5,5-dimethyl-3-(2-furyl)-1-(2,2,2-trifluoroethyl)-1,5,6,7-tetrahydro-4H-indazol-4-one;
5,5-dimethyl-3-(isoxazol-5-yl)-1-(2,2,2-trifluoroethyl)-1,5,6,7-tetrahydro-4H-indazol-4-one;
5,5-dimethyl-3-phenyl-1-(2,2,2-trifluoroethyl)-1,5,6,7-tetrahydro-4H-indazol-4-one;
5,5-dimethyl-3-(thien-2-yl)-1-(2,2,2-trifluoroethyl)-1,5,6,7-tetrahydro-4H-indazol-4-one;
3-benzyl-5,5-dimethyl-1-(2,2,2-trifluoroethyl)-1,5,6,7-tetrahydro-4H-indazol-4-one;
5,5-dimethyl-3-(2-fluorophenyl)-1-(2,2,2-trifluoroethyl)-1,5,6,7-tetrahydro-4H-indazol-4-one;
5,5-dimethyl-3-(2-thienylmethyl)-1-(2,2,2-trifluoroethyl)-1,5,6,7-tetrahydro-4H-indazol-4-one;
3-(2-cyclopentylethyl)-5,5-dimethyl-1-(2,2,2-trifluoroethyl)-1,5,6,7-tetrahydro-4H-indazol-4-one;
5,5-dimethyl-3-(3-methoxyphenyl)-1-(2,2,2-trifluoroethyl)-1,5,6,7-tetrahydro-4H-indazol-4-one;
5,5-dimethyl-3-phenoxymethyl-1-(2,2,2-trifluoroethyl)-1,5,6,7-tetrahydro-4H-indazol-4-one;
5,5-dimethyl-3-(pyrid-4-yl)-1-(2,2,2-trifluoroethyl)-1,5,6,7-tetrahydro-4H-indazol-4-one;
5,5-dimethyl-3-(trans-2-phenyl-cycloprop-1-yl)-1-(2,2,2-trifluoroethyl)-1,5,6,7-tetrahydro-4H-indazol-4-one;
5,5-dimethyl-3-(4-dimethylaminophenyl)-1-(2,2,2-trifluoroethyl)-1,5,6,7-tetrahydro-4H-indazol-4-one;
5,5-dimethyl-3-(quinoxal-2-yl)-1-(2,2,2-trifluoroethyl)-1,5,6,7-tetrahydro-4H-indazol-4-one;
5,5-dimethyl-3-(2,6-dimethoxyphenyl)-1-(2,2,2-trifluoroethyl)-1,5,6,7-tetrahydro-4H-indazol-4-one;
1-(3-chloropyridazin-6-yl)-3-cyclopropyl1-7,7-dimethyl-1,5,6,7-tetrahydro-4H-indazol-4-one;
1-(3-chloropyridazin-6-yl)-7,7-dimethyl-3-(2-furyl)-1,5,6,7-tetrahydro-4H-indazol-4-one;
1-(3-chloropyridazin-6-yl)-7,7-dimethyl-3-(isoxazol-5-yl)-1,5,6,7-tetrahydro-4H-indazol-4-one;
1-(3-chloropyridazin-6-yl)-7,7-dimethyl-3-phenyl-1,5,6,7-tetrahydro-4H-indazol-4-one;
1-(3-chloropyridazin-6-yl)-7,7-dimethyl-3-(thien-2-yl)-1,5,6,7-tetrahydro-4H-indazol-4-one;

3-benzyl-1-(3-chloropyridazin-6-yl)-7,7-dimethyl-1,5,6,7-tetrahydro-4H-indazol-4-one;

1-(3-chloropyridazin-6-yl)-7,7-dimethyl-3-(2-fluorophenyl)-1,5,6,7-tetrahydro-4H-indazol-4-one;

1-(3-chloropyridazin-6-yl)-7,7-dimethyl-3-(2-thienylmethyl)-1,5,6,7-tetrahydro-4H-indazol-4-one;

1-(3-chloropyridazin-6-yl)-3-(2-cyclopentylethyl)-7,7-dimethyl-1,5,6,7-tetrahydro-4H-indazol-4-one;

1-(3-chloropyridazin-6-yl)-7,7-dimethyl-3-(3-methoxyphenyl)-1,5,6,7-tetrahydro-4H-indazol-4-one;

1-(3-chloropyridazin-6-yl)-7,7-dimethyl-3-phenoxymethyl-1,5,6,7-tetrahydro-4H-indazol-4-one;

1-(3-chloropyridazin-6-yl)-7,7-dimethyl-3-(pyrid-4-yl)-1,5,6,7-tetrahydro-4H-indazol-4-one;

1-(3-chloropyridazin-6-yl)-7,7-dimethyl-3-(trans-2-phenylcycloprop-1-yl)-1,5,6,7-tetrahydro-4H-indazol-4-one;

1-(3-chloropyridazin-6-yl)-7,7-dimethyl-3-(4-dimethylaminophenyl)-1,5,6,7-tetrahydro-4H-indazol-4one;

1-(3-chloropyridazin-6-yl)-7,7-dimethyl-3-(quinoxal-2-yl)-1,5,6,7-tetrahydro-4H-indazol-4-one;

1-(3-chloropyridazin-6-yl)-7,7-dimethyl-3-(2,6-dimethoxyphenyl)-1,5,6,7-tetrahydro-4H-indazol-4-one;

1-(3-chloropyridazin-6-yl)-3-cyclopropyl1-5,5-dimethyl-1,5,6,7-tetrahydro-4H-indazol-4-one;

1-(3-chloropyridazin-6-yl)-5,5-dimethyl-3-(2-furyl)-1,5,6,7-tetrahydro-4H-indazol-4-one;

1-(3-chloropyridazin-6-yl)-5,5-dimethyl-3-(isoxazol-5-yl)-1,5,6,7-tetrahydro-4H-indazol-4-one;

1-(3-chloropyridazin-6-yl)-5,5-dimethyl-3-phenyl-1,5,6,7-tetrahydro-4H-indazol-4-one;

1-(3-chloropyridazin-6-yl)-5,5-dimethyl-3-(thien-2-yl)-1,5,6,7-tetrahydro-4H-indazol-4-one;

3-benzyl-1-(3-chloropyridazin-6-yl)-5,5-dimethyl-1,5,6,7-tetrahydro-4H-indazol-4-one;

1-(3-chloropyridazin-6-yl)-5,5-dimethyl-3-(2-fluorophenyl)-1,5,6,7-tetrahydro-4H-indazol-4-one;

1-(3-chloropyridazin-6-yl)-5,5-dimethyl-3-(2-thienylmethyl)-1,5,6,7-tetrahydro-4H-indazol-4-one;

1-(3-chloropyridazin-6-yl)-3-(2-cyclopentylethyl)-5,5-dimethyl-1,5,6,7-tetrahydro-4H-indazol-4-one;

1-(3-chloropyridazin-6-yl)-5,5-dimethyl-3-(3-methoxyphenyl)-1,5,6,7-tetrahydro-4H-indazol-4-one;

1-(3-chloropyridazin-6-yl)-5,5-dimethyl-3-phenoxymethyl-1,5,6,7-tetrahydro-4H-indazol-4-one;

1-(3-chloropyridazin-6-yl)-5,5-dimethyl-3-(pyrid-4-yl)-1,5,6,7-tetrahydro-4H-indazol-4-one;

1-(3-chloropyridazin-6-yl)-5,5-dimethyl-3-(trans-2-phenyl-cycloprop-1-yl)-1,5,6,7-tetrahydro-4H-indazol-4-one;

1-(3-chloropyridazin-6yl)-5,5-dimethyl-3-(4-dimethylaminophenyl)-1,5,6,7-tetrahydro-4H-indazol-4-one;

1-(3-chloropyridazin-6-yl)-5,5-dimethyl-3-(quinoxal-2-yl)-1,5,6,7-tetrahydro-4H-indazol-4-one;

1-(3-chloropyridazin-6-yl)-5,5-dimethyl-3-(2,6-dimethoxyphenyl)-1,5,6,7-tetrahydro-4H-indazol-4-one;

1-(benzothiazol-2-yl)-7-cyano-3-cyclopropyl1-6,6-dimethyl-1,5,6,7-tetrahydro-4H-indazol-4-one;

1-(benzothiazol-2-yl)-7-cyano-6,6-dimethyl-3-(2-furyl)-1,5,6,7-tetrahydro-4H-indazol-4-one;

1-(benzothiazol-2-yl)-7-cyano-6,6-dimethyl-3-(isoxazol-5-yl)-1,5,6,7-tetrahydro-4H-indazol-4-one;

1-(benzothiazol-2-yl)-7-cyano-6,6-dimethyl-3-phenyl-1,5,6,7-tetrahydro-4H-indazol-4-one;

1-(benzothiazol-2-yl)-7-cyano-6,6-dimethyl-3-(thien-2-yl)-1,5,6,7-tetrahydro-4H-indazol-4-one;

1-(benzothiazol-2-yl)-3-benzyl-7-cyano-6,6-dimethyl-1,5,6,7-tetrahydro-4H-indazol-4-one;

1-(benzothiazol-2-yl)-7-cyano-6,6-dimethyl-3-(2-fluorophenyl)-1,5,6,7-tetrahydro-4H-indazol-4-one;

1-(benzothiazol-2-yl)-7-cyano-6,6-dimethyl-3-(2-thienylmethyl)-1,5,6,7-tetrahydro-4H-indazol-4-one;

1-(benzothiazol-2yl)-7-cyano-3-(2-cyclopentylethyl)-6,6-dimethyl-1,5,6,7-tetrahydro-4H-indazol-4-one;

1-(benzothiazol-2-yl)-7-cyano-6,6-dimethyl-3-(3-methoxyphenyl)-1,5,6,7-tetrahydro-4H-indazol-4-one;

1-(benzothiazol-2-yl)-7-cyano-6,6-dimethyl-3-phenoxymethyl-1,5,6,7-tetrahydro-4H-indazol-4-one;

1-(benzothiazol-2-yl)-7-cyano-6,6-dimethyl-3-(pyrid-4-yl)-1,5,6,7-tetrahydro-4H-indazol-4-one;

1-(benzothiazol-2-yl)-7-cyano-6,6-dimethyl-3-(trans-2-phenyl-cycloprop-1-yl)-1,5,6,7-tetrahydro-4H-indazol-4-one;

1-(benzothiazol-2-yl)-7-cyano-6,6-dimethyl-3-(4-dimethylaminophenyl)-1,5,6,7-tetrahydro-4H-indazol-4-one;

1-(benzothiazol-2-yl)-7-cyano-6,6-dimethyl-3-(quinoxal-2-yl)-1,5,6,7-tetrahydro-4H-indazol-4-one;

1-(benzothiazol-2-yl)-7-cyano-6,6-dimethyl-3-(2,6-dimethoxyphenyl)-1,5,6,7-tetrahydro-4H-indazol-4-one;

1-(benzothiazol-2-yl)-5-cyano-3-cyclopropyl1-6,6-dimethyl-1,5,6,7-tetrahydro-4H-indazol-4-one;

1-(benzothiazol-2-yl)-5-cyano-6,6-dimethyl-3-(2-furyl)-1,5,6,7-tetrahydro-4H-indazol-4-one;

1-(benzothiazol-2-yl)-5-cyano-6,6-dimethyl-3-(isoxazol-5-yl)-1,5,6,7-tetrahydro-4H-indazol-4-one;

1-(benzothiazol-2-yl)-5-cyano-6,6-dimethyl-3-phenyl-1,5,6,7-tetrahydro-4H-indazol-4-one;

1-(benzothiazol-2-yl)-5-cyano-6,6-dimethyl-3-(thien-2-yl)-1,5,6,7-tetrahydro-4H-indazol-4-one;

1-(benzothiazol-2-yl)-3-benzyl-5-cyano-6,6-dimethyl-1,5,6,7-tetrahydro-4H-indazol-4-one;

1-(benzothiazol-2-yl)-5-cyano-6,6-dimethyl-3-(2-fluorophenyl)-1,5,6,7-tetrahydro-4H-indazol-4-one;

1-(benzothiazol-2-yl)-5-cyano-6,6-dimethyl-3-(2-thienylmethyl)-1,5,6,7-tetrahydro-4H-indazol-4-one;

1-(benzothiazol-2yl)-5-cyano-3-(2-cyclopentylethyl)-6,6-dimethyl-1,5,6,7-tetrahydro-4H-indazol-4-one;

1-(benzothiazol-2-yl)-5-cyano-6,6-dimethyl-3-(3-methoxyphenyl)-1,5,6,7-tetrahydro-4H-indazol-4-one;

1-(benzothiazol-2-yl)-5-cyano-6,6-dimethyl-3-phenoxymethyl-1,5,6,7-tetrahydro-4H-indazol-4-one;

1-(benzothiazol-2-yl)-5-cyano-6,6-dimethyl-3-(pyrid-4-yl)-1,5,6,7-tetrahydro-4H-indazol-4-one;

1-(benzothiazol-2-yl)-5-cyano-6,6-dimethyl-3-(trans-2-phenyl-cycloprop-1-yl)-1,5,6,7-tetrahydro-4H-indazol-4-one;

1-(benzothiazol-2-yl)-5-cyano-6,6-dimethyl-3-(4-dimethylaminophenyl)-1,5,6,7-tetrahydro-4H-indazol-4-one;

1-(benzothiazol-2-yl)-5-cyano-6,6-dimethyl-3-(quinoxal-2-yl)-1,5,6,7-tetrahydro-4H-indazol-4-one;

1-(benzothiazol-2-yl)-5-cyano-6,6-dimethyl-3-(2,6-dimethoxyphenyl)-1,5,6,7-tetrahydro-4H-indazol-4-one;

7-cyano-3-cyclopropyl1-6,6-dimethyl-1-(4-isopropylphenyl)-1,5,6,7-tetrahydro-4H-indazol-4-one;

7-cyano-6,6-dimethyl-3-(2-furyl)-1-(4-isopropylphenyl)-1,5,6,7-tetrahydro-4H-indazol-4-one;

7-cyano-6,6-dimethyl-1-(4-isopropylphenyl)-3-(isoxazol-5-yl)-1,5,6,7-tetrahydro-4H-indazol-4-one;

7-cyano-6,6-dimethyl-1-(4-isopropylphenyl)-3-phenyl-1,5,6,7-tetrahydro-4H-indazol-4-one;

7-cyano-6,6-dimethyl-1-(4-isopropylphenyl)-3-(thien-2-yl)-1,5,6,7-tetrahydro-4H-indazol-4-one;

3-benzyl-7-cyano-6,6-dimethyl-1-(4-isopropylphenyl)-1,5,6,7-tetrahydro-4H-indazol-4-one;

7-cyano-6,6-dimethyl-3-(2-fluorophenyl)-1-(4-isopropylphenyl)-1,5,6,7-tetrahydro-4H-indazol-4-one;

7-cyano-6,6-dimethyl-1-(4-isopropylphenyl)-3-(2-thienylmethyl)-1,5,6,7-tetrahydro-4H-indazol-4-one;

7-cyano-3-(2-cyclopentylethyl)-6,6-dimethyl-1-(4-isopropylphenyl)-1,5,6,7-tetrahydro-4H-indazol-4one;

7-cyano-6,6-dimethyl-1-(4-isopropylphenyl)-3-(3-methoxyphenyl)-1,5,6,7-tetrahydro-4H-indazol-4-one;

7-cyano-6,6-dimethyl-1-(4-isopropylphenyl)-3-phenoxymethyl-1,5,6,7-tetrahydro-4H-indazol-4-one;

7-cyano-6,6-dimethyl-1-(4-isopropylphenyl)-3-(pyrid-4-yl)-1,5,6,7-tetrahydro-4H-indazol-4-one;

7-cyano-6,6-dimethyl-1-(4-isopropylphenyl)-3-(trans-2-phenyl-cycloprop-1-yl)-1,5,6,7-tetrahydro-4H-indazol-4-one;

7-cyano-6,6-dimethyl-3-(4-dimethylaminophenyl)-1-(4-isopropylphenyl)-1,5,6,7-tetrahydro-4H-indazol-4-one;

7-cyano-6,6-dimethyl-1-(4-isopropylphenyl)-3-(quinoxal-2-yl)-1,5,6,7-tetrahydro-4H-indazol-4-one;

7-cyano-6,6-dimethyl-3-(2, 6-dimethoxyphenyl)-1-(4-isopropylphenyl)-1,5,6,7-tetrahydro-4H-indazol-4-one;

5-cyano-3-cyclopropyl1-6,6-dimethyl-1-(4-isopropylphenyl)-1,5,6,7-tetrahydro-4H-indazol-4-one;

5-cyano-6,6-dimethyl-3-(2-furyl)-1-(4-isopropylphenyl)-1,5,6,7-tetrahydro-4H-indazol-4-one;

5-cyano-6,6-dimethyl-1-(4-isopropylphenyl)-3-(isoxazol-5-yl)-1,5,6,7-tetrahydro-4H-indazol-4-one;

5-cyano-6,6-dimethyl-1-(4-isopropylphenyl)-3-phenyl-1,5,6,7-tetrahydro-4H-indazol-4-one;

5-cyano-6,6-dimethyl-1-(4-isopropylphenyl)-3-(thien-2-yl)-1,5,6,7-tetrahydro-4H-indazol-4-one;

3-benzyl-5-cyano-6,6-dimethyl-1-(4-isopropylphenyl)-1,5,6,7-tetrahydro-4H-indazol-4-one;

5-cyano-6,6-dimethyl-3-(2-fluorophenyl)-1-(4-isopropylphenyl)-1,5,6,7-tetrahydro-4H-indazol-4-one;

5-cyano-6,6-dimethyl-1-(4-isopropylphenyl)-3-(2-thienylmethyl)-1,5,6,7-tetrahydro-4H-indazol-4-one;

5-cyano-3-(2-cyclopentylethyl)-6,6-dimethyl-1-(4-isopropylphenyl)-1,5,6,7-tetrahydro-4H-indazol-4one;

5-cyano-6,6-dimethyl-1-(4-isopropylphenyl)-3-(3-methoxyphenyl)-1,5,6,7-tetrahydro-4H-indazol-4-one;

5-cyano-6,6-dimethyl-1-(4-isopropylphenyl)-3-phenoxymethyl-1,5,6,7-tetrahydro-4H-indazol-4-one;

5-cyano-6,6-dimethyl-1-(4-isopropylphenyl)-3-(pyrid-4-yl)-1,5,6,7-tetrahydro-4H-indazol-4-one;

5-cyano-6,6-dimethyl-1-(4-isopropylphenyl)-3-(trans-2-phenyl-cycloprop-1-yl)-1,5,6,7-tetrahydro-4H-indazol-4-one;

5-cyano-6,6-dimethyl-3-(4-dimethylaminophenyl)-1-(4-isopropylphenyl)-1,5,6,7-tetrahydro-4H-indazol-4-one;

5-cyano-6,6-dimethyl-1-(4-isopropylphenyl)-3-(quinoxal-2-yl)-1,5,6,7-tetrahydro-4H-indazol-4-one;

5-cyano-6,6-dimethyl-3-(2,6-dimethoxyphenyl)-1-(4-isopropylphenyl)-1,5,6,7-tetrahydro-4H-indazol-4-one;

3-cyclopropyl1-1-(4-iodophenyl)-8-methyl-1,5,5a,6,7,8,9,9a-octahydro-4H-pyrazolo[4,3-h]isoquinolin-4-one;

3-(2-furyl)-1-(4-iodophenyl)-8-methyl-1,5,5a,6,7,8,9,9a-octahydro-4H-pyrazolo[4,3-h]isoquinolin-4-one;

1-(4-iodophenyl)-3-(isoxazol-5-yl)-8-methyl-1,5,5a,6,7,8,9,9a-octahydro-4H-pyrazolo[4,3-h]isoquinolin-4-one;

1-(4-iodophenyl)-8-methyl-3-phenyl-1,5,5a,6,7,8,9,9a-octahydro-4H-pyrazolo[4,3-h]isoquinolin-4-one;

1-(4-iodophenyl)-8-methyl-3-(thien-2-yl)-1,5,5a,6,7,8,9,9a-octahydro-4H-pyrazolo[4,3-h]isoquinolin-4-one;

3-benzyl-1-(4-iodophenyl)-8-methyl-1,5,5a,6,7,8,9,9a-octahydro-4H-pyrazolo[4,3-h]isoquinolin-4-one;

3-(2-fluorophenyl)-1-(4-iodophenyl)-8-methyl-1,5,5a,6,7,8,9,9a-octahydro-4H-pyrazolo[4,3-h]isoquinolin-4-one;

1-(4-iodophenyl)-8-methyl-3-(2-thienylmethyl)-1,5,5a,6,7,8,9,9a-octahydro-4H-pyrazolo[4,3-h]isoquinolin-4-one;

3-(2-cyclopentylethyl)-1-(4-iodophenyl)-8-methyl-1,5,5a,6,7,8,9,9a-octahydro-4H-pyrazolo[4,3-h]isoquinolin-4-one;

1-(4-iodophenyl)-3-(3-methoxyphenyl)-8-methyl-1,5,5a,6,7,8,9,9a-octahydro-4H-pyrazolo[4,3-h]isoquinolin-4-one;

1-(4-iodophenyl)-8-methyl-3-phenoxymethyl-1,5,5a,6,7,8,9,9a-octahydro-4H-pyrazolo[4,3-h]isoquinolin-4-one;

1-(4-iodophenyl)-8-methyl-3-(pyrid-4-yl)-1,5,5a,6,7,8,9,9a-octahydro-4H-pyrazolo[4,3-h]isoquinolin-4-one;

1-(4-iodophenyl)-8-methyl-3-(trans-2-phenyl-cycloprop-1-yl)-1,5,5a,6,7,8,9,9a-octahydro-4H-pyrazolo[4,3-h]isoquinolin-4-one;

3-(4-dimethylaminophenyl)-1-(4-iodophenyl)-8-methyl-1,5,5a,6,7,8,9,9a-octahydro-4H-pyrazolo[4,3-h]isoquinolin-4-one;

1-(4-iodophenyl)-8-methyl-3-(quinoxal-2-yl)-1,5,5a,6,7,8,9,9a-octahydro-4H-pyrazolo[4,3-h]isoquinolin-4-one;

3-(2,6-dimethoxyphenyl)-1-(4-iodophenyl)-8-methyl-1,5,5a,6,7,8,9,9a-octahydro-4H-pyrazolo[4,3-h]isoquinolin-4-one;

3-cyclopropyl-1-(4-iodophenyl)-6-methyl-1,4a,5,6,7,8,8a,9-octahydro-4H-pyrazolo[3,4-g]isoquinolin-4-one;

3-(2-furyl)-1-(4-iodophenyl)-6-methyl-1,4a,5,6,7,8,8a,9-octahydro-4H-pyrazolo[3,4-g]isoquinolin-4one;

1-(4-iodophenyl)-3-(isoxazol-5-yl)-6-methyl-1,4a,5,6,7,8,8a,9-octahydro-4H-pyrazolo[3,4-g]isoquinolin-4-one;

1-(4-iodophenyl)-6-methyl-3-phenyl-1,4a,5,6,7,8,8a,9-octahydro-4H-pyrazolo[3,4-g]isoquinolin-4-one;

1-(4-iodophenyl)-6-methyl-3-(thien-2-yl)-1,4a,5,6,7,8,8a,9-octahydro-4H-pyrazolo[3,4-g]isoquinolin-4-one;

3-benzyl-1-(4-iodophenyl)-6-methyl-1,4a,5,6,7,8,8a,9-octahydro-4H-pyrazolo[3,4-g]isoquinolin-4-one;

3-(2-fluorophenyl)-1-(4-iodophenyl)-6-methyl-1,4a,5,6,7,8,8a,9-octahydro-4H-pyrazolo[3,4-g]isoquinolin-4-one;

1-(4-iodophenyl)-6-methyl-3-(2-thienylmethyl)-1,4a,5,6,7,8,8a,9-octahydro-4H-pyrazolo[3,4-g]isoquinolin-4-one;

3-(2-cyclopentylethyl)-1-(4-iodophenyl)-6-methyl-1,4a,5,6,7,8,8a,9-octahydro-4H-pyrazolo[3,4-g]isoquinolin-4-one;

1-(4-iodophenyl)-3-(3-methoxyphenyl)-6-methyl-1,4a,5,6,7,8,8a,9-octahydro-4H-pyrazolo[3,4-g]isoquinolin-4-one;

1-(4-iodophenyl)-6-methyl-3-phenoxymethyl-1,4a,5,6,7,8,8a,9-octahydro-4H-pyrazolo[3,4-g]isoquinolin-4-one;

1-(4-iodophenyl)-6-methyl-3-(pyrid-4-yl)-1,4a,5,6,7,8,8a,9-octahydro-4H-pyrazolo[3,4-g]isoquinolin-4-one;

1-(4-iodophenyl)-6-methyl-3-(trans-2-phenyl-cycloprop-1-yl)-1,4a,5,6,7,8,8a,9-octahydro-4H-pyrazolo[3,4-g]isoquinolin-4-one;

3-(4-dimethylaminophenyl)-1-(4-iodophenyl)-6-methyl-1,4a,5,6,7,8,8a,9-octahydro-4H-pyrazolo[3,4-g]isoquinolin-4-one;

1-(4-iodophenyl)-6-methyl-3-(quinoxal-2-yl)-1,4a,5,6,7,8,8a,9-octahydro-4H-pyrazolo[3,4-g]isoquinolin-4-one;

3-(2,6-dimethoxyphenyl)-1-(4-iodophenyl)-6-methyl-1,4a,5,6,7,8,8a,9-octahydro-4H-pyrazolo[3,4-g]isoquinolin-4-one;

1-(7-chloro-quinolin-4-yl)-3-cyclopropyl-indeno[1,2-c]pyrazol-4(1H)-one;

1-(7-chloro-quinolin-4-yl)-3-(2-furyl)-indeno[1,2-c]pyrazol-4(1H)-one;

1-(7-chloro-quinolin-4-yl)-3-(isoxazol-5-yl)-indeno[1,2-c]pyrazol-4(1H)-one;

1-(7-chloro-quinolin-4-yl)-3-phenyl-indeno[1,2-c]pyrazol-4(1H)-one;

1-(7-chloro-quinolin-4-yl)-3-(thien-2-yl)-indeno[1,2-c]pyrazol-4(1H)-one;

3-benzyl-1-(7-chloro-quinolin-4-yl)-indeno[1,2-c]pyrazol-4(1H)-one;

1-(7-chloro-quinolin-4-yl)-3-(2-fluorophenyl)-indeno[1,2-c]pyrazol-4(1H)-one;

1-(7-chloro-quinolin-4-yl)-3-(2-thienylmethyl)-indeno[1,2-c]pyrazol-4(1H)-one;

1-(7-chloro-quinolin-4-yl)-3-(2-cyclopentylethyl)-indeno[1,2-c]pyrazol-4(1H)-one;

1-(7-chloro-quinolin-4-yl)-3-(3-methoxyphenyl)-indeno[1,2-c]pyrazol-4(1H)-one;

1-(7-chloro-quinolin-4-yl)-3-phenoxymethyl-indeno[1,2-c]pyrazol-4(1H)-one 1-(7-chloro-quinolin-4-yl)-3-(pyrid-4-yl)-indeno[1,2-c]pyrazol-4(1H)-one;

1-(7-chloro-quinolin-4-yl)-3-(trans-2-phenyl-cycloprop-1-yl)-indeno[1,2-c]pyrazol-4(1H)-one;

1-(7-chloro-quinolin-4-yl)-3-(4-dimethylaminophenyl)-indeno[1,2-c]pyrazol-4(1H)-one;

1-(7-chloro-quinolin-4-yl)-3-(quinoxal-2-yl)-indeno[1,2-c]pyrazol-4(1H)-one and 1-(7-chloro-quinolin-4-yl)-3-(2,6-dimethoxyphenyl)-indeno[1,2-c]pyrazol-4(1H)-one.

EXAMPLE 4

Preparation of 7-Bromo-1-(2-pyridyl)-3,6,6-trimethyl-4-oxo-4,5,6,7-tetrahydroindazole.

A mixture of 1-(2-pyridyl)-3,6,6-trimethyl-4-oxo-4,5,6,7-tetrahydroindazole (0.25 g, 0.98 mmol), prepared as described in example 3, and N-bromosuccinimide (0.180 g, 0.98 mmol) in chloroform (6 ml) was stirred at 60° C. for about 4 hours and then washed with water. The organic phase was dried over sodium sulfate and evaporated to dryness. The residue was chromatographed on silica gel (cyclohexane:ethyl acetate=90:10). The title compound was obtained as a colourless solid (0.28 g, 85%): m.p 160–161° C.

$^1$H-NMR (DMSO-d$^6$) δ ppm: 8.59–7.42 (m, 4H, 2-Py); 6.39 (s, 1H, CH); 2.65 (d, 1H, CH—H); 2.41 (s, 3H, CH$_3$); 2.22 (d, 1H, CH—H); 1.3 (s, 3H, CH$_3$CCH$_3$); 1.09 (s, 3H, CH$_3$CCH$_3$)

EXAMPLE 5

Preparation of 7-Fluoro-1-(2-pyridyl)-3,6,6-trimethyl-4-oxo-4,5,6,7-tetrahydroindazole.

A mixture of 7-bromo-1-(2-pyridyl)-3,6,6-trimethyl-4-oxo-4,5,6,7-tetrahydroindazole (0.6 g, 1.8 mmol), prepared as described in example 4, and silver fluoride (1 g, 1 mmol) in acetonitrile (4.6 ml) and water (12 ml) was stirred at 80° C. for about 8 hours and then poured through a bed of silica gel. Dichloromethane (100 ml) was allowed to percolate slowly through it. After evaporation of the solvent, the residue was chromatographed on silica gel (cyclohexane:ethyl acetate=90:10). The title compound was obtained as a colourless solid (0.1 g, 22%): m.p. 115–117° C.

$^1$H-NMR (DMSO-d$^6$) δ ppm: 8.58–7.45 (m, 4H, 2-Py); 6.24 (d, 1H, CHF); 2.7 (d, 1H, CH—H); 2.42 (s, 3H, CH$_3$); 2.22 (d, 1H, CH—H); 1.2 (s, 3H, CH$_3$CCH$_3$); 0.97 (s, 3H, CH$_3$CCH$_3$).

EXAMPLE 6

Preparation of 7-Methoxy-1-(2-pyridyl)-3,6,6-trimethyl-4-oxo-4,5,6,7-tetrahydroindazole.

A solution of 0.1N silver nitrate in methanol (12 ml, 1.2 mmol) was added to a solution of 7-bromo-1-(2-pyridyl)-3,6,6-trimethyl-4-oxo-4,5,6,7-tetrahydroindazole (0.2 g, 0.6 mmol), prepared as described in example 4, in acetone (12 ml). After stirring for about 48 hours, 6 ml of a 0.1N silver nitrate solution in methanol were added. The reaction mixture was stirred for further 72 hours and then filtered. The solvent was evaporated and the residue was chromatographed on silica gel (cyclohexane:ethyl acetate=90:10) to yield the title compound as a colourless solid (0.044 g, 25%): m.p. 86–89° C.

$^1$H-NMR (DMSO-d$^6$) δ ppm: 8.58–7.43 (m, 4H, 2-Py); 5.21 (s, 1H, CHOMe); 3.22 (s, 3H, OCH$_3$); 2.63 (d, 1H, CH—H); 2.4 (s, 3H, CH$_3$); 2.15 (d, 1H, CH—H); 1.18 (s, 3H, CH$_3$CCH$_3$); 0.92 (s, 3H, CH$_3$CCH$_3$).

By working in an analogous way and by using an aqueous solution 0.1N of silver nitrate, the following compound can be obtained:

7-hydroxy-1-(2-pyridyl)-3,6,6-trimethyl-4-oxo-4,5,6,7-tetrahydroindazole m.p. 126–128° C.; $^1$H-NMR (DMSO-d$^6$) δ ppm: 8.57–7.42 (m, 4H, 2-Py); 5.6 (d, 1H, OH); 5.1 (d, 1H, CHOH); 2.7 (d, 1H, CH—H); 2.4 (s, 3H, CH$_3$); 2.27 (d, 1H, CH—H); 1.05 (s, 3H, CH$_3$CCH$_3$); 0.91 (s, 3H, CH$_3$CCH$_3$).

EXAMPLE 7
Preparation of 7-(N,N-Dimethylamino)-1-(2-pyridyl)-3,6,6-trimethyl-4-oxo-4,5,6,7-tetrahydroindazole Hydrochloride.

A mixture of 7-bromo-1-(2-pyridyl)-3,6,6-trimethyl-4-oxo-4,5,6,7-tetrahydroindazole (0.25 g, 0.75 mmol), prepared as described in example 4, and 5.6 M dimethylamine in ethanol (15 ml) in 3.5 ml of tetrahydrofurane was maintained at room temperature for about 12 days and then evaporated. The residue was diluted with dichloromethane, washed with water and brine, dried over sodium sulfate, evaporated and chromatographed on silica gel (cyclohexane:ethyl acetate=90:10) to give a colourless oil (0.17 g, 0.57 mmol) which was dissolved in ether and treated with 1M HCl (0.61 ml, 0.63 mmol) to yield the title compound as a light yellow solid (0.12 g, 48%): m.p. 207–212° C.

EXAMPLE 8
Preparation of 7-Phenylthio-1-(2-pyridyl)-3,6,6-trimethyl-4-oxo-4,5,6,7-tetrahydroindazole.

The solution of 7-bromo-1-(2-pyridyl)-3,6,6-trimethyl-4-oxo-4,5,6,7-tetrahydroindazole (0.6 g, 1.8 mmol), prepared as described in example 4, and sodium thiophenate (0.3 g, 2.24 mmol) in dry N,N-dimethylformamide (10 ml) was stirred at room temperature for about 5 hours and then poured into brine and extracted with dichloromethane. The combined organic layers were washed with brine, dried over sodium sulfate end evaporated. The residue was chromatographed on silica gel (cyclohexane:ethyl acetate=90:10) to give 0.3 g (45% yield) of the title compound as a colourless solid which crystallized on standing.

$^1$H-NMR (DMSO-d$^6$) δ ppm: 8.33–7.4 (m, 4H, 2-Py); 7.12 (m, 5H, Ph); 5.8 (s, 1H, CHSPh); 2.8 (d, 1H, CH—H); 2.4 (s, 3H, CH$_3$); 2.1 (d, 1H, CH—H); 1.2 (s, 3H, CH$_3$CCH$_3$); 1.1 (s, 3H, CH$_3$CCH$_3$).

EXAMPLE 9
Preparation of 7-Phenylsulfonyl-1-(2-pyridyl)-3,6,6-trimethyl-4-oxo-4,5,6,7-tetrahydroindazole.

A solution of Oxone (2 g, 3.2 mmol) in 6 ml of water was added dropwise to a solution of 7-phenylthio-1-(2-pyridyl)-3,6,6-trimethyl-4-oxo-4,5,6,7-tetrahydroindazole (0.24 g, 0.66 mmol), prepared as described in example 8, in methanol (6 ml), maintained under stirring at 0° C. After the addition was complete, the reaction mixture was allowed to warm to room temperature and stirring was continued for about 1.5 hours. Water was then added and the mixture was extracted with dichloromethane. The combined organic layers were washed with brine, dried over sodium sulfate end evaporated. The residue was chromatographed on silica gel (cyclohexane:ethyl acetate=7:3), to yield the title compound as a colourless solid (0.175 g, 61%): m.p. 165–166° C.

$^1$H-NMR (DMSO-d$^6$) δ ppm: 8.49–7.3 (m, 9H, 2-Py and Ph); 6.22 (s, 1H, CHSOPh); 3.3 (d, 1H, CH—H); 2.49 (s, 3H, CH$_3$); 2.25 (d, 1H, CH—H); 1.42 (s, 3H, CH$_3$CCH$_3$); 1.1 (s, 3H, CH$_3$CCH$_3$).

EXAMPLE 10
Preparation of 4-(N-Hydroxy-immino)-1-(2-pyridyl)-3,6,6-trimethyl-4,5,6,7-tetrahydroindazole.

A mixture of 1-(2-pyridyl)-3,6,6-trimethyl-4-oxo-4,5,6,7-tetrahydroindazole (0.27 g, 1.06 mmol), prepared as described in example 3, hydroxylamine hydrochloride (0.37 g, 5.29 mmol) and sodium acetate (0.43 g, 5.29 mmol) in ethanol (20 ml) was heated under reflux for about 7 hours, poured onto ice/water and then filtered. The title compound was obtained after drying in vacuo as a colourless solid (0.17 g, 60%): m.p. 198–199° C.

$^1$H-NMR (DMSO-d$^6$) δ ppm: 10.7 (s, 1H, NOH); 8.41–7.3 (m, 4H, 2-Py); 3.05 (s, 2H, CH$_2$); 2.48 (s, 3H, CH$_3$); 2.38 (s, 2H, CH$_2$); 1.0 (s, 6H, gem CH$_3$).

By working in an analogous way and by starting from 7-bromo-1-(2-pyridyl)-3,6,6-trimethyl-4-oxo-4,5,6,7-tetrahydroindazole, the following compound can be obtained:

7-ethoxy-4-(N-hydroxy-imino)-1-(2-pyridyl)-3,6,6-trimethyl-4,5,6,7-tetrahydroindazole m.p. 167–168° C.; $^1$H-NMR (DMSO-d$^6$) δ ppm: 10.88 (s, 1H, NOH); 8.48–7.38 (m, 4H, 2-Py); 5.12 (s, 1H, CHOEt); 3.4 (m, 2H, OCH$_2$CH$_3$); 2.72 (d, 1H, CH—H); 2.4 (s, 3H, CH$_3$); 2.21 (d, 1H, CH—H); 1.19 (s, 3H, CH$_3$CCH$_3$); 0.88 (m, 3H, OCH$_2$CH$_3$); 0.8 (s, 3H, CH$_3$CCH$_3$).

EXAMPLE 11
Preparation of 7-Bromo-4-(N-hydroxy-imino)-1-(2-pyridyl)-3,6,6-trimethyl-4,5,6,7-tetrahydroindazole.

A mixture of 7-bromo-1-(2-pyridyl)-3,6,6-trimethyl-4-oxo-4,5,6,7-tetrahydro-indazole (0.3 g, 0.9 mmol), prepared as described in example 4, hydroxylamine hydrochloride (0.37 g, 4.5 mmol), and sodium acetate (0.44 g, 5.4 mmol) in 1,4-dioxane (50 ml) was heated under reflux for about 4 hours. Additional hydroxylamine hydrochloride (0.123 g, 1.6 eq) and sodium acetate (0.146 g, 2 eq) were added and heating was continued for further 4 hours. The reaction mixture was poured onto ice/water and extracted with dichloromethane. The combined organic layers were washed with brine, dried over sodium sulfate and evaporated. The residue was chromatographed on silica gel (cyclohexane:ethyl acetate=90:10) to give the title compound as a colourless solid (0.14 g, 45%): m.p. 195–196° C.

$^1$H-NMR (DMSO-d$^6$) δ ppm: 11.2 (s, 1H, NOH); 8.5–7.35 (m, 4H, 2-Py); 6.38 (s, 1H, CH); 3.0 (d, 1H, CH—H); 2.4 (s, 3H, CH$_3$); 2.15 (d, 1H, CH—H); 1.25 (s, 3H, CH$_3$CCH$_3$); 1.1 (s, 3H, CH$_3$CCH$_3$).

EXAMPLE 12
Preparation of 4-Hydroxy-1-(2-pyridyl)-3,6,6-trimethyl-4,5,6,7-tetrahydroindazole.

0.09 g (2.36 mol) of sodium borohydride were added portionwise to the solution of 1-(2-pyridyl)-3,6,6-trimethyl-4-oxo-4,5,6,7-tetrahydroindazole (0.3 g, 1.18 mmol), prepared as described in example 3, in ethanol (15 ml) maintained under inert atmosphere and under magnetic stirring at room temperature. After about 20 hours, additional sodium borohydride (0.09 g) was added and the reaction mixture was heated at about 50° C. for about 8 hours. The solvent was evaporated and the residue was diluted with water and extracted with dichloromethane. The combined organic layers were dried over sodium sulfate and evaporated to give a foam which was treated with cyclohexane and filtered to yield the title compound as a colourless solid (0.2 g, 66%): m.p. 125–126° C.

$^1$H-NMR (DMSO-d$^6$) δ ppm: 8.4–7.2 (m, 9H, 2-Py); 4.78 (d, 1H, OH); 4.6 (m, 1H, CHOH); 2.9 (d, 1H, CH—H); 2.81 (d, 1H CH—H); 2.22 (s, 3H, CH$_3$); 1.75 (dd, 1H, 5-CH—H); 1.42 (dd, 1H, 5-CH—H); 1.07 (s, 3H, CH$_3$CCH$_3$); 1.1 (s, 3H, CH$_3$CCH$_3$).

EXAMPLE 13
Preparation of 4-Methoxy-1-(2-pyridyl)-3,6,6-trimethyl-4,5,6,7-tetrahydroindazole.

0.11 g (2.04 mmol) of 55% sodium hydride in oil were added to a solution of 4-hydroxy-1-(2-pyridyl)-3,6,6-trimethyl-4,5,6,7-tetrahydroindazole (0.35 g, 1.36 mmol), prepared as described in example 12, in dry tetrahydrofuran (5 ml) maintained under magnetic stirring and inhert atmosphere at 0° C. After 5 minutes, 0.13 ml (2.04 mmol) of methyl iodide were added, the reaction mixture was allowed to warm to room temperature and after 3.5 hours further 0.13 ml of methyl iodide were added. Stirring was continued for about 24 hours, additional sodium hydride (0.11 g) and methyl iodide (0.13 ml) were added and after 2.5 hours the solvent was evaporated. The residue was chromatographed on silica gel (cyclohexane:ethyl acetate=90:10), to yield the title compound as a colourless solid (0.3 g, 82%): m.p. 66–68° C.

$^1$H-NMR (DMSO-d$^6$) δ ppm: 8.4–7.23 (m, 4H, 2-Py); 4.35 (dd, 1H, CHOMe); 3.3 (s, 3H, OCH$_3$); 2.9 (2d, 2H, CH$_2$); 2.2 (s, 3H, CH$_3$); 1.8 (dd, 1H, 5-CH—$\underline{H}$); 1.58 (dd, 1H, 5-CH—$\underline{H}$); 1.2 (s, 3H, CH$_3$C$\underline{CH}_3$); 0.92 (s, 3H, CH$_3$C$\underline{CH}_3$).

EXAMPLE 14
Preparation of 1-(3-Aminophenyl)-3,6,6-trimethyl-4-oxo-4,5,6,7-tetrahydroindazole.

Stannous chloride dihydrate (0.94 g, 4.2 mmol) was added to a solution of 1-(3-nitrophenyl)-3,6,6-trimethyl-4-oxo-4,5,6,7-tetrahydroindazole (0.25 g, 0.84 mmol), prepared as described in example 3, in ethanol (5 ml). The reaction mixture was heated at 70° C. for about 1 hour, cooled to room temperature, poured onto ice, neutralized with 5% sodium bicarbonate and extracted with dichloromethane. The combined organic layers were washed with brine, dried over sodium sulfate and evaporated. The residue was chromatographed on silica gel (cyclohexane:ethyl acetate=60:40) to give the title compound as a colourless solid (0.125 g, 60%): m.p. 131–132° C.

$^1$H-NMR (DMSO-d$^6$) δ ppm: 7.1–6.6 (m, 3H, Ph); 5.4 (s, 2H, NH$_2$); 2.8 (s, 2H, CH$_2$); 2.35 (s, 3H, CH$_3$); 2.3 (s, 2H, CH$_2$); 1.0 (s, 6H, gem CH$_3$).

EXAMPLE 15
Preparation of 3,6,6-Trimethyl-4-oxo-4,5,6,7-tetrahydro-1H-indazole.

A mixture of 2-acetyl-5,5-dimethyl-cyclohexane-1,3-dione (2 g, 11.04 mmol), prepared as described in example 2, and hydrazine hydrate (1.66 ml, 33.13 mmol) in ethanol (25 ml) was stirred at room temperature for about 3 hours and then the solvent was evaporated. The residue was dissolved in dichloromethane, washed with water and brine, dried over sodium sulfate and evaporated. The title compound was obtained after chromatography on silica gel (dichloromethane:methanol=95:5) as a colourless solid (0.8 g, 45%): m.p. 103–104° C.

$^1$H-NMR (DMSO-d$^6$) δ ppm: 12.8 (broad, 1H, NH); 2.6 (s, 2H, CH$_2$); 2.25 (s, 3H, CH$_3$); 2.0 (s, 2H, CH$_2$); 1.0 (s, 6H, gem CH$_3$).

EXAMPLE 16
Preparation of 1-Aminocarbonyl-3,6,6-trimethyl-4-oxo-4,5,6,7-tetrahydroindazole.

A solution of trichloromethyl chloroformate (0.37 ml, 3.03 mmol) in 3 ml of dichloromethane was added dropwise to a solution of 3,6,6-trimethyl-4-oxo-4,5,6,7-tetrahydro-1H-indazole (0.4 g, 2.25 mmol), prepared as described in example 15, and triethylamine (0.42 ml, 3.03 mmol) maintained under magnetic stirring and inert atmosphere at about −15° C. The reaction mixture was allowed to warm to room temperature and stirring was continued for about 3.5 hours. A solution of 32% amonium hydroxide (10 ml) was then added while cooling at −15° C. The mixture was kept at room temperature for about 12 hours and the two layers were separated; dichloromethane was washed with water and brine, dried over sodium sulfate and evaporated. The residue was chromatographed on silica gel (cyclohexane:ethyl acetate=20:30), to yield the title compound as a colourless solid (0.170 g, 36%): m.p. 173–175° C.

$^1$H-NMR (DMSO-d$^6$) δ ppm: 7.82 (broad, 2H, CONH$_2$); 3.1 (s, 2H, CH$_2$); 2.38 (s, 3H, CH$_3$); 2.3 (s, 2H, CH$_2$); 1.0 (s, 6H, gem CH$_3$).

What is claimed is:

1. A compound which is a 4,5,6,7-tetrahydroindazole derivative of formula (I):

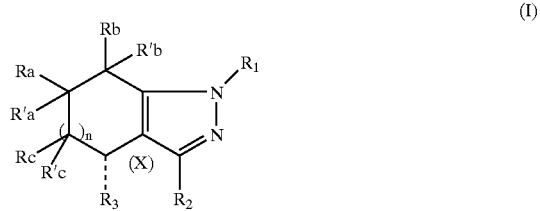

wherein:
the dotted line (x) represents a double bond;
n is 1;
R$_1$ is pyridyl;
R$_2$ is hydrogen or a group selected from straight or branched C$_1$–C$_6$ alkyl, C$_3$–C$_6$ cycloalkyl or cycloalkylalkyl with from 1 to 6 carbon atoms within the alkyl chain, aryl or arylalkyl with from 1 to 6 carbon atoms within the alkyl chain, each of which being optionally further substituted by one or more groups selected from halogens, cyano, straight or branched C$_1$–C$_6$ alkyl, straight or branched C$_1$–C$_6$ alkoxy, aryl, aryloxy, amino, alkylamino, dialkylamino with from 1 to 6 carbon atoms within the alkyl chain;
R$_3$ is an oxygen atom (═O), a sulphur atom (═S) or an imino group (═N—R$_4$) wherein R$_4$ is hydrogen, hydroxyl or a C$_1$–C$_6$ alkoxy group;
Ra and R'a are, each independently, hydrogen or straight or branched C$_1$–C$_6$ alkyl;
Rb and R'b are, each independently, hydrogen, halogen or a group selected from straight or branched C$_1$–C$_6$ alkyl, straight or branched C$_1$–C$_6$ alkoxy, straight or branched C$_1$–C$_6$ alkylthio, cyano, hydroxyl, amino, mono- or di-alkylamino with from 1 to 6 carbon atoms in the alkyl chains, arylthio, arylsulfinyl, arylsulfonyl, wherein each of the above aryl and alkyl moieties are optionally further substituted by one or more groups selected from halogen atoms, amino, nitro, hydroxy, C$_1$–C$_6$ alkyl or C$_1$–C$_6$ alkoxy groups;
Rc and R'c, are each independently hydrogen, straight or branched C$_1$–C$_6$ alkyl or cyano; or,
Ra and Rb together and/or Ra and Rc together form a N-alkyl-piperydinyl ring with 1 to 6 carbon atoms in the alkyl chain or a phenyl ring; or
a pharmaceutically acceptable salt thereof;
with the provisos that:
a) the compound is not 1-(2-pyridyl)-3,6,6-trimethyl-4-oxo-4,5,6,7-tetrahydroindazole and 7-bromo-1-(2- pyridyl)-3,6,6-trimethyl-4-oxo-4,5,6,7-tetrahydroindazole and b) when $R_3$ is O and $R_2$ is methyl, then Ra, R'a, and Rb, R'b are not all H.

2. A compound of formula (I) according to claim 1 wherein R'b, Rc and R'c are hydrogen atoms, $R_3$ is an oxygen atom or an imino group and $R_2$, Ra and R'a are, each independently, $C_1$–$C_3$ alkyl groups.

3. A compound of formula (I) according to claim 1, optionally in the form of a pharmaceutically acceptable salt, selected from:

7-fluroro-1-(2-pyridyl)-3,6,6-trimethyl-4-oxo-4,5,6,7-tetrahydroindazole;

7-methoxy-1-(2-pyridyl)-3,6,6-trimethyl-4-oxo-4,5,6,7-tetrahydroindazole;

7-hydroxy-1-(2-pyridyl)-3,6,6-trimethyl-4-oxo-4,5,6,7-tetrahydroindazole;

7-(N,N-dimethylamino)-1-(2-pyridyl)-3,6,6-trimethyl-4-oxo-4,5,6,7-tetrahydroindazole;

7-phenylthio-1-(2-pyridyl)-3,6,6-trimethyl-4-oxo-4,5,6,7-tetrahydroindazole;

7-phenylsulfonyl-1-(2-pyridyl)-3,6,6-trimethyl-4-oxo-4,5,6,7-tetrahydroindazole;

4-(N-hydroxy-imino)-1-(2-pyridyl)-3,6,6-trimethyl-4,5,6,7-tetrahydroindazole;

7-bromo-4-(N-hydroxy-imino)-1-(2-pyridyl)-3,6,6-trimethyl-4,5,6,7-tetrahydroindazole;

7-ethoxy-4-(N-hydroxy-imino)-3,6,6-trimethyl-4,5,6,7-tetrahydroindazole;

4-hydroxy-1-(2-pyridyl)-3,6,6-trimethyl-4,5,6,7-tetrahydroindazole;

4-methoxy-1-(2-pyridyl)-3,6,6-trimethyl-4,5,6,7-tetrahydroindazole;

4-phenylmethyl-3,6,6-trimethyl-4-oxo-4,5,6,7-tetrahydroindazole;

1-(3-nitrophenyl)-3,6,6-trimethyl-4-oxo-4,5,6,7-tetrahydroindazole;

1-(3-aminophenyl)-3,6,6-trimethyl-4-oxo-4,5,6,7-tetrahydroindazole; and 1-aminocarbonyl-3,6,6-trimethyl-4-oxo-4,5,6,7-tetrahydroindazole.

4. A process for preparing the compound of claim 1 comprising:

a) when (x) is a double bond and $R_3$ is oxygen, reacting a compound of formula (II) or a polymer supported analogue thereof (IIa):

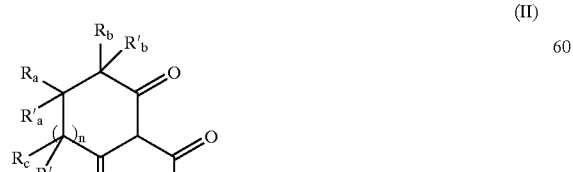

(II)

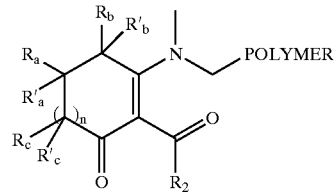

(IIa)

wherein n, $R_2$, Ra, R'a, Rb, R'b, Rc and R'c are as defined in claim 1, with a substituted hydrazine of formula $R_1$—NHNH$_2$ (III)

wherein $R_1$ is as defined in claim 1, thus obtaining the corresponding compound of formula (Ia):

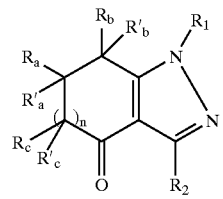

(Ia)

wherein n, $R_1$, $R_2$, Ra, R'a, Rb, R'b, Rc and R'c are as defined in claim 1, and, optionally, converting a compound of formula (Ia) into another compound of formula (I) or into a salt thereof by:

i) reacting the compound of formula (Ia) wherein n, $R_1$, $R_2$, Ra, R'a, R'b, Rc and R'c are as defined above and Rb is hydrogen with a suitable halogenating agent so as to obtain a compound of formula (Ib):

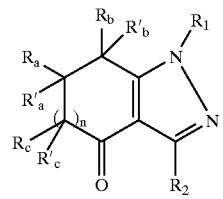

(Ib)

wherein Rb is a chlorine, bromine or iodine atom and n, $R_1$, $R_2$, Ra, R'a, R'b, Rc and R'c are as defined above;

ii) converting the compound of formula (Ib), presence of a nucleophylic agent, in the into a compound of formula (Ic)

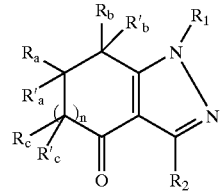

(Ic)

wherein Rb is fluorine, hydroxy, amino, mono- or di-alkylamino, alkylthio, arylthio or alkoxy and n, $R_1$, $R_2$, Ra, R'a, Rb, Rc and R'c are as defined above;

iii) oxidising the compound of formula (Ic) wherein Rb is alkylthio or arylthio into a compound of formula (Id):

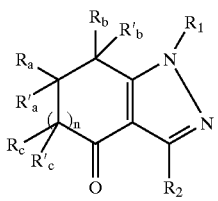

(Id)

wherein Rb is alkylsulfinyl, alkylsulfonyl, arylsulfinyl or arylsulfonyl and n, $R_1$, $R_2$, Ra, R'a, R'b, Rc and R'c are as defined above; or b) when $R_3$ is imino or amino, reacting a compound of formula (I) wherein (x) is a double bond and R, is oxygen with a suitable amine of formula $R_4$—$NH_2$ (IV)

wherein $R_4$ is as defined in claim 1, thus obtaining the corresponding compound of formula (Ie):

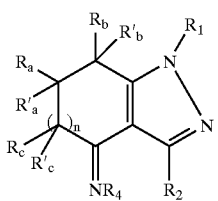

(Ie)

wherein n, $R_1$, $R_2$, $R_4$ Ra, R'a, Rb, R'b, Rc and R'c are as defined above; and, optionally, i) reducing the corresponding compound of formula (Ie) into the corresponding amine (If);

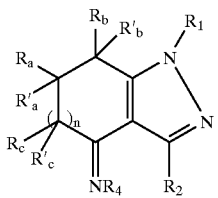

(If)

wherein n, $R_2$, $R_2$, $R_4$, Ra, R'a, Rb, R'b, Rc and R'c are as defined above; or, alternatively, ii) reacting a compound of formula (I) wherein (x) is a double bond and $R_3$ is oxygen with a suitable di-alkylamine, in the presence of a Lewis acid, so as to obtain the corresponding compound of formula (I) wherein (x) is a single bond and $R_3$ is a di-alkylamino group with from 1 to 6 carbon atoms in the alkyl chains; or c) when (x) is a double bond and $R_3$ is a sulphur atom, reacting a compound of formula (I) wherein (x) is a double bond and $R_3$ is oxygen with a thiating agent, thus obtaining a compound of formula (Ig):

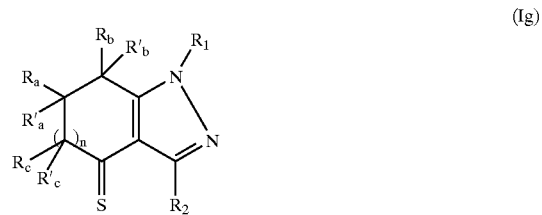

(Ig)

wherein n, $R_1$, $R_2$, Ra, R'a, Rb, Rib, Rc and R'c are as defined above.

5. The compound of claim 1, wherein $R_3$ is 0.
6. The compound of claim 1, wherein $R_3$ is S.
7. The compound of claim 1, wherein $R_3$ is N—R4.
8. The compound of claim 1, wherein $R_4$ is H.
9. The compound of claim 1, wherein $R_4$ is hydroxy.
10. The compound of claim 1, wherein $R_4$ is $C_1$–$C_6$ alkoxy.
11. The compound of claim 1, wherein Ra or R'a, or both, are straight or branched $C_1$–$C_6$ alkyl.
12. The compound of claim 1, wherein Rb or R'b, or both, are group(s) selected from straight or branched $C_1$–$C_6$ alkyl, straight or branched $C_1$–$C_6$ alkoxy, straight or branched $C_1$–$C_6$ alkylthio, cyano, hydroxy, amino, mono- or di-alkylamino with from 1 to 6 carbon atoms in the alkyl chains, arylthio, arylsulfinyl, arylsulfonyl, wherein each of the above aryl and alkyl moieties are optionally further substituted by one or more groups selected from halogen atoms, amino, nitro, hydroxy, $C_1$–$C_6$ alkyl or $C_1$–$C_6$ alkoxy groups.
13. The compound of claim 1, wherein Rc or R'c, or both, are straight or branched $C_1$–$C_6$ alkyl or cyano.
14. A composition comprising the compound of claim 1 and a pharmaceutically acceptable excipient.

* * * * *